United States Patent
Jones et al.

(10) Patent No.: US 11,306,096 B2
(45) Date of Patent: Apr. 19, 2022

(54) 4,6 DIHYDROPYRROLO [3,4-C] PYRAZOLE-5 (1H)-CARBONITRILE DERIVATES FOR TREATING CANCER

(71) Applicant: MISSION THERAPEUTICS LIMITED, Cambridge (GB)

(72) Inventors: Alison Jones, Cambridge (GB); Mark Ian Kemp, Cambridge (GB); Martin Lee Stockley, Cambridge (GB); Michael David Woodrow, Cambridge (GB)

(73) Assignee: MISSION THERAPEUTICS LIMITED, Cambridge (GB)

( * ) Notice: Subject to any disclaimer, the term of this patent is extended or adjusted under 35 U.S.C. 154(b) by 125 days.

(21) Appl. No.: 16/080,229

(22) PCT Filed: Mar. 17, 2017

(86) PCT No.: PCT/GB2017/050755
§ 371 (c)(1),
(2) Date: Aug. 27, 2018

(87) PCT Pub. No.: WO2017/158381
PCT Pub. Date: Sep. 21, 2017

(65) Prior Publication Data
US 2021/0221813 A1 Jul. 22, 2021

(30) Foreign Application Priority Data
Mar. 18, 2016 (GB) ..................... 1604638

(51) Int. Cl.
C07D 487/04 (2006.01)
A61K 31/4162 (2006.01)
A61P 35/00 (2006.01)
C07D 519/00 (2006.01)

(52) U.S. Cl.
CPC ......... *C07D 487/04* (2013.01); *C07D 519/00* (2013.01)

(58) Field of Classification Search
CPC .... C07D 487/04; A61K 31/4162; A61P 35/00
See application file for complete search history.

(56) References Cited

U.S. PATENT DOCUMENTS

2014/0243288 A1  8/2014  Zhang et al.

FOREIGN PATENT DOCUMENTS

| WO | 0177073 A1 | 10/2001 |
|---|---|---|
| WO | 2011087740 A1 | 7/2011 |
| WO | 2012040527 A2 | 3/2012 |
| WO | 2012174199 A1 | 12/2012 |
| WO | 2013030218 A1 | 3/2013 |
| WO | 2015154039 A2 | 10/2015 |
| WO | 2015168286 A1 | 11/2015 |
| WO | 2016/046530 A1 | 3/2016 |
| WO | 2016156816 A1 | 10/2016 |
| WO | 2017/009650 A1 | 1/2017 |
| WO | 2017/093718 A1 | 6/2017 |
| WO | 2017/109488 A1 | 6/2017 |
| WO | 2017103614 A1 | 6/2017 |
| WO | 2017/141036 A1 | 8/2017 |
| WO | 2017/149313 A1 | 9/2017 |

(Continued)

OTHER PUBLICATIONS

Ward et al., "Quantitative Chemical Proteomic Profiling of Ubiquitin Specific Proteases in Intact Cancer Cells," ACS Chem. Biol. 2016, 11, 3268-3272.
STN Registry No. 1933596-01-0 (chemical catalogue), entered Jun. 17, 2016.
The International Search Report and Written Opinion, dated May 4, 2017, in the corresponding PCT Appl. No. PCT/GB2017/050755.
Falgueyret et al., "Novel, Nonpeptidic Cyanamides as Potent and Reversible Inhibitors of Human Cathepsins K and L," J. Med. Chem. 2001, 44, 94-104.
Laine et al., "Discovery of Novel Cyanamide-Based Inhibitors of Cathepsin C," ACS Med. Chem. Lett. 2011, 2, 142-147.
Komander et al, "Breaking the chains: structure and function of the deubiquitinases", Nature Reviews Molecular Cell Biology, 10, 550-563, 2009.

(Continued)

*Primary Examiner* — Bruck Kifle

(57) ABSTRACT

The present invention relates to novel compounds and methods for the manufacture of inhibitors of deubiquitylating enzymes (DUBs) and/or desumoylating enzymes. In particular, the invention relates to the inhibition of ubiquitin C-terminal hydrolase 7 or ubiquitin specific peptidase 7 (USP7). The invention further relates to the use of DUB or desumoylating inhibitors in the treatment of cancer. Described herein are compounds of formula (I) or a pharmaceutically acceptable salt thereof, wherein $R^{1a}$, $R^{1b}$, $R^{1c}$ and $R^{1d}$ each independently represent hydrogen, optionally substituted $C_1$-$C_6$ alkyl or $R^{1a}$ and $R^{1b}$ together form an optionally substituted $C_3$-$C_6$ cycloalkyl ring, or $R^{1c}$ and $R^{1d}$ together form an optionally substituted $C_3$-$C_6$ cycloalkyl ring; A is a 5 membered nitrogen-containing aromatic ring and is substituted with at least one optionally substituted 5 to 10 membered monocyclic or bicyclic heteroaryl or aryl ring attached through an optional linker.

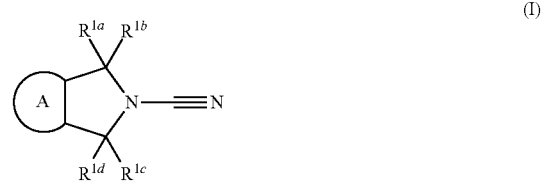

11 Claims, 1 Drawing Sheet

(56) References Cited

FOREIGN PATENT DOCUMENTS

| | | |
|---|---|---|
| WO | 2017/158388 A1 | 9/2017 |
| WO | 2017/163078 A1 | 9/2017 |
| WO | 2018060689 A1 | 4/2018 |
| WO | 2018060691 A1 | 4/2018 |
| WO | 2018060742 A1 | 4/2018 |
| WO | 2018065768 A1 | 4/2018 |

OTHER PUBLICATIONS

Rydzewski et al, "Peptidic 1-Cyanopyrrolidines: Synthesis and SAR of a Series of Potent, Selective Cathepsin Inhibitors", Bioorganic & Medicinal Chemistry 10 (2002) 3277-3284.

Deaton et al, "Novel and potent cyclic cyanamide-based cathepsin K inhibitors", Bioorganic & Medicinal Chemistry Letters 15 (2005) 1815-1819.

Oballa et al, "A generally applicable method for assessing the electrophilicity and reactivity of diverse nitrile-containing compounds", Bioorganic & Medicinal Chemistry Letters 17 (2007) 998-1002.

Zapf et al, "Covalent Inhibitors of Interieukin-2 Inducible T Cell Kinase (Itk) with Nanomolar Potency in a Whole-Blood Assay", J. Med. Chem. 2012, 55, 10047-10063.

Nakamura et al, "Regulation of Mitochondrial Morphology by USP30, a Deubiquitinating Enzyme Present in the Mitochondrial Outer Membrane", Molecular Biology of the Cell, vol. 19, 1903-1911, May 2008.

Bingol et al, "The mitochondrial deubiquitinase USP30 opposes parkin-mediated mitophagy", Nature vol. 510, 370-375, 2014.

Liang et al, "USP30 deubiquitylates mitochondrial Parkin substrates and restricts apoptotic cell death", EMBO Reports, 1-10, 2015; DOI 10.15252/embr.201439820.

Zheng et al, "Heterogeneous expression and biological function of ubiquitin carboxy-terminal hydrolase-L1 in osteosarcoma", Cancer Letters, 359, 36-46, 2015.

Nicholson et al, "The Multifaceted Roles of USP7: New Therapeutic Opportunities", Cell Biochem Biophys, 2011, 60, 61-68.

Van Loosdregt et al, "Stabilization of the Transcription Factor Foxp3 by the Deubiquitinase USP7 Increases Treg-Cell-Suppressive Capacity", Immunity, Aug. 22, 2013; 39, 259-271.

Laurence et al, "A Degrading View of Regulatory T Cells", Immunity, Aug. 22, 2013, 39, 201-203.

Nudubaku et al, "Inhibiting the Deubiquitinating Enzymes (DUBs)", J.Med.Chem., Feb. 26, 2015, 59(4), 1581-95.

Kemp et al, "Recent Advances in the Discovery of Deubiquitinating Enzyme Inhibitors", Progress in Medicinal Chemistry, 2016, 55, 149-192.

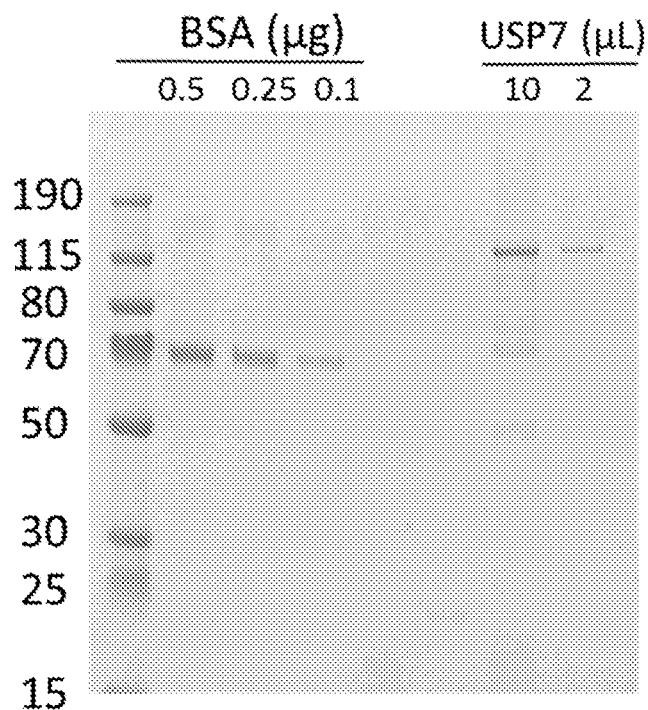
Figure 1 – Expression and Purification of FLAG-USP7 from mammalian cells
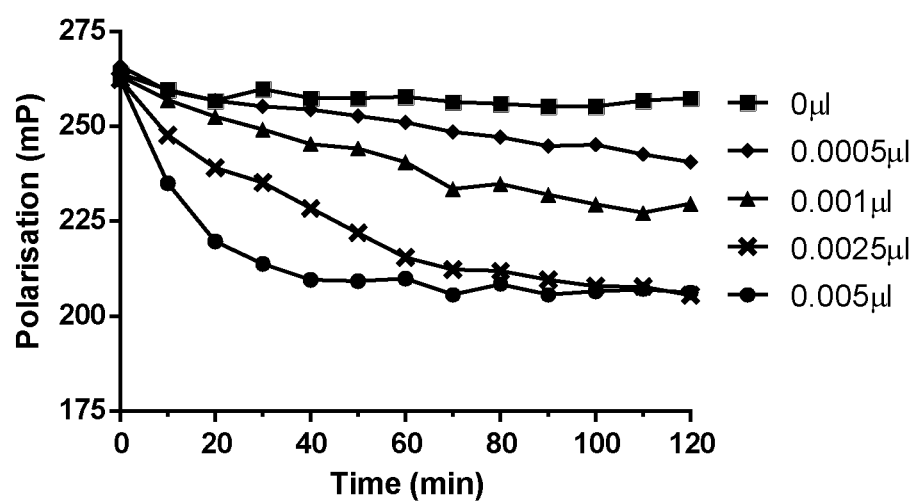
Figure 2 – USP7 assay for high throughput screening of compounds using an isopeptide linked substrate

4,6 DIHYDROPYRROLO [3,4-C] PYRAZOLE-5 (1H)-CARBONITRILE DERIVATES FOR TREATING CANCER

CROSS-REFERENCE TO RELATED APPLICATIONS

This application is a National Stage Application of PCT/GB2017/050755 filed Mar. 17, 2017, which claims priority from UK Patent Application No. 1604638.5, filed on Mar. 18, 2016. The priority of said PCT and UK Patent Application are claimed. Each of the prior mentioned applications is hereby incorporated by reference herein in its entirety.

The present invention relates to novel compounds and methods for the manufacture of inhibitors of deubiquitylating enzymes (DUBs) and/or desumoylating enzymes. In particular, the invention relates to the inhibition of ubiquitin C-terminal hydrolase 7 or ubiquitin specific peptidase 7 (USP7). The invention further relates to the use of DUB or desumoylating inhibitors in the treatment of cancer.

BACKGROUND TO THE INVENTION

The listing or discussion of an apparently prior-published document in this specification should not necessarily be taken as an acknowledgement that the document is part of the state of the art or is common general knowledge.

Ubiquitin is a small protein consisting of 76 amino acids that is important for the regulation of protein function in the cell. In addition to ubiquitin, there are a growing number of structurally related ubiquitin-like molecules (UBLs) that modify substrates in parallel but distinct cellular pathways. These proteins include but are not restricted to small ubiquitin-like modifier (SUMO), interferon-stimulated gene 15 (ISG15), ubiquitin-related modifier-1 (URM1), neuronal-precursor-cell-expressed developmentally downregulated protein-8 (NEDD8), human leukocyte antigen F-associated (FAT10), autophagy-8 (ATG8) and -12 (ATG12), few ubiquitin-like protein (FUB1), membrane-anchored UBL (MUB), ubiquitin fold-modifier-1 (UFM1) and ubiquitin-like protein-5 (UBL5). Ubiquitylation and deubiquitylation of ubiquitin and UBLs are enzymatically mediated processes by which ubiquitin or UBLs are covalently bound or cleaved from a target protein by ubiquitylating enzymes and deubiquitylating enzymes (DUBs). Including the Sentrin specific proteases (SENPs), there are approximately 95 DUBs in human cells, divided into sub-families based on sequence homology, the largest of these being the USP family that is characterised by a common Cys and His box containing Cys and His residues critical for DUB activity. The ubiquitylation and deubiquitylation processes have been implicated in the regulation of many cellular functions including cell cycle progression, apoptosis, modification of cell surface receptors, regulation of DNA transcription and DNA repair. Thus, the ubiquitin system has been implicated in the pathogenesis of numerous disease states including inflammation, viral infection, metabolic dysfunction, CNS disorders, and oncogenesis.

USP7 is a DUB with strong oncology links and is an established anti-cancer target. The rationale behind targeting USP7 is principally due to its well validated role in regulating multiple oncogenes, tumour suppressors, viral proteins and epigenetic regulators including Phosphatase and tensin homolog (PTEN), Forkhead box protein O4 (FOXO4), the p53:HDM2 axis and DNA (cytosine-5)-methyltransferase 1 (DNMT1). Inhibition of USP7 causes degradation of Human double minute 2 homolog (HDM2), stabilisation of p53 and activation of apoptosis in tumour cells meaning it is a potential target for cancers where there is deregulated HDM2 expression (~7% of all cancers) and/or wild-type p53 (~50% of all cancers). In addition, USP7 inhibition has also been shown to reduce the immune-suppressive capacity of regulatory T-cells. Thus, USP7 inhibitors may have synergistic anti-cancer effects by boosting surveillance and killing of cancer cells by the host immune system.

The ubiquitin-proteasome system has gained interest as a target for the treatment of cancer following the approval of the proteasome inhibitor bortezomib for the treatment of multiple myeloma. Extended treatment with bortezomib is limited by its associated toxicity and drug resistance. However, therapeutic strategies that target specific aspects of the ubiquitin-proteasome pathway upstream of the proteaseome, such as DUBs, are predicted to be better tolerated. Although there is strong interest in this field, DUB inhibitors have yet to enter the market (Kemp M, Progress in Medicinal Chemistry 2016; 55:140-192). Thus, there is a need for compounds and pharmaceutical compositions to inhibit DUBs such as USP7 for the treatment of indications where DUB activity is observed, including, although not limited to, cancer.

WO2013044865 describes the compounds benzyl (4-(5-cyano-5,6-dihydropyrrolo[3,4-d][1,2,3]triazol-2(4H)-yl)-3-fluorophenyl)carbamate and 2-(2-fluoro-4-nitrophenyl)-2,6-dihydropyrrolo[3,4-c]pyrazole-5(4H)-carbonitrile as intermediates in methods for preparing antibiotic compounds. These compounds may be disclaimed from the appended claims.

SUMMARY OF THE INVENTION

Described herein are compounds of formula I:

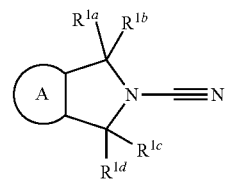

(I)

or a pharmaceutically acceptable salt thereof, wherein $R^{1a}$, $R^{1b}$, $R^{1c}$ and $R^{1d}$ each independently represent hydrogen, optionally substituted $C_1$-$C_6$ alkyl or $R^{1a}$ and $R^{1b}$ together form an optionally substituted $C_3$-$C_6$ cycloalkyl ring, or $R^{1c}$ and $R^{1d}$ together form an optionally substituted $C_3$-$C_6$ cycloalkyl ring;

A is a 5 membered nitrogen-containing aromatic ring and is substituted with at least one optionally substituted 5 to 10 membered monocyclic or bicyclic heteroaryl or aryl ring attached through an optional linker.

In one embodiment, A is substituted with -$Q^1$-B and (-$Q^2$-(D)$_m$)$_n$;

m represents 0 or 1;
n represents 0, 1 or 2;
$Q^1$ represents a covalent bond or a linker selected from an oxygen atom, a sulphur atom, —$OR^4$—, —SO—, —$SO_2$—, —C(O)—, —C(O)O—, —$C_0$-$C_3$-alkylene-C(O)$NR^2$—$C_0$-$C_3$ alkylene, —$C_0$-$C_3$-alkylene-$NR^2$—$C_0$-$C_3$-alkylene-, —$C_0$-$C_3$-alkylene-$NR^2$C(O)—$C_0$-$C_3$-alkylene, —$NR^2$C(O)$NR^3$—, —$SO_2NR^2$—, $NR^2SO_2$—, —$NR^2SO_2NR^3$—, —NR²C(O)O—, —NR²C(O)OR⁴—, optionally substituted —$C_1$-$C_6$ alkylene, or optionally substituted —$C_2$-$C_6$ alkenylene;

B represents an optionally substituted 5 to 10 membered monocyclic or bicyclic aryl or heteroaryl ring;

$R^2$ and $R^3$ each independently represent hydrogen or optionally substituted $C_1$-$C_6$ alkyl;

$R^4$ represents optionally substituted $C_1$-$C_6$ alkylene;

each occurrence of $Q^2$ independently represents halogen, cyano, nitro, hydroxyl, —SR⁵, —NR⁵R⁶, —CONR⁵R⁶, —$C_0$-$C_3$-alkylene-NR⁵COR⁶—, —NR⁵CONR⁶R⁶ᵃ, —COR⁵, —C(O)OR⁵, —SO₂R⁵, —SO₂NR⁵R⁶, —NR⁵SO₂R⁶, —NR⁵SO₂NR⁶R⁶ᵃ, —NR⁵C(O)OR⁶, optionally substituted —$C_1$-$C_6$ alkyl, optionally substituted —$C_2$-$C_6$ alkenyl, a covalent bond, an oxygen atom, a sulphur atom, —OR⁷—, —SO—, —SO₂—, —CO—, —C(O)O—, —$C_0$-$C_3$-alkylene-C(O)NR⁵—$C_0$-$C_3$ alkylene, —$C_0$-$C_3$-alkylene-NR⁵—$C_0$-$C_3$ alkylene, —$C_0$-$C_3$-alkylene-NR⁵C(O)—$C_0$-$C_3$ alkylene, —NR⁵CONR⁶—, —SO₂NR⁵—, NR⁵SO₂—, —NR⁵SO₂NR⁶—, —NR⁵C(O)O—, —NR⁵C(O)OR⁷—, optionally substituted $C_1$-$C_6$ alkylene, or optionally substituted —$C_2$-$C_6$ alkenylene;

each occurrence of D independently represents an optionally substituted 3 to 10 membered monocyclic or bicyclic heterocyclyl, heteroaryl, cycloalkyl or aryl ring;

$R^5$, $R^6$ and $R^{6a}$ each independently represent hydrogen or optionally substituted $C_1$-$C_6$ alkyl;

$R^7$ represents optionally substituted $C_1$-$C_6$ alkylene.

The invention also relates to pharmaceutical compositions comprising the compounds of the present invention and one or more pharmaceutically acceptable excipients.

The compounds of the invention are useful for the treatment of cancer.

BRIEF DESCRIPTION OF THE FIGURES

FIG. 1 provides an image of FLAG-USP7 purified from mammalian cells. FLAG-purified protein or the indicated concentrations of BSA were separated by SDS-PAGE and stained with Imperial Protein Stain (Pierce Biotechnology).

FIG. 2 is a graph showing proteolytic activity of purified FLAG-USP7 using a fluorescence polarisation assay. Various volumes of purified USP7 as indicated were incubated with a TAMRA labelled peptide linked to ubiquitin via an isopeptide bond.

DETAILED DESCRIPTION OF THE INVENTION

The definitions and explanations below are for the terms as used throughout this entire document including both the specification and the claims. Reference to compounds as described herein (e.g. a compound of Formula I), includes reference to Formula I and II including any sub-generic embodiments thereof.

Where any group of the compounds of formula I have been referred to as optionally substituted, this group may be substituted or unsubstituted. Substitution may be by one or more of the specified substituents which may be the same or different. It will be appreciated that the number and nature of substituents will be selected to avoid any sterically undesirable combinations.

In the context of the present specification, unless otherwise stated an alkyl, alkylene, alkoxy, alkenyl, or alkynyl substituent (or linker) group or an alkyl, alkenyl moiety in a substituent group may be linear or branched. Alkyl, alkylene, alkenyl and alkenylene chains may also include intervening heteroatoms such as oxygen.

$C_x$-$C_y$ alkyl refers to a saturated aliphatic hydrocarbon group having x-y carbon atoms which may be linear or branched. For example $C_1$-$C_6$ alkyl contains from 1 to 6 carbon atoms and includes $C_1$, $C_2$, $C_3$, $C_4$, $C_5$ and $C_6$. "Branched" means that at least one carbon branch point is present in the group. For example, tert-butyl and isopropyl are both branched groups. Examples of $C_1$-$C_6$ alkyl groups include methyl, ethyl, propyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, n-butyl, isobutyl, tert-butyl, n-pentyl, isopentyl, neopentyl and n-hexyl. $C_1$-$C_6$ alkyl, $C_1$-$C_4$ alkyl and $C_1$-$C_3$ alkyl within the definitions of $R^{1a}$, $R^{1b}$, $R^{1c}$, $R^{1d}$, $R^2$, $R^3$, $R^5$, $R^6$, $R^{6a}$, $R^{11}$, $R^{12}$, $R^{12a}$, $R^{14}$, $R^{15}$, $R^{15a}$, $Q^2$, and within the definition of substituents for B and D, may be unsubstituted or substituted with one or more of the substituents defined herein. Examples of substituted $C_1$-$C_6$ alkyl therefore include $CF_3$, $CH_2CF_3$, $CH_2CN$, $CH_2OH$ and $CH_2CH_2OH$.

A $C_x$-$C_y$ alkylene group or moiety may be linear or branched and refers to a divalent hydrocarbon group having one less hydrogen atom from $C_x$-$C_y$ alkyl as defined above. $C_1$-$C_6$ alkylene may include intervening heteroatoms such as oxygen, and therefore includes alkyleneoxy groups. Alkyleneoxy as employed herein also extends to embodiments in which the or an oxygen atom (e.g. a single oxygen atom) is located within the alkylene chain, for example $CH_2CH_2OCH_2$ or $CH_2OCH_2$. Examples of $C_1$-$C_6$ alkylene groups include methylene, methyleneoxy, ethylene, ethyleneoxy, n-propylene, n-propyleneoxy, n-butylene, n-butyleneoxy, methylmethylene and dimethylmethylene. Unless stated otherwise, $C_1$-$C_6$ alkylene, $C_1$-$C_4$ alkylene and $C_1$-$C_3$ alkylene within the definitions of $R^4$, $R^7$, $Q^1$, $Q^2$, $Q^{3a}$, $Q^{3b}$, $Q^{4a}$, $Q^{4b}$ may be unsubstituted or substituted with one or more of the substituents defined herein.

$C_2$-$C_6$ alkenyl refers to a linear or branched hydrocarbon chain radical containing at least two carbon atoms and at least one double bond and includes $C_2$-$C_4$ alkenyl. Examples of alkenyl groups include ethenyl, propenyl, 2-propenyl, 1-butenyl, 2-butenyl, 1-hexenyl, 2-methyl-1-propenyl, 1,2-butadienyl, 1,3-pentadienyl, 1,4-pentadienyl and 1-hexadienyl. Unless stated otherwise, $C_2$-$C_6$ alkenyl and $C_2$-$C_4$ alkenyl within the definition of $Q^2$ and within the definition of substituents for B and D, may be unsubstituted or substituted with one or more of the substituents defined herein.

$C_2$-$C_6$ alkenylene refers to linear or branched hydrocarbon group having one less hydrogen atom from $C_2$-$C_6$ alkenyl as defined above. Examples of $C_2$-$C_6$ alkenylene include ethenylene, propenylene and butenylene. Unless stated otherwise, $C_2$-$C_6$ alkenylene and $C_2$-$C_4$ alkenylene within the definition of substituents for $Q^1$, $Q^2$, $Q^{3a}$, $Q^{3b}$, and $Q^{4a}$, $Q^{4b}$, may be unsubstituted or substituted with one or more of the substituents defined herein.

$C_2$-$C_6$ alkynyl refers to a linear or branched hydrocarbon chain radical containing at least two carbon atoms and at least one triple bond. Examples of alkenyl groups include ethynyl, propynyl, 2-propynyl, 1-butynyl, 2-butynyl and 1-hexynyl. Unless specified otherwise, $C_2$-$C_6$ alkynyl, within the definition of substituents for B and D, may be unsubstituted or substituted with one or more of the substituents defined herein.

$C_1$-$C_6$ alkoxy refers to a group or part of a group having an —O—$C_x$-$C_y$ alkyl group according to the definition of $C_x$-$C_y$ alkyl above. $C_1$-$C_6$ alkoxy contains from 1 to 6 carbon atoms and includes $C_1$, $C_2$, $C_3$, $C_4$, $C_5$ and $C_6$. Examples of $C_1$-$C_6$ alkoxy include methoxy, ethoxy, propoxy, isopropoxy, butoxy, pentoxy and hexoxy. Alkoxy as employed herein also extends to embodiments in which the or an oxygen atom (e.g. a single oxygen atom) is located within the alkyl chain, for example $CH_2CH_2OCH_3$ or $CH_2OCH_3$. Thus the alkoxy may be linked through carbon to the remainder of the molecule, for example, —$CH_2CH_2CH_3$, or alternatively, the alkoxy is linked through oxygen to the remainder of the molecule, for example —$OC_{1-6}$ alkyl. In certain instances, the alkoxy may be linked through oxygen to the remainder of the molecule but the alkoxy group contains a further oxygen atom, for example —$OCH_2CH_2OCH_3$. Unless specified otherwise, $C_1$-$C_6$ alkoxy and $C_1$-$C_3$ alkoxy within the definitions $Q^2$ and within the definition of substituents for B and D, may be unsubstituted or substituted with one or more of the substituents defined herein. Examples of substituted $C_1$-$C_6$ alkoxy therefore include $OCF_3$, $OCHF_2$, $OCH_2CF_3$, $CH_2CH_2OCH_3$ and $CH_2CH_2OCH_2CH_3$.

The term "halogen" or "halo" refers to chlorine, bromine, fluorine or iodine atoms, in particular chlorine or fluorine atoms.

The term "oxo" means =O.

For the avoidance of doubt it will be understood that the cycloalkyl, heterocyclyl, aryl and heteroaryl rings disclosed herein and within the definitions of $R^{1a}$, $R^{1b}$, $R^{1c}$, $R^{1d}$, $R^{13}$, $R^{16}$, $R^{12}$, B and D, do not include any unstable ring structures or, in the case of heteroaryl and heterocyclic ring systems, any O—O, O—S or S—S bonds. The ring systems may be monocyclic or bicyclic. Bicyclic ring systems include bridged, fused and spiro ring systems. A substituent if present may be attached to any suitable ring atom which may be a carbon atom or, in the case of heteroaryl and heterocyclic ring systems, a heteroatom. Substitution on a ring may also include a change in the ring atom at the position of the substitution. For example, substitution on a phenyl ring may include a change in the ring atom at the position of substitution from carbon to nitrogen, resulting in a pyridine ring.

"cycloalkyl" refers to a monocyclic saturated or partially unsaturated, non-aromatic ring, wherein all of the ring atoms are carbon, and having the number of ring atoms as indicated. For example $C_3$-$C_{10}$ cycloalkyl refers to a monocyclic or bicyclic hydrocarbon ring containing 3 to 10 carbon atoms. Examples of $C_3$-$C_{10}$ cycloalkyl are cyclopropyl, cyclobutyl, cyclopentyl, cyclohexyl, cycloheptyl, cyclooctyl and decahydronaphthalenyl. Bicyclic cycloalkyl groups include bridged ring systems such as bicycloheptane and bicyclooctane. Unless specified otherwise, cycloalkyl within the definitions of $R^{1a}$, $R^{1b}$, $R^{1c}$, $R^{1d}$, $R^{13}$, $R^{16}$, D, may be unsubstituted or substituted with one or more of the substituents defined herein.

An "aryl" group/moiety refers to any monocyclic or bicyclic hydrocarbon group comprising at least one aromatic group and having from 5 to 10 carbon atom ring members. Examples of aryl groups include phenyl and naphthyl. Bicyclic rings may be fused aromatic rings where both rings are aromatic, for example, naphthalenyl. Preferred aryl groups are phenyl and naphthyl, more preferably phenyl. Unless specified otherwise, aryl within the definitions of $R^{13}$, $R^{16}$, B and D, may be unsubstituted or substituted with one or more of the substituents defined herein.

"Heteroaryl" as used herein means a polyunsaturated, monocyclic or bicyclic 5 to 10 membered aromatic moiety containing at least one and up to 5 heteroatoms, particularly 1, 2 or 3 heteroatoms selected from N, O and S, and the remaining ring atoms are carbon atoms, in stable combinations known to the skilled person. Heteroaryl ring nitrogen and sulphur atoms are optionally oxidised, and the nitrogen atom(s) are optionally quaternized. A heteroaryl ring can be a single aromatic ring or a fused bicyclic ring where the bicyclic ring system can be aromatic, or one of the fused rings is aromatic and the other is at least partially saturated. In one example, a bicyclic heteroaryl is one in which the entire fused ring system is aromatic. A bicyclic heteroaryl can have the at least one heteroatom in either of the fused rings. For example, a bicyclic ring with an aromatic ring fused to a partially saturated ring may contain the at least one heteroatom in the aromatic ring or the partially saturated ring. Attachment of the bicyclic ring to the group it is a substituent of may be via either a heteroatom containing ring or a carbon only containing ring. The point of attachment of heteroaryl to the group it is a substituent of can be via a carbon atom or a heteroatom (e.g. nitrogen). Examples or heteroaryl rings include pyridinyl, pyrazinyl, pyrimidinyl, pyridazinyl, furyl, pyrrolyl, oxazolyl, thiazolyl, pyrazolyl, triazolyl, tetrazolyl, indolyl, indolizinyl, isoindolyl, purinyl, furazanyl, imidazolyl, indazolyl, isothiazolyl, isoxazolyl, oxadiazolyl, tetrazolyl, thiadiazolyl, benzofuranyl, isobenzofuranyl, benzothiophenyl, isobenzothiophenyl, benzimidazolyl, benzothiazolyl, napthyridinyl, pteridinyl, pyrazinyl, quinolinyl, isoquinolinyl, cinnolinyl, phthalazinyl, quinazolinyl, imidazopyridinyl, pyrazolopyridinyl, thiazolopyridinyl, triazinyl, dihydrophyridinyl, dihydropyrrolopyridinyl, quinoxalinyl and dihydrobenzoxazinyl. Unless specified otherwise, heteroaryl within the definitions of $R^{13}$, $R^{16}$, B and D, may be unsubstituted or substituted with one or more of the substituents defined herein.

"Heterocyclyl" or "heterocyclic" as used herein in describing a ring means, unless otherwise stated, a monocyclic saturated or partially unsaturated, non-aromatic ring or a bicyclic saturated or partially unsaturated ring, wherein the bicyclic ring system is non-aromatic, the mono- or bicyclic ring having, for example, 3 to 10 members, where at least one member and up to 5 members, particularly 1, 2 or 3 members of the ring are heteroatoms selected from N, O and S, and the remaining ring atoms are carbon atoms, in stable combinations known to those of skill in the art. Heterocyclic ring nitrogen and sulphur atoms are optionally oxidised, and the nitrogen atoms(s) are optionally quaternized. As used herein, the heterocyclic ring may be a fused ring to another ring system to form a bicycle, i.e. one or two of the heterocyclic ring carbons is common to an additional ring system. In instances where the heterocyclyl is a bicyclic ring, the second ring can be aromatic, e.g. a fused phenyl, pyridyl, pyrazolyl, or the like. The heterocyclyl may be linked through carbon or a heteroatom to the remainder of the molecule and in instances where the heterocyclyl is a bicyclic ring, the link may be via the heteroatom containing ring or the fused ring. Examples of heterocyclyl groups include azetidinyl, pyrrolidinyl, piperidinyl, azepanyl, diazepanyl, dihydrofuranyl (e.g. 2,3-dihydrofuranyl, 2,5-dihydrofuranyl), dioxolanyl, morpholinyl, oxazolidinyl, oxazinanyl, indolinyl, isoindolinyl, piperazinyl, tetrahydrofuranyl, thiomorpholinyl, dihydropyranyl (e.g. 3,4-dihydropyranyl, 3,6-dihydropyranyl), homopiperazinyl, dioxanyl, hexahydropyrimidinyl, pyrazolinyl, pyrazolidinyl, 4H-quinolizinyl, quinuclidinyl, tetrahydropyranyl, tetrahydropyridinyl, tetrahydropyrimidinyl, tetrahydrothiophenyl, thiazolidinyl, benzopyranyl, tetrahydroquinolinyl, dihydropyrrolopyridinyl, dihydrobenzoxazinyl and tetrahydroisoquinolinyl. Unless specified otherwise, heterocyclyl within the definitions of $R^{13}$, $R^{16}$, B and D, may be unsubstituted or substituted with one or more of the substituents defined herein. Examples of substituted heterocyclyl rings include for example 4,5-dihydro-1H-maleimido, tetramethylenesulfoxide and hydantoinyl.

"Optionally substituted" as applied to any group means that the said group may if desired be substituted with one or more substituents (e.g., 1, 2, 3 or 4 substituents) which may be the same or different.

Examples of suitable substituents for "substituted" and "optionally substituted" $C_1$-$C_6$ alkyl (including $C_1$-$C_4$ alkyl, $C_1$-$C_3$ alkyl and $C_1$-$C_2$ alkyl) and $C_1$-$C_6$ alkoxy (including $C_1$-$C_4$ alkoxy, $C_1$-$C_3$ alkoxy and $C_1$-$C_2$ alkoxy) and $C_2$-$C_6$ alkenyl (including $C_2$-$C_4$ alkenyl) and $C_2$-$C_6$ alkynyl (including $C_2$-$C_4$ alkynyl), for example within the definitions of $R^{1a}$, $R^{1b}$, $R^{1c}$, $R^{1d}$, $R^2$, $R^3$, $R^5$, $R^6$, $R^{6a}$, $R^{11}$, $R^{12}$, $R^{12a}$, $R^{14}$, $R^{15}$, $R^{15a}$, $Q^2$, and within the definition of substituents for B and D, and $C_1$-$C_6$ alkylene (including $C_1$-$C_3$ alkylene) and $C_2$-$C_6$ alkenylene, for example within the definitions of $R^5$, $R^9$, $R^{12}$, $R^{15}$, $Q^1$, $Q^2$, $Q^{3a}$, $Q^{3b}$, $Q^{4a}$, $Q^{4b}$ include halogen, cyano, oxo, nitro, amino, amido, hydroxy, $C_1$-$C_6$ alkyl or $C_1$-$C_3$ alkyl, $C_1$-$C_6$ alkoxy or $C_1$-$C_3$ alkoxy, aryl, heteroaryl, heterocyclyl, $C_3$-$C_6$ cycloalkyl, $C_{1-3}$ alkylamino, $C_{2-6}$ alkenylamino, di-$C_1$-$C_3$ alkylamino, $C_1$-$C_3$ acylamino, di-$C_1$-$C_3$ acylamino, carboxy, $C_1$-$C_3$ alkoxycarbonyl, carboxamidyl, carbamoyl, mono-$C_{1-3}$ carbamoyl, di-$C_{1-3}$ carbamoyl or any of the above in which a hydrocarbyl moiety is itself substituted by halogen, e.g. fluorine, hydroxyl, cyano, amino, nitro or $SF_5$ (a known mimetic of nitro). In particular, suitable substituents may be selected from halogen, hydroxyl, thiol, cyano, amino, amido, nitro and $SF_5$ (a known mimetic of nitro), in particular, halogen (preferably fluorine or chlorine), hydroxyl and cyano.

Examples of suitable substituents for all remaining "substituted" and "optionally substituted" moieties, including the cycloalkyl, heterocyclyl, aryl and heteroaryl rings within the definitions of $R^{1a}$, $R^{1b}$, $R^{1c}$, $R^{1d}$, $R^2$, $R^6$, $R^{12}$, $R^{15}$, include halogen, cyano, oxo, nitro, amino, amido, hydroxy, amido, $C_1$-$C_6$ alkyl or $C_1$-$C_3$ alkyl, $C_1$-$C_6$ alkoxy or $C_1$-$C_3$ alkoxy, aryl, heteroaryl, heterocyclyl, $C_3$-$C_6$ cycloalkyl, $C_{1-3}$ alkylamino, $C_{2-6}$ alkenylamino, di-$C_1$-$C_3$ alkylamino, $C_1$-$C_3$ acylamino, di-$C_1$-$C_3$ acylamino, carboxy, $C_1$-$C_3$ alkoxycarbonyl, carboxamidyl, carbamoyl, mono-$C_{1-3}$ carbamoyl, di-$C_{1-3}$ carbamoyl or any of the above in which a hydrocarbyl moiety is itself substituted by halogen, e.g. fluorine, hydroxyl, cyano, amino, amido, nitro or $SF_5$ (a known mimetic of nitro).

Examples of suitable substituents for "substituted" and "optionally substituted" rings include in particular, fluorine, chlorine, oxo, cyano, $C_1$-$C_3$ alkyl, $C_1$-$C_3$ alkoxy, heterocyclyl, cycloalkyl, heteroaryl or aryl, wherein the alkyl or alkoxy is optionally substituted with one or more (e.g. one, two or three) substituents selected from halogen, hydroxyl, thiol, cyano, amino, amido, nitro and $SF_5$.

Substituted groups thus include for example Br, Cl, F, CN, Me, Et, Pr, t-Bu, OMe, OEt, OPr, $C(CH_3)_3$, $CH(CH_3)_2$, $CF_3$, $OCF_3$, $C(O)NHCH_3$, cyclopropyl, phenyl, etc. In the case of aryl groups, the substitutions may be in the form of rings from adjacent carbon atoms in the aryl ring, for example cyclic acetals such as O—$CH_2$—O.

In substituted groups containing an oxygen atom such as hydroxy and alkoxy, the oxygen atom can be replaced with sulphur to make groups such as thio (SH) and thio-alkyl (S-alkyl). Optional substituents therefore include groups such as S-methyl. In thio-alkyl groups, the sulphur atom may be further oxidised to make a sulfoxide or sulfone, and thus optional substituents therefore includes groups such as S(O)-alkyl and $S(O)_2$-alkyl.

The term "treat" or "treating" or "treatment" includes prophylaxis and means to ameliorate, alleviate symptoms, eliminate the causation of the symptoms either on a temporary or permanent basis, or to prevent or slow the appearance of symptoms of the named disorder or condition. The compounds of the invention are useful in the treatment of humans and non-human animals.

The dose of the compound is that amount effective to prevent occurrence of the symptoms of the disorder or to treat some symptoms of the disorder from which the patient suffers. By "effective amount" or "therapeutically effective amount" or "effective dose" is meant that amount sufficient to elicit the desired pharmacological or therapeutic effects, thus resulting in effective prevention or treatment of the disorder. Prevention of the disorder is manifested by delaying the onset of the symptoms of the disorder to a medically significant extent. Treatment of the disorder is manifested by a decrease in the symptoms associated with the disorder or an amelioration of the reoccurrence of the symptoms of the disorder.

Pharmaceutically acceptable salts of the compounds of the invention include but are not limited to addition salts (for example phosphates, nitrates, sulphates, borates, acetates, maleates, citrates, fumarates, succinates, methanesulphonates, benzoates, salicylates and hydrohalides), salts derived from organic bases (such as lithium, potassium and sodium), salts of amino acids (such as glycine, alanine, valine, leucine, isoleucine, cysteine, methionine and proline), inorganic bases (such as triethylamine, hydroxide, choline, thiamine and N—N'-diacetylethylenediamine). Other pharmaceutically acceptable salts include ammonium salts, substituted ammonium salts and aluminium salts. Further pharmaceutically acceptable salts include quaternary ammonium salts of the compounds of the invention.

General methods for the production of salts are well known to the person skilled in the art. Such salts may be formed by conventional means, for example by reaction of a free acid or a free base form of a compound with one or more equivalents of an appropriate acid or base, optionally in a solvent, or in a medium in which the salt is insoluble, followed by removal of said solvent, or said medium, using standard techniques (e.g. in vacuo, by freeze-drying or by filtration). Salts may also be prepared by exchanging a counter-ion of a compound in the form of a salt with another counter-ion, for example using a suitable ion exchange resin.

Where compounds of the invention exist in different enantiomeric and/or diastereoisomeric forms, the invention relates to these compounds prepared as isomeric mixtures or racemates whether present in an optically pure form or as mixtures with other isomers. Enantiomers differ only in their ability to rotate plane-polarized light by equal amounts in opposite directions and are denoted as the (+)/(S) or (−)/(R) forms respectively. Individual enantiomers or isomers may be prepared by methods known in the art, such as optical resolution of products or intermediates (for example chiral chromatographic separation e.g. chiral HPLC, or an asymmetric synthesis approach). Similarly where compounds of the invention exist as alternative tautomeric forms e.g. keto/enol, amide/imidic acid, the invention relates to the individual tautomers in isolation, and to mixtures of the tautomers in all proportions.

Isotopes

The compounds described herein may contain one or more isotopic substitutions, and a reference to a particular element includes within its scope all isotopes of the element. For example, a reference to hydrogen includes within its scope $^1H$, $^2H$ (D), and $^3H$ (T). Similarly, references to carbon and oxygen include within their scope respectively $^{12}C$, $^{13}C$ and $^{14}C$ and $^{16}O$ and $^{18}O$. Examples of isotopes include $^2H$, $^3H$, $^{11}C$, $^{13}C$, $^{14}C$, $^{36}Cl$, $^{18}F$, $^{123}I$, $^{125}I$, $^{13}N$, $^{15}N$, $^{15}O$, $^{17}O$, $^{18}O$, $^{32}P$ and $^{35}S$.

In an analogous manner, a reference to a particular functional group also includes within its scope isotopic variations, unless the context indicates otherwise. For example, a reference to an alkyl group such as an ethyl group also covers variations in which one or more of the hydrogen atoms in the group is in the form of a deuterium or tritium isotope, e.g. as in an ethyl group in which all five hydrogen atoms are in the deuterium isotopic form (a perdeuteroethyl group). Deuterium may be referred to throughout as "deutero".

The isotopes may be radioactive or non-radioactive. In one embodiment, the compounds contain no radioactive isotopes. Such compounds are preferred for therapeutic use. In another embodiment, however, the compounds may contain one or more radioisotopes. Compounds containing such radioisotopes may be useful in a diagnostic context.

Certain isotopically labelled compounds of formula (I), for example, those incorporating a radioactive isotope, are useful in drug and/or substrate tissue distribution studies. The radioactive isotopes i.e. $^3H$ and $^{14}C$ are particularly useful for this purpose in view of their ease of incorporation and ready means of detection. Substitution with heavier isotopes i.e. $^2H$, may afford certain therapeutic advantages resulting from greater metabolic stability, for example, increased in vivo half-life or reduced dosage requirements, and hence may be preferred in some circumstances. Substitution with positron emitting isotopes, such as $^{11}C$, $^{18}F$, $^{15}O$ and $^{13}N$, can be useful in Positron Emission Topography (PET) studies for examining receptor occupancy. Isotopically labelled compounds of formula (I) can generally be prepared by conventional techniques known to those skilled in the art or by processes analogous to those described in the accompanying examples and preparations using an appropriate isotopically labelled reagent in place of the non-labelled reagent previously employed.

Crystalline and Amorphous Forms

The compounds of formula (I) may exist in crystalline or amorphous form and some of the crystalline forms may exist as polymorphs, which are included within the scope of the present invention. Polymorphic forms of compounds of formula (I) may be characterised and differentiated using a number of conventional analytical techniques, including, but not limited to, infra-red spectra, Raman spectra, X-ray powder diffraction, differential scanning calorimetry, thermogravimetric analysis and solid state nuclear magnetic resonance.

Accordingly, in further embodiments, the invention provides a compound according to any described embodiments in a crystalline form. The compound may be from 50% to 100% crystalline, and more particularly is at least 50% crystalline, or at least 60% crystalline, or at least 70% crystalline, or at least 80% crystalline, or at least 90% crystalline, or at least 95% crystalline, or at least 98% crystalline, or at least 99% crystalline, or at least 99.5% crystalline, or at least 99.9% crystalline, for example 100% crystalline. The compound may alternatively be in an amorphous form.

The invention described herein relates to all crystal forms, solvates and hydrates of any of the disclosed compounds however so prepared. To the extent that any of the compounds disclosed herein have acid or basic centres such as carboxylates or amino groups, then all salt forms of said compounds are included herein. In the case of pharmaceutical uses, the salt should be seen as being a pharmaceutically acceptable salt.

The invention relates to any solvates of the compounds and their salts. Preferred solvates are solvates formed by the incorporation into the solid state structure (e.g. crystal structure) of the compounds of the invention of molecules of a non-toxic pharmaceutically acceptable solvent (referred to below as the solvating solvent). Examples of such solvents include water, alcohols (such as ethanol, isopropanol and butanol) and dimethylsulfoxide. Solvates can be prepared by recrystallising the compounds of the invention with a solvent or mixture of solvents containing the solvating solvent. Whether or not a solvate has been formed in any given instance can be determined by subjecting crystals of the compound to analysis using well known and standard techniques such as thermogravimetric analysis (TGE), differential scanning calorimetry (DSC) and X-ray crystallography.

The solvates can be stoichiometric or non-stoichiometric solvates. Particular solvates may be hydrates, and examples of hydrates include hemihydrates, monohydrates and dihydrates. For a more detailed discussion of solvates and the methods used to make and characterise them, see Bryn et al., Solid-State Chemistry of Drugs, Second Edition, published by SSCI, Inc of West Lafayette, Ind., USA, 1999, ISBN 0-967-06710-3.

The invention relates to pharmaceutically functional derivatives of compounds as defined herein including ester derivatives and/or derivatives that have, or provide for, the same biological function and/or activity as any relevant compound of the invention. Thus, for the purposes of this invention, the term also includes prodrugs of compounds as defined herein.

The term "prodrug" of a relevant compound includes any compound that, following oral or parenteral administration, is metabolised in vivo to form that compound in an experimentally-detectable amount, and within a predetermined time (e.g. within a dosing interval of between 6 and 24 hours (i.e. once to four times daily).

Prodrugs of compounds may be prepared by modifying functional groups present on the compound in such a way that the modifications are cleaved, in vivo when such prodrug is administered to a mammalian subject. The modifications typically are achieved by synthesizing the parent compound with a prodrug substituent. Prodrugs include compounds wherein a hydroxyl, amino, sulfhydryl, carboxyl or carbonyl group in a compound is bonded to any group that may be cleaved in vivo to regenerate the free hydroxyl, amino, sulfhydryl, carboxyl or carbonyl group, respectively.

Examples of prodrugs include, but are not limited to, esters and carbamates of hydroxyl functional groups, ester groups of carboxyl functional groups, N-acyl derivatives and N-Mannich bases. General information on prodrugs may be found e.g. in Bundegaard, H. "Design of Prodrugs" p. 1-92, Elsevier, New York-Oxford (1985).

Compounds of the invention may be metabolised in vivo. Metabolites of compounds of formula (I) are also within the scope of the present invention. The term 'metabolites' refers to all molecules derived from any of the compounds according to the present invention in a cell or organism, preferably mammal. Preferably the term relates to molecules which differ from any molecule which is present in any such cell or organism under physiological conditions.

A treatment defined herein may be applied as a sole therapy of may involve, in addition to the compounds of the invention, conventional surgery or radiotherapy or chemotherapy. Furthermore, compounds of formula (I) can also be used in combination with existing therapeutic agents for the treatment of conditions associated with cancer, including small molecule therapeutics or antibody based therapeutics.

The compounds of the invention are characterised by a 8 membered bicyclic ring structure which is formed from a cyanopyrrolidine core fused to a 5 membered aromatic ring, wherein the aromatic ring contains at least one nitrogen heteroatom.

In accordance with a first aspect of the invention there is provided a compound of formula I:

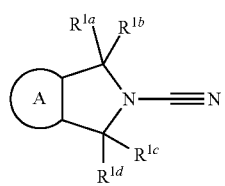

(I)

or a pharmaceutically acceptable salt thereof, wherein:
$R^{1a}$, $R^{1b}$, $R^{1c}$ and $R^{1d}$ each independently represent hydrogen, optionally substituted $C_1$-$C_6$ alkyl or $R^{1a}$ and $R^{1b}$ together form an optionally substituted $C_3$-$C_6$ cycloalkyl ring, or $R^{1c}$ and $R^{1d}$ together form an optionally substituted $C_3$-$C_6$ cycloalkyl ring;

A is a 5 membered nitrogen-containing aromatic ring and is substituted with at least one optionally substituted 5 to 10 membered monocyclic or bicyclic heteroaryl or aryl ring attached through an optional linker.

In one embodiment, A is substituted with -$Q^1$-B and (-$Q^2$-(D)$_m$)$_n$;

m represents 0 or 1;
n represents 0, 1 or 2;

$Q^1$ represents a covalent bond, an oxygen atom, a sulphur atom, —$OR^4$—, —SO—, —$SO_2$—, —C(O)—, —C(O)O—, —$C_0$-$C_3$-alkylene-C(O)$NR^2$—$C_0$-$C_3$ alkylene, —$C_0$-$C_3$-alkylene-$NR^2$—$C_0$-$C_3$-alkylene-, —$C_0$-$C_3$-alkylene-$NR^2$C(O)—$C_0$-$C_3$-alkylene, —$NR^2$C(O)$NR^3$—, —$SO_2NR^2$—, $NR^2SO_2$—, —$NR^2SO_2NR^3$—, —$NR^2$C(O)O—, —$NR^2$C(O)$OR^4$—, optionally substituted —$C_1$-$C_6$ alkylene, or optionally substituted —$C_2$-$C_6$ alkenylene; B represents an optionally substituted 5 to 10 membered monocyclic or bicyclic aryl or heteroaryl ring;

$R^2$ and $R^3$ each independently represent hydrogen or optionally substituted $C_1$-$C_6$ alkyl;

$R^4$ represents optionally substituted $C_1$-$C_6$ alkylene;

each occurrence of $Q^2$ independently represents halogen, cyano, nitro, hydroxyl, —$SR^5$, —$NR^5R^6$, —$CONR^5R^6$, —$C_0$-$C_3$-alkylene-$NR^5COR^6$—, —$NR^5CONR^6R^{6a}$, —$COR^5$, —C(O)$OR^5$, —$SO_2R^5$, —$SO_2NR^5R^6$, —$NR^5SO_2R^6$, —$NR^5SO_2NR^6R^{6a}$, —$NR^5C(O)OR^6$, optionally substituted —$C_1$-$C_6$ alkyl, optionally substituted —$C_1$-$C_6$ alkoxy, optionally substituted —$C_2$-$C_6$ alkenyl, a covalent bond, an oxygen atom, a sulphur atom, —$OR^7$—, —SO—, —$SO_2$—, —CO—, —C(O)O—, —$C_0$-$C_3$-al-kylene-C(O)$NR^5$—$C_0$-$C_3$ alkylene, —$C_0$-$C_3$-alkylene-$NR^5$—$C_0$-$C_3$ alkylene, —$C_0$-$C_3$-alkylene-$NR^5$C(O)—$C_0$-$C_3$ alkylene, —$NR^5CONR^6$—, —$SO_2NR^5$—, $NR^5SO_2$—, —$NR^5SO_2NR^6$—, —$NR^5$C(O)O—, —$NR^5$C(O)$OR^7$—, optionally substituted $C_1$-$C_6$ alkylene, or optionally substituted —$C_2$-$C_6$ alkenylene;

each occurrence of D independently represents an optionally substituted 3 to 10 membered monocyclic or bicyclic heterocyclyl, heteroaryl, cycloalkyl or aryl ring;

$R^5$, $R^6$ and $R^{6a}$ each independently represent hydrogen or optionally substituted $C_1$-$C_6$ alkyl;

$R^7$ represents optionally substituted $C_1$-$C_6$ alkylene.

Ring A contains from 1 to 3 nitrogen atoms. In one embodiment, ring A contains one nitrogen atom. In one embodiment, ring A contains two nitrogen atoms. In another embodiment, ring A contains three nitrogen atoms. Preferably, ring A contains two nitrogen atoms.

Ring A may be selected from the following structures and tautomers thereof:

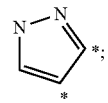

(IA)

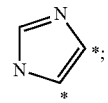

(IB)

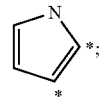

(IC)

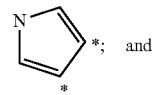

(ID)

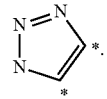

(IE)

In particular, the fused aromatic ring is:

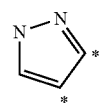

(IA)

or a tautomer thereof.

Wherein * represents the ring atoms shared with the cyanopyrrolidine core to form a 8 membered bicyclic ring. The ring may be substituted with -$Q^1$-B and (-$Q^2$-(D)$_m$)$_n$, wherein $Q^1$, $Q^2$, B, D, m and n are as defined herein.

In another aspect of the present invention there is provided a compound of formula II:

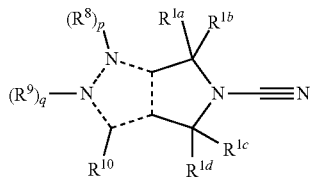

(II)

or a pharmaceutically acceptable salt thereof, wherein
˙˙˙˙˙˙˙ represent aromatic bonds;
$R^{1a}$, $R^{1b}$, $R^{1c}$ and $R^{1d}$ each independently represent hydrogen, optionally substituted $C_1$-$C_6$ alkyl or $R^{1a}$ and $R^{1b}$ together form an optionally substituted $C_3$-$C_6$ cycloalkyl ring, or $R^{1c}$ and $R^{1d}$ together form an optionally substituted $C_3$-$C_6$ cycloalkyl ring;
p is 0 or 1;
q is 0 or 1;
wherein when p and q are not both 0 and only one of p and q can be 1;
$R^8$ represents hydrogen, -$Q^1$-B or -$Q^2$-(D)$_m$;
$R^9$ represents hydrogen or optionally substituted $C_1$-$C_6$ alkyl;
$R^{10}$ represents hydrogen, -$Q^1$-B or -$Q^2$-(D)$_m$;
wherein one of $R^8$ or $R^{10}$ represents -$Q^1$-B;
$Q^1$ represents a covalent bond, an oxygen atom, a sulphur atom, —$OR^4$—, —SO—, —$SO_2$—, —C(O)—, —C(O)O—, —$C_0$-$C_3$-alkylene-C(O)$NR^2$—$C_0$-$C_3$-alkylene, —$C_0$-$C_3$-alkylene-$NR^2$—$C_0$-$C_3$-alkylene, —$C_0$-$C_3$-alkylene-$NR^2$C(O)—$C_0$-$C_3$-alkylene, —$NR^2$C(O)$NR^3$—, —$SO_2NR^2$—, $NR^2SO_2$—, —$NR^2SO_2NR^3$—, —$NR^2$C(O)O—, —$NR^2$C(O)$OR^4$—, optionally substituted —$C_1$-$C_6$ alkylene, or optionally substituted —$C_2$-$C_6$ alkenylene; B represents an optionally substituted 5 to 10 membered monocyclic or bicyclic aryl or heteroaryl ring;
$R^2$ and $R^3$ each independently represent hydrogen or optionally substituted $C_1$-$C_6$ alkyl;
$R^4$ represents optionally substituted $C_1$-$C_6$ alkylene;
$Q^2$ represents halogen, cyano, nitro, hydroxyl, —$SR^5$, —$NR^5R^6$, —$CONR^5R^6$, —$C_0$-$C_3$-alkylene-$NR^5COR^6$—, —$NR^5CONR^6R^{6a}$, —$COR^5$, —C(O)$OR^5$, —$SO_2R^5$, —$SO_2NR^5R^6$, —$NR^5SO_2R^6$, —$NR^5SO_2NR^6R^{6a}$, —$NR^5C(O)OR^6$, optionally substituted —$C_1$-$C_6$ alkyl, optionally substituted —$C_1$-$C_6$ alkoxy, optionally substituted —$C_2$-$C_6$ alkenyl, a covalent bond, an oxygen atom, a sulphur atom, —$OR^7$—, —SO—, —$SO_2$—, —CO—, —C(O)O—, —$C_0$-$C_3$-alkylene-C(O)$NR^5$—$C_0$-$C_3$-alkylene, —$C_0$-$C_3$-alkylene-$NR^5$—$C_0$-$C_3$-alkylene, —$C_0$-$C_3$-alkylene-$NR^5$C(O)—$C_0$-$C_3$-alkylene, —$NR^5CONR^6$—, —$SO_2NR^5$—, $NR^5SO_2$—, —$NR^5SO_2NR^6$—, —$NR^5$C(O)O—, —$NR^5$C(O)$OR^7$—, optionally substituted $C_1$-$C_6$ alkylene, or optionally substituted —$C_2$-$C_6$ alkenylene;
each occurrence of D independently represents an optionally substituted 3 to 10 membered monocyclic or bicyclic heterocyclyl, heteroaryl, cycloalkyl or aryl ring;
$R^5$, $R^6$ and $R^{6a}$ each independently represent hydrogen or optionally substituted $C_1$-$C_6$ alkyl;
$R^7$ represents optionally substituted $C_1$-$C_6$ alkylene.
In all cases described herein, $R^{1a}$, $R^{1b}$, $R^{1c}$ and $R^{1d}$ may each independently represent hydrogen, optionally substituted $C_1$-$C_6$ alkyl, or $R^{1a}$ together with $R^{1b}$ forms an optionally substituted $C_3$-$C_6$ cycloalkyl, or $R^{1c}$ and together with $R^{1d}$ form an optionally substituted $C_3$-$C_6$ cycloalkyl. In particular, $R^{1a}$, $R^{1b}$, $R^{1c}$ and $R^{1d}$ may each independently represent hydrogen or $C_1$-$C_3$ alkyl (e.g. methyl or ethyl). $R^{1a}$ may be hydrogen or $C_1$-$C_3$ alkyl and $R^{1b}$ may be hydrogen. $R^{1c}$ may be hydrogen or $C_1$-$C_3$ alkyl and $R^{1d}$ may be hydrogen. In particular, $R^{1a}$, $R^{1b}$, $R^{1c}$ and $R^{1d}$ each represent hydrogen. The alkyl within the definitions of $R^{1a}$, $R^{1b}$, $R^{1c}$ and $R^{1d}$ may be unsubstituted or substituted with one or more substituents selected from halogen, hydroxyl, thiol, cyano, amino, amido, nitro and $SF_5$. In particular, the alkyl may be substituted with fluorine.

$R^{1a}$ may represent hydrogen. $R^{1a}$ may represent $C_1$-$C_6$ alkyl. $R^{1a}$ may represent $C_1$-$C_3$ alkyl, for example, methyl or ethyl. When $R^{1a}$ represents $C_1$-$C_6$ alkyl, $R^{1b}$, $R^{1c}$ and $R^{1d}$ may each represent hydrogen. The alkyl within the definition of $R^{1a}$ may be unsubstituted or substituted with one or more substituents selected from halogen, hydroxyl, thiol, cyano, amino, amido, nitro and $SF_5$. In particular, the alkyl may be substituted with fluorine.

$R^{1b}$ may represent hydrogen. $R^{1b}$ may represent $C_1$-$C_6$ alkyl. $R^{1b}$ may represent $C_1$-$C_3$ alkyl, for example, methyl or ethyl. When $R^{1b}$ represents $C_1$-$C_6$ alkyl, $R^{1a}$, $R^{1c}$ and $R^{1d}$ may each represent hydrogen. The alkyl within the definition of $R^{1b}$ may be unsubstituted or substituted with one or more substituents selected from halogen, hydroxyl, thiol, cyano, amino, amido, nitro and $SF_5$. In particular, the alkyl may be substituted with fluorine.

$R^{1c}$ may represent hydrogen. $R^{1c}$ may represent $C_1$-$C_6$ alkyl. $R^{1c}$ may represent $C_1$-$C_3$ alkyl, for example, methyl or ethyl. When $R^{1c}$ represents $C_1$-$C_6$ alkyl, $R^{1a}$, $R^{1b}$ and $R^{1d}$ may each represent hydrogen. The alkyl within the definition of $R^{1c}$ may be unsubstituted or substituted with one or more substituents selected from halogen, hydroxyl, thiol, cyano, amino, amido, nitro and $SF_5$. In particular, the alkyl may be substituted with fluorine.

$R^{1d}$ may represent hydrogen. $R^{1d}$ may represent $C_1$-$C_6$ alkyl. $R^{1d}$ may represent $C_1$-$C_3$ alkyl, for example, methyl or ethyl. When $R^{1d}$ represents $C_1$-$C_6$ alkyl, $R^{1a}$, $R^{1b}$ and $R^{1c}$ may each represent hydrogen. The alkyl within the definition of $R^{1d}$ may be unsubstituted or substituted with one or more substituents selected from halogen, hydroxyl, thiol, cyano, amino, amido, nitro and $SF_5$. In particular, the alkyl may be substituted with fluorine.

Alternatively, $R^{1a}$ and $R^{1c}$ may together form a cycloalkyl ring. In addition, or alternatively, $R^{1c}$ and $R^{1d}$ may together form a cycloalkyl ring. When $R^{1a}$ and $R^{1b}$ together form a cycloalkyl ring, $R^{1c}$ and $R^{1d}$ may each independently represent hydrogen or optionally substituted $C_1$-$C_6$ alkyl. When $R^{1c}$ and $R^{1d}$ together form a cycloalkyl ring, $R^{1a}$ and $R^{1b}$ may each independently represent hydrogen or optionally substituted $C_1$-$C_6$ alkyl. The cycloalkyl ring within the definitions of $R^{1a}$, $R^{1b}$, $R^{1c}$ and $R^{1d}$ can contain 3, 4, 5, or 6 carbon ring atoms, in particular 3 or 4 carbon ring atoms. The cycloalkyl ring is attached to the cyanopyrrolidine core as a spiro ring, i.e. they share one ring atom. The cycloalkyl ring may be unsubstituted or substituted with a substituent selected from $C_1$-$C_3$ alkyl, $C_1$-$C_3$ alkoxy, halogen, hydroxyl, thiol, cyano, amino, amido, nitro and $SF_5$, wherein the alkyl and alkoxy may be optionally substituted with halogen.

The compounds may be in the form where $R^{1a}$, $R^{1b}$, $R^{1c}$ and $R^{1d}$ are each hydrogen. In such cases the compounds may be of the formula:

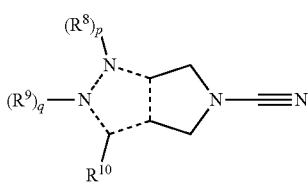

(IIA)

or a pharmaceutically acceptable salt thereof, wherein
- - - - - - represent aromatic bonds;
p is 0 or 1;
q is 0 or 1;
wherein p and q are not both 0 and only one of p and q can be 1;
$R^8$ represents hydrogen, $-Q^1$-B or $-Q^2$-$(D)_m$;
$R^9$ represents hydrogen or optionally substituted $C_1$-$C_6$ alkyl;
$R^{10}$ represents hydrogen, $-Q^1$-B or $-Q^2$-$(D)_m$;
wherein one of $R^8$ or $R^{10}$ represents $-Q^1$-B;
$Q^1$ represents a covalent bond, an oxygen atom, a sulphur atom, —$OR^4$—, —SO—, —$SO_2$—, —C(O)—, —C(O)O—, —$C_0$-$C_3$-alkylene-C(O)$NR^2$—$C_0$-$C_3$-alkylene, —$C_0$-$C_3$-alkylene-$NR^2$—$C_0$-$C_3$-alkylene, —$C_0$-$C_3$-alkylene-$NR^2$C(O)—$C_0$-$C_3$-alkylene, —$NR^2$C(O)$NR^3$—, —$SO_2NR^2$—, $NR^2SO_2$—, —$NR^2SO_2NR^3$—, —$NR^2$C(O)O—, —$NR^2$C(O)$OR^4$—, optionally substituted —$C_1$-$C_6$ alkylene, or optionally substituted —$C_2$-$C_6$ alkenylene; B represents an optionally substituted 5 to 10 membered monocyclic or bicyclic aryl or heteroaryl ring;
$R^2$ and $R^3$ each independently represent hydrogen or optionally substituted $C_1$-$C_6$ alkyl;
$R^4$ represents optionally substituted $C_1$-$C_6$ alkylene;
$Q^2$ represents halogen, cyano, nitro, hydroxyl, —$SR^5$, —$NR^5R^6$, —$CONR^5R^6$, —$C_0$-$C_3$-alkylene-$NR^5COR^6$—, —$NR^5CONR^6R^{6a}$, —$COR^5$, —C(O)$OR^5$, —$SO_2R^5$, —$SO_2NR^5R^6$, —$NR^5SO_2R^6$, —$NR^5SO_2NR^6R^{6a}$, —$NR^5$C(O)$OR^6$, optionally substituted —$C_1$-$C_6$ alkyl, optionally substituted —$C_1$-$C_6$ alkoxy, optionally substituted —$C_2$-$C_6$ alkenyl, a covalent bond, an oxygen atom, a sulphur atom, —$OR^7$—, —SO—, —$SO_2$—, —CO—, —C(O)O—, —$C_0$-$C_3$-alkylene-C(O)$NR^5$—$C_0$-$C_3$ alkylene, —$C_0$-$C_3$-alkylene-$NR^5$—$C_0$-$C_3$ alkylene, —$C_0$-$C_3$-alkylene-$NR^5$C(O)—$C_0$-$C_3$ alkylene, —$NR^5CONR^5$—, —$SO_2NR^5$—, $NR^5SO_2$—, —$NR^5SO_2NR$—, —$NR^5$C(O)O—, —$NR^5$C(O)$OR^7$—, optionally substituted $C_1$-$C_6$ alkylene, or optionally substituted —$C_2$-$C_6$ alkenylene;
each occurrence of D independently represents an optionally substituted 3 to 10 membered monocyclic or bicyclic heterocyclyl, heteroaryl, cycloalkyl or aryl ring;
$R^5$ and $R^6$ each independently represent hydrogen or optionally substituted $C_1$-$C_6$ alkyl;
$R^7$ represents optionally substituted $C_1$-$C_6$ alkylene.

In all cases described herein, p is 0 or 1 and q is 0 or 1 wherein p and q are not both 0 and only one of p and q is 1, i.e. p and q cannot both be 1.

In one embodiment, p is 1 and q is 0.

When p is 1 and q is 0, $R^8$ may represent $-Q^1$-B, wherein $Q^1$ and B are as defined herein and $R^{10}$ may be hydrogen or $-Q^2$-$(D)_m$ wherein m is 0 or 1 and $Q^2$ and D are as defined herein. In one embodiment, $R^{10}$ may be hydrogen or $-Q^2$-$(D)_m$ wherein m is 0 and $Q^2$ is as defined herein. In another embodiment, $R^{10}$ may be $-Q^2$-$(D)_m$ wherein m is 1 and $Q^2$ and D are as defined herein.

Alternatively, when p is 1 and q is 0, $R^8$ may represent hydrogen or $-Q^2$-$(D)_m$ wherein m is 0 or 1 and $Q^2$ and D are as defined herein and $R^{10}$ represents $-Q^1$-B wherein $Q^1$ and B are as defined herein. In one embodiment, $R^8$ may represent hydrogen or $-Q^2$-$(D)_m$ wherein m is 0 and $Q^2$ is as defined herein. In another embodiment, $R^8$ may represent $-Q^2$-$(D)_m$ wherein m is 1 and $Q^2$ and D are as defined herein.

In another embodiment, p is 0 and q is 1.

When p is 0 and q is 1, $R^9$ represents hydrogen or optionally substituted $C_1$-$C_6$ alkyl and $R^{10}$ represents $-Q^1$-B wherein $Q^1$ and B are as defined herein. The alkyl may be substituted with halogen, hydroxyl, thiol, cyano, amino, amido, nitro or $SF_5$. In particular, $R^9$ is hydrogen or methyl. More particularly, $R^9$ is methyl.

In all cases described herein, $Q^1$ may be selected from a covalent bond, an oxygen atom, a sulphur atom, —$OR^4$—, —SO—, —$SO_2$—, —C(O)—, —C(O)O—, —$C_0$-$C_3$-alkylene-C(O)$NR^2$—$C_0$-$C_3$-alkylene, —$C_0$-$C_3$-alkylene-$NR^2$—$C_0$-$C_3$-alkylene (e.g. methylamino), —$C_0$-$C_3$-alkylene-$NR^2$C(O)—$C_0$-$C_3$-alkylene, —$NR^2$C(O)$NR^3$—, —$SO_2NR^2$—, $NR^2SO_2$—, —$NR^2SO_2NR^3$—, —$NR^2$C(O)O—, —$NR^2$C(O)$OR^4$—, optionally substituted —$C_1$-$C_6$ alkylene (e.g. methylene or ethylene) or optionally substituted —$C_2$-$C_6$ alkenylene (e.g. vinyl).

$R^2$ and $R^3$ each independently represent hydrogen or $C_1$-$C_6$ alkyl, $C_1$-$C_4$ alkyl, or $C_1$-$C_2$ alkyl. The alkyl may be optionally substituted with halogen, hydroxyl, thiol, cyano, amino, amido, nitro or $SF_5$.

$R^4$ represents $C_1$-$C_6$ alkylene, $C_1$-$C_4$ alkylene or $C_1$-$C_2$ alkylene. The alkylene may be optionally substituted with halogen, hydroxyl, thiol, cyano, amino, amido, nitro or $SF_5$.

In particular, $Q^1$ may be selected from a covalent bond, —$C_0$-$C_3$ alkylene-$NR^2$C(O)—$C_0$-$C_3$ alkylene, —$C_0$-$C_3$-alkylene-$NR^2$—$C_0$-$C_3$-alkylene or optionally substituted —$C_1$-$C_6$ alkylene, and $R^2$ represents hydrogen or $C_1$-$C_3$ alkyl wherein the alkyl may be unsubstituted or substituted with halogen, hydroxyl, thiol, cyano, amino, amido, nitro and $SF_5$.

In one embodiment, $Q^1$ is selected from a covalent bond, $C_1$ alkylene-NHC(O)—, —NH—, methylene or methylene-NHC(O)-methylene. In another embodiment, $Q^1$ is a covalent bond.

In all cases described herein, B represents an optionally substituted 5 to 10 membered (e.g. 5, 6, 7, 8, 9, or 10 membered) monocyclic or bicyclic aryl or heteroaryl ring.

B may represents an optionally substituted 5 or 6 membered monocyclic aryl or heteroaryl ring.

Alternatively, B may represent an optionally substituted 9 or 10 membered bicyclic aryl or heteroaryl ring.

B may be selected from naphthyl, naphthalenyl, pyridinyl, pyrazinyl, pyrimidinyl, pyridazinyl, furyl, pyrrolyl, oxazolyl, thiazolyl, pyrazolyl, tetrazolyl, indolyl, indolizinyl, isoindolyl, indolinyl, purinyl, furazanyl, imidazolyl, indazolyl, isothiazolyl, isoxazolyl, oxadiazolyl, tetrazolyl, thiadiazolyl, benzofuranyl, isobenzofuranyl, benzothiophenyl, isobenzothiophenyl, benzimidazolyl, benzothiazolyl, napthyridinyl, pteridinyl, pyrazinyl, quinolinyl, isoquinolinyl, cinnolinyl, phthalazinyl, quinazolinyl, imidazopyridinyl, pyrazolopyridinyl, thiazolopyridinyl, isoindolinyl, triazinyl, dihydrophyridinyl, quinoxalinyl, dihydrobenzoxazinyl and dihydropyrrolopyridinyl.

In particular, B is selected from phenyl, quinolinyl, pyridinyl, pyrazolyl, indazolyl, imidazolyl and isoquinolinyl. More particularly, B is phenyl.

When p is 1, and $R^8$ represents $-Q^1$-B, B may be selected from phenyl, indazolyl or pyrazolyl. In particular, B may be indazolyl.

In all cases described herein, B may be unsubstituted or substituted with one or more non-ring substituents and/or ring substituents.

Therefore, B may be unsubstituted or substituted with one or more (e.g. one, two three or four) substituents selected from halogen, cyano, oxo, nitro, hydroxyl, —$SR^{11}$, optionally substituted —$C_1$-$C_6$ alkyl, optionally substituted —$C_1$-$C_6$ alkoxy, optionally substituted —$C_2$-$C_6$ alkenyl, optionally substituted —$C_2$-$C_6$ alkynyl, -$Q^{3a}$-$R^{13}$, $Q^{3a}$-O-$Q^{3b}$-$R^{13}$, $Q^{3a}$-S-$Q^{3b}$-$R^{13}$, $Q^{3a}$-SO-$Q^{3b}$-$R^{13}$, $Q^{3a}$—$NR^{11}CONR^{12}R^{12a}$, $Q^{3a}$-$NR^{11}CONR^{12}$-$Q^{3a}$-$R^{13}$, -$Q^{3a}$-$NR^{11}R^{12}$, -$Q^{3a}$-$NR^{11}$-$Q^{3b}$-$R^{13}$, $Q^{3a}$-$COR^{11}$, -$Q^{3a}$-CO-$Q^{3b}$-$R^{13}$, $Q^{3a}$-$NR^{11}COR^{12}$, -$Q^{3a}$-$NR^{11}$CO-$Q^{3b}$-$R^{13}$, -$Q^{3a}$-$NR^{11}$C(O)$OR^{12}$, -$Q^{3a}$-$NR^{11}$C(O)O-$Q^{3b}$-$R^{13}$, -$Q^{3a}$-$SO_2R^{11}$, -$Q^{3a}$-$SO_2$-$Q^{3b}$-$R^{13}$, -$Q^{3a}$-$CONR^{11}R^{12}$, -$Q^{3a}$-$CONR^{11}$-$Q^{3b}$-$R^{13}$, -$Q^{3a}$-$CO_2R^{11}$, -$Q^{3a}$-$CO_2$-$Q^{3b}$-$R^{13}$, -$Q^{3a}$-$SO_2NR^{11}R^{12}$, -$Q^{3a}$-$SO_2NR^{11}$-$Q^{3b}$-$R^{13}$, -$Q^{3a}$-$NR^{11}SO_2R^{12}$, -$Q^{3a}$-$NR^{11}SO_2$-$Q^{3b}$-$R^{13}$ and -$Q^{3a}$-$NR^{11}SO_2NR^{12}R^{12a}$, -$Q^{3a}$-$NR^{11}SO_2NR^{12}$-$Q^{3b}$-$R^{13}$.

$Q^{3a}$ and $Q^{3b}$ each independently represent a covalent bond, $C_1$-$C_6$ alkylene, $C_1$-$C_4$ alkylene, $C_1$-$C_2$ alkylene or $C_2$-$C_6$ alkenylene or $C_2$-$C_4$ alkenylene. The alkylene or alkenylene may be substituted with halogen, hydroxyl, thiol, cyano, amino, amido, nitro or $SF_5$.

$R^{11}$, $R^{12}$ and $R^{12a}$ each independently represent hydrogen or $C_1$-$C_6$ alkyl, $C_1$-$C_4$ alkyl or $C_1$-$C_2$ alkyl. The alkyl may be substituted with halogen, hydroxyl, thiol, cyano, amino, amido, nitro or $SF_5$.

$R^{13}$ represents optionally substituted heterocyclyl, optionally substituted heteroaryl, optionally substituted aryl, or an optionally substituted cycloalkyl.

The non-ring substituents may be selected from halogen, cyano, oxo, nitro, hydroxyl, —$SR^{11}$, optionally substituted —$C_1$-$C_6$ alkyl, optionally substituted —$C_1$-$C_6$ alkoxy, optionally substituted —$C_2$-$C_6$ alkenyl, optionally substituted —$C_2$-$C_6$ alkynyl, -$Q^{3a}$-$NR^{11}CONR^{12}R^{12a}$, -$Q^{3a}$-$NR^{11}R^{12}$, -$Q^{3a}$-$COR^{11}$, -$Q^{3a}$-$NR^{11}COR^{12}$, -$Q^{3a}$-$NR^{11}$C(O)$OR^{12}$, -$Q^{3a}$-$SO_2R^{11}$, -$Q^{3a}$-$CONR^{11}R^{12}$, -$Q^{3a}$-$CO_2R^{11}$, -$Q^{3a}$-$SO_2NR^{11}R^{12}$, -$Q^{3a}$-$NR^{11}SO_2R^{12}$ and -$Q^{3a}$-$NR^{11}SO_2NR^{12}R^{12a}$.

In addition to the non-ring substituents, or alternatively, B may be substituted with one or more, in particular only one, ring substituents which may be selected from -$Q^{3a}$-$R^{13}$, $Q^{3a}$-O-$Q^{3b}$-$R^{13}$, -$Q^{3a}$-S-$Q^{3b}$-$R^{13}$, -$Q^{3a}$-SO-$Q^{3b}$-$R^{13}$, -$Q^{3a}$-$NR^{11}CONR^{12}$-$Q^{3a}$-$R^{13}$, $Q^{3a}$-$NR^{11}$-$Q^{3b}$-$R^{13}$, -$Q^{3a}$-CO-$Q^{3b}$-$R^{13}$, -$Q^{3a}$-$NR^{11}$CO-$Q^{3b}$-$R^{13}$, -$Q^{3a}$-$NR^{11}$C(O)O-$Q^{3b}$-$R^{13}$, -$Q^{3a}$-$SO_2$-$Q^{3b}$-$R^{13}$, -$Q^{3a}$-$CONR^{11}$-$Q^{3b}$-$R^{13}$, -$Q^{3a}$-$CO_2$-$Q^{3b}$-$R^{13}$, -$Q^{3a}$-$SO_2NR^{11}$-$Q^{3b}$-$R^{13}$, -$Q^{3a}$-$NR^{11}SO_2$-$Q^{3b}$-$R^{13}$ and -$Q^{3a}$-$NR^{11}SO_2NR^{12}$-$Q^{3b}$-$R^{13}$.

B may be substituted with one or more substituents selected from halogen, cyano, optionally substituted $C_1$-$C_6$ alkyl, optionally substituted $C_1$-$C_6$ alkoxy, -$Q^{3a}$-$R^{13}$, -$Q^{3a}$-O-$Q^{3b}R^{13}$, -$Q^{3a}$-$CONR^{11}R^{12}$, -$Q^{3a}$-$CONR^{11}$-$Q^{3b}$-$R^{12}$, -$Q^{3a}$-$NR^{11}$CO-$Q^{3b}$-$R^{13}$, -$Q^{3a}$-$SO_2NR^{11}R^{12}$, -$Q^{3a}$-$SO_2NR^{11}$-$Q^{3b}$-$R^{13}$ and -$Q^{3a}$-$NR^{11}SO_2$-$Q^{3b}$-$R^{13}$.

In particular, $Q^{3a}$ is a covalent bond or optionally substituted $C_1$-$C_3$ alkylene. $Q^{3a}$ may be a covalent bond, methylene or ethylene.

In particular $Q^{3b}$ is a covalent bond or optionally substituted $C_1$-$C_3$ alkylene. $Q^{3b}$ may be a covalent bond, methylene or ethylene.

In particular, $R^{11}$, $R^{12}$ and $R^{12a}$ each independently represent hydrogen or optionally substituted $C_1$-$C_3$ alkyl. The optional substituents for the alkyl may be selected from halogen, hydroxyl, thiol, cyano, amino, amido, nitro and $SF_5$. In particular the optional substituents are selected from fluorine.

$R^{13}$ may be an optionally substituted 3 to 10 membered monocyclic or bicyclic heterocyclyl, heteroaryl, cycloalkyl or aryl ring. $R^{13}$ may be a 3 to 6 membered ring. Alternatively, $R^{13}$ may be a 9 or 10 membered ring.

$R^{13}$ may be substituted with further optionally substituted 3 to 10 membered heterocyclyl, heteroaryl, aryl or cycloalkyl rings, either directly attached or via linking group. The linking group may be an oxygen, a carbonyl or an optionally substituted $C_1$-$C_6$ alkylene chain. The linking group may be oxygen, —CO— or a $C_1$-$C_6$ alkylene group. In one embodiment the linking group may be a carbonyl, or an alkylene chain, for example, —CO— or a $C_1$-$C_3$ alkylene group.

In particular, $R^{13}$ is unsubstituted or substituted with one or more substituents selected from halogen, hydroxyl, thiol, cyano, amino, amido, nitro, $SF_5$, $C_1$-$C_3$ alkyl or $C_1$-$C_3$ alkoxy wherein the alkyl or alkoxy may be optionally substituted with hydroxyl, thiol, cyano, amino, amido, nitro or $SF_5$, in particular the substituent is $C_1$-$C_3$ alkyl. In one embodiment, $R^{13}$ is unsubstituted. More particularly, $R^{13}$ is an unsubstituted or substituted monocyclic 3 or 6 membered heterocyclyl, heteroaryl, cycloalkyl or aryl ring. The ring may be unsubstituted or substituted with halogen, hydroxyl, thiol, cyano, amino, amido, nitro, $SF_5$, $C_1$-$C_3$ alkyl or $C_1$-$C_3$ alkoxy wherein the alkyl or alkoxy may be optionally substituted with hydroxyl, thiol, cyano, amino, amido, nitro or $SF_5$. More particularly, $R^{13}$ is unsubstituted or monosubstituted. More particularly, $R^{13}$ is unsubstituted or substituted with $C_1$-$C_3$ alkyl.

$R^{13}$ may be an optionally substituted 3 to 6 membered monocyclic heterocyclyl, heteroaryl, cycloalkyl or aryl ring. $R^{13}$ may be selected from phenyl, pyridinyl, piperazinyl and cyclopropyl. In particular, $R^{13}$ may be selected from phenyl or cyclopropyl.

The optional substituents for the alkyl and alkoxy within the definitions of B and $R^{11}$, $R^{12}$ and $R^{12a}$ may be selected from halogen, hydroxyl, thiol, cyano, amino, amido, nitro and $SF_5$. In particular, the optional substituents are fluorine.

More particularly, B may be substituted with one or more substituents selected from fluorine; chlorine; cyano; methyl; propyl; $CF_3$; methoxy; propoxy; $OCF_3$; —$C(O)NH_2$, —$C(O)NHCH_3$, —$C(O)N(CH_3)_2$ (i.e. -$Q^{3a}$-$C(O)R^{11}R^{12}$ wherein $Q^{3a}$ is a covalent bond and $R^{11}$ and $R^{12}$ are each independently hydrogen or methyl); —$SO_2N(CH_3)_2$ (i.e. -$Q^{3a}$-$SO_2NR^{11}R^{12}$ wherein $Q^{3a}$ is a covalent bond and $R^{11}$ and $R^{12}$ are both methyl); —$R^{13}$, methylene-$R^{13}$ (i.e. -$Q^{3a}$-$R^{13}$ wherein $Q^{3a}$ is a covalent bond or methylene); —C(O)NH—$R^{13}$ (e. -$Q^{3a}$-$C(O)NR^{11}$-$Q^{3b}$-$R^{13}$ where $Q^{3a}$ and $Q^{3b}$ both represent a covalent bond and $R^{11}$ is hydrogen); —C(O)NH-methylene-$R^{13}$ (e. -$Q^{3a}$-$C(O)NR^{11}$-$Q^{3b}$-$R^{13}$ wherein $Q^{3a}$ is a covalent bond, $Q^{3b}$ is methylene and $R^{11}$ is hydrogen); —NHC(O)—$C_2$ alkylene-$R^{13}$ (i.e. -$Q^{3a}$-$NR^{11}C(O)$-$Q^{3b}$-$R^{13}$ where $Q^{3a}$ is a covalent bond, $Q^{3b}$ is $C_2$ alkylene and $R^{11}$ is hydrogen); —C(O)NH— ethylene-$R^{13}$ (e. -$Q^{3a}$-$C(O)NR^{11}$-$Q^{3b}$-$R^{13}$ where $Q^{3a}$ is a covalent bond, $Q^{3b}$ is ethylene and $R^{11}$ is hydrogen; —O-methylene-$R^{13}$, —O—$R^{13}$ (i.e. -$Q^{3a}$-O-$Q^{3b}$-$R^{13}$ where $Q^{3a}$ is a covalent bond and $Q^{3b}$ is methylene or a covalent bond), —C(O)—$R^{13}$ (i.e. -$Q^{3a}$-$C(O)$-$Q^{3b}$-$R^{13}$ where $Q^{3a}$ and $Q^{3b}$ both represent a covalent bond), —$SO_2NH$—$R^{13}$ (i.e. -$Q^{3a}$-$SO_2NR^{11}$-$Q^{3b}$-$R^{13}$ where $Q^{3a}$ and $Q^{3b}$ both represent a covalent bond and $R^{11}$ is hydrogen), —$NHSO_2$—$R^{13}$ (i.e. $Q^{3a}$-$NR^{11}SO_2$-$Q^{3b}$-$R^{13}$ where $Q^{3a}$ and $Q^{3b}$ both represent a covalent bond and $R^{11}$ is hydrogen), wherein $R^{13}$ is selected from phenyl, pyridinyl, piperazinyl and cyclopropyl.

When p is 1 and $R^8$ represents -$Q^1$-B, B may be unsubstituted or substituted with halogen, $C_1$-$C_6$ alkoxy, —$CONR^{11}R^{12}$ or -$Q^{3a}$-$R^{13}$, wherein $R^{11}$, $R^{12}$, $R^{13}$ and $Q^{3a}$ are as defined herein. In particular, B may be substituted with fluorine, methyl, methoxy, —C(O)NH$_2$, —C(O)NHMe, Q$^{3a}$-phenyl wherein Q$^{3a}$ is a covalent bond or —CONH—C$_1$-C$_2$ alkylene. In one embodiment, B is unsubstituted or substituted with Q$^{3a}$-phenyl wherein Q$^{3a}$ is —CONH—C$_1$ alkylene.

In one embodiment, B is unsubstituted, mono-substituted, di-substituted or tri-substituted. In particular, B is unsubstituted, mono-substituted or di-substituted. For example, B is unsubstituted or mono-substituted. In some embodiments, B is unsubstituted.

In certain instances, B is selected from phenyl, naphthyl, naphthalenyl, pyridinyl, pyrazinyl, pyrimidinyl, pyridazinyl, furyl, pyrrolyl, oxazolyl, thiazolyl, pyrazolyl, tetrazolyl, indolyl, indolizinyl, isoindolyl, indolinyl, purinyl, furazanyl, imidazolyl, indazolyl, isothiazolyl, isoxazolyl, oxadiazolyl, tetrazolyl, thiadiazolyl, benzofuranyl, isobenzofuranyl, benzothiophenyl, isobenzothiophenyl, benzimidazolyl, benzothiazolyl, napthyridinyl, pteridinyl, pyrazinyl, quinolinyl, isoquinolinyl, cinnolinyl, phthalazinyl, quinazolinyl, imidazopyridinyl, pyrazolopyridinyl, thiazolopyridinyl, isoindolinyl, triazinyl, dihydrophyridinyl, quinoxalinyl, dihydrobenzoxazinyl, dihydropyrrolopyridinyl which is either unsubstituted or substituted with one or more substituents selected from halogen, cyano, oxo, nitro, hydroxyl, —SR$^{11}$, optionally substituted —C$_1$-C$_6$ alkyl, optionally substituted —C$_1$-C$_6$ alkoxy, optionally substituted —C$_2$-C$_6$ alkenyl, optionally substituted —C$_2$—C$_6$ alkynyl, -Q$^{3a}$-R$^{13}$, -Q$^{3a}$-O-Q$^{3b}$-R$^{13}$, -Q$^{3a}$-S-Q$^{3b}$-R$^{13}$, -Q$^{3a}$-SO-Q$^{3b}$-R$^{13}$, -Q$^{3a}$-NR$^{11}$CONR$^{12}$R$^{12a}$, -Q$^{3a}$-NR$^{11}$CONR$^{12}$-Q$^{3a}$-R$^{13}$, -Q$^{3a}$-NR$^{11}$R$^{12}$, -Q$^{3a}$-NR$^{11}$-Q$^{3b}$-R$^{13}$, -Q$^{3a}$-COR$^{11}$, -Q$^{3a}$-CO-Q$^{3b}$-R$^{13}$, -Q$^{3a}$-NR$^{11}$COR$^{12}$, -Q$^{3a}$-NR$^{11}$CO-Q$^{3b}$-R$^{13}$, -Q$^{3a}$-NR$^{11}$C(O)OR$^{12}$, -Q$^{3a}$-NR$^{11}$C(O)O-Q$^{3b}$-R$^{13}$, -Q$^{3a}$-SO$_2$R$^{11}$, -Q$^{3a}$-SO$_2$-Q$^{3b}$-R$^{13}$, -Q$^{3a}$-CONR$^{11}$R$^{12}$, -Q$^{3a}$-CONR$^{11}$-Q$^{3b}$-R$^{13}$, -Q$^{3a}$-CO$_2$R$^{11}$, -Q$^{3a}$-CO$_2$-Q$^{3b}$-R$^{13}$, -Q$^{3a}$-SO$_2$NR$^{11}$R$^{12}$, -Q$^{3a}$-SO$_2$NR$^{11}$-Q$^{3b}$-R$^{13}$, -Q$^{3a}$-NR$^{11}$SO$_2$R$^{12}$, -Q$^{3a}$-NR$^{11}$SO$_2$-Q$^{3b}$-R$^{13}$ and -Q$^{3a}$-NR$^{11}$SO$_2$NR$^{12}$R$^{12a}$, -Q$^{3a}$-NR$^{11}$SO$_2$NR$^{12}$-Q$^{3b}$-R$^{13}$; wherein Q$^{3a}$ and Q$^{3b}$ each independently represent a covalent bond, optionally substituted C$_1$-C$_6$ alkylene or optionally substituted C$_2$-C$_6$ alkenylene; R$^{11}$, R$^{12}$ and R$^{12a}$ each independently represent hydrogen or optionally substituted C$_1$-C$_6$ alkyl; and R$^{13}$ represents optionally substituted heterocyclyl, optionally substituted heteroaryl, optionally substituted aryl, or an optionally substituted cycloalkyl.

B may represent a ring selected from phenyl, quinolinyl, pyridinyl, pyrazolyl, indazolyl, imidazolyl and isoquinolinyl which may be unsubstituted or substituted with one or more substituents selected from halogen, cyano, oxo, nitro, hydroxyl, —SR$^{11}$, optionally substituted —C$_1$-C$_6$ alkyl, optionally substituted —C$_1$-C$_6$ alkoxy, optionally substituted —C$_2$-C$_6$ alkenyl, optionally substituted —C$_2$-C$_6$ alkynyl, -Q$^{3a}$-R$^{13}$, -Q$^{3a}$-O-Q$^{3b}$-R$^{13}$, -Q$^{3a}$-S-Q$^{3b}$-R$^{13}$, -Q$^{3a}$-SO-Q$^{3b}$-R$^{13}$, -Q$^{3a}$-NR$^{11}$CONR$^{12}$R$^{12a}$, -Q$^{3a}$-NR$^{11}$CONR$^{12}$-Q$^{3a}$-R$^{13}$, -Q$^{3a}$-NR$^{11}$R$^{12}$, -Q$^{3a}$-NR$^{11}$-Q$^{3b}$-R$^{13}$, -Q$^{3a}$-COR$^{11}$, -Q$^{3a}$-CO-Q$^{3b}$-R$^{13}$, -Q$^{3a}$-NR$^{11}$COR$^{12}$, -Q$^{3a}$-NR$^{11}$CO-Q$^{3b}$-R$^{13}$, -Q$^{3a}$-NR$^{11}$C(O)OR$^{12}$, -Q$^{3a}$-NR$^{11}$C(O)O-Q$^{3b}$-R$^{13}$, -Q$^{3a}$-SO$_2$R$^{11}$, -Q$^{3a}$-SO$_2$-Q$^{3b}$-R$^{13}$, -Q$^{3a}$-CONR$^{11}$R$^{12}$, -Q$^{3a}$-CONR$^{11}$-Q$^{3b}$-R$^{13}$, -Q$^{3a}$-CO$_2$R$^{11}$, -Q$^{3a}$-CO$_2$-Q$^{3b}$-R$^{13}$, -Q$^{3a}$-SO$_2$NR$^{11}$R$^{12}$, -Q$^{3a}$-SO$_2$NR$^{11}$-Q$^{3b}$-R$^{13}$, -Q$^{3a}$-NR$^{11}$SO$_2$R$^{12}$, -Q$^{3a}$-NR$^{11}$SO$_2$-Q$^{3b}$-R$^{13}$ and -Q$^{3a}$-NR$^{11}$SO$_2$NR$^{12}$R$^{12a}$, -Q$^{3a}$-NR$^{11}$SO$_2$NR$^{12}$-Q$^{3b}$-R$^{13}$; wherein Q$^{3a}$ and Q$^{3b}$ each independently represent a covalent bond, optionally substituted C$_1$-C$_6$ alkylene or optionally substituted C$_2$-C$_6$ alkenylene; R$^{11}$, R$^{12}$ and R$^{12a}$ each independently represent hydrogen or optionally substituted C$_1$-C$_6$ alkyl; and R$^{13}$ represents optionally substituted heterocyclyl, optionally substituted heteroaryl, optionally substituted aryl, or an optionally substituted cycloalkyl.

B may represent a ring selected from quinolinyl, pyridinyl, pyrazolyl, indazolyl, imidazolyl and isoquinolinyl which may which may unsubstituted or substituted with one or more (e.g. one, two or three) substituents selected from fluorine, chlorine, cyano, methyl, propyl, CF$_3$, methoxy, propoxy, OCF$_3$, —C(O)NH$_2$, —C(O)NHCH$_3$, —C(O)N(CH$_3$)$_2$, —SO$_2$N(CH$_3$)$_2$, —R$^{13}$, —C(O)NH—R$^{13}$, —C(O)NH— methylene-R$^{13}$, —C(O)NH-ethylene-R$^{13}$, —O-methylene-R$^{13}$, —O—R$^{13}$, —C(O)—R$^{13}$, methylene-R$^{13}$, —SO$_2$NH—R$^{13}$, —NHSO$_2$—R$^{13}$, wherein R$^{13}$ is selected from phenyl, pyridinyl, piperazinyl and cyclopropyl.

In all cases described here, Q$^2$ represents halogen, cyano, nitro, hydroxyl, —SR$^5$, —NR$^5$R$^6$, —CONR$^5$R$^6$, —C$_0$-C$_3$-alkylene-NR$^5$COR$^6$, —NR$^5$CONR$^6$R$^{6a}$, —COR$^5$, —C(O)OR$^5$, —SO$_2$R$^5$, —SO$_2$NR$^5$R$^6$, —NR$^5$SO$_2$R$^6$, —NR$^5$SO$_2$NR$^6$R$^{6a}$, —NR$^5$C(O)OR$^6$, optionally substituted —C$_1$-C$_6$ alkyl, optionally substituted C$_1$-C$_6$ alkoxy, optionally substituted —C$_2$-C$_6$ alkenyl, a covalent bond, an oxygen atom, a sulphur atom, —OR$^7$—, —SO—, —SO$_2$—, —CO—, —C(O)O—, —C$_0$-C$_3$-alkylene-C(O)NR—C$_0$-C$_3$ alkylene, —C$_0$-C$_3$-alkylene-NR$^5$—C$_0$-C$_3$ alkylene, —C$_0$-C$_3$-alkylene-NR$^5$C(O)—C$_0$-C$_3$ alkylene, —NR$^5$CONR$^6$—, —SO$_2$NR$^5$—, NR$^5$SO$_2$—, —NR$^5$SO$_2$NR$^6$—, —NR$^5$C(O)O—, —NR$^5$C(O)OR$^7$—, optionally substituted C$_1$-C$_6$ alkylene, or optionally substituted —C$_2$-C$_6$ alkenylene, wherein R$^5$, R$^6$ and R$^{6a}$ each independently represent hydrogen or optionally substituted C$_1$-C$_6$ alkyl and R$^7$ represents optionally substituted C$_1$-C$_6$ alkylene.

In particular, Q$^2$ represents optionally substituted C$_1$-C$_6$ alkyl, —C$_0$-C$_3$-alkylene-NR$^5$COR$^6$, a covalent bond, C$_1$-C$_6$ alkylene, —C$_0$-C$_3$-alkylene-NR$^5$—C$_0$-C$_3$ alkylene or —C$_0$-C$_3$-alkylene-NR$^5$C(O)—C$_0$-C$_3$ alkylene, wherein R$^5$ is hydrogen or C$_1$-C$_3$ alkyl.

In particular, Q$^2$ represents methyl, i-propyl, —NHC(O)CH$_3$, a covalent bond, methylene, —NH— or methylene-NR$^5$C(O)—.

When m is 1, D represents an optionally substituted 3 to 10 membered monocyclic or bicyclic heterocyclyl, heteroaryl, cycloalkyl or aryl ring (when m is 0, Q$^2$ is present and D is absent).

D may represent an optionally 5 or 6 membered monocyclic heterocyclyl, heteroaryl or aryl ring.

Alternatively, D may represent an optionally substituted 9 or 10 membered bicyclic heterocyclyl, heteroaryl or aryl ring.

D may be selected from cyclopropyl, cyclobutyl, cyclopentyl, cyclohexyl, cycloheptyl, cyclooctyl, decahydronaphthalenyl, phenyl, naphthyl, naphthalenyl, pyridinyl, pyrazinyl, pyrimidinyl, pyridazinyl, furyl, pyrrolyl, oxazolyl, thiazolyl, pyrazolyl, tetrazolyl, indolyl, indolizinyl, isoindolyl, indolinyl, purinyl, furazanyl, imidazolyl, indazolyl, isothiazolyl, isoxazolyl, oxadiazolyl, tetrazolyl, thiadiazolyl, benzofuranyl, isobenzofuranyl, benzothiophenyl, isobenzothiophenyl, benzimidazolyl, benzothiazolyl, napthyridinyl, pteridinyl, pyrazinyl, quinolinyl, isoquinolinyl, cinnolinyl, phthalazinyl, quinazolinyl, imidazopyridinyl, pyrazolopyridinyl, thiazolopyridinyl, isoindolinyl, triazinyl, dihydrophyridinyl, quinoxalinyl, dihydrobenzoxazinyl, dihydropyrrolopyridinyl, azetidinyl, pyrrolidinyl, piperidinyl, azepanyl, diazepanyl, dihydrofuranyl (e.g. 2,3-dihydrofuranyl, 2,5-dihydrofuranyl), dioxolanyl, morpholinyl, oxazolidinyl, oxazinanyl, indolinyl, isoindolinyl, piperazinyl, tetrahydrofuranyl, thiomorpholinyl, dihydropyranyl (e.g. 3,4-dihydropyranyl, 3,6-dihydropyranyl), homopiperazinyl, dioxanyl, hexahydropyrimidinyl, pyrazolinyl, pyrazolidinyl, 4H-quinolizinyl, quinuclidinyl, tetrahydropyranyl, tetrahydropyridinyl, tetrahydropyrimidinyl, tetrahydrothiophenyl, thiazolidinyl, benzopyranyl, tetrahydroquinolinyl, dihydrobenzoxazinyl and tetrahydroisoquinolinyl.

In particular, D is selected from phenyl, isoquinolinyl and pyridinyl. More particularly, D is phenyl.

In all cases described herein, D may be unsubstituted or substituted with one or more (e.g. one, two three or four) substituents selected from halogen, cyano, oxo, nitro, hydroxyl, —$SR^{14}$, optionally substituted —$C_1$-$C_6$ alkyl, optionally substituted —$C_1$-$C_6$ alkoxy, optionally substituted —$C_2$-$C_6$ alkenyl, optionally substituted —$C_2$-$C_6$ alkynyl, -$Q^{4a}R^{16}$, -$Q^{4a}$-O-$Q^{4b}$-$R^{16}$, -$Q^{4a}$-S-$Q^{4b}$-$R^{16}$, -$Q^{4a}$-SO-$Q^{4b}$-$R^{16}$, -$Q^{4a}$-$NR^{14}CONR^{15}R^{15a}$, -$Q^{4a}$-$NR^{14}CONR^{15}$-$Q^{4b}$-$R^{16}$, -$Q^{4a}$-$NR^{14}R^{15}$, -$Q^{4a}$-$NR^{14}$-$Q^{4b}$-$R^{16}$, -$Q^{4a}$-$COR^{14}$, -$Q^{4a}$-CO-$Q^{4b}$-$R^{16}$, -$Q^{4a}$-$NR^{14}COR^{15}$, -$Q^{4a}$-$NR^{14}CO$-$Q^{4b}$-$R^{16}$, -$Q^{4a}$-$NR^{14}C(O)OR^{15}$, -$Q^{4a}$-$NR^{14}C(O)O$-$Q^{4b}$-$R^{16}$, $Q^{4a}$-$SO_2R^{14}$, -$Q^{4a}$-$SO_2$-$Q^{4b}$-$R^{16}$, $Q^{4a}$-$CONR^{14}R^{15}$, -$Q^{4a}$-$CONR^{14}$-$Q^{4b}$-$R^{16}$, -$Q^{4a}$-$CO_2R^{14}$, -$Q^{4a}$-$CO_2$-$Q^{4b}$-$R^{16}$, -$Q^{4a}$-$SO_2NR^{14}R^{15}$, -$Q^{4a}$-$SO_2NR^{14}$-$Q^{4b}$-$R^{16}$, -$Q^{4a}$-$NR^{14}SO_2R^{15}$, -$Q^{4a}$-$NR^{14}SO_2$-$Q^{4b}$-$R^{16}$ and -$Q^{4a}$-$NR^{14}SO_2NR^{15}R^{15a}$, -$Q^{4a}$-$NR^{14}SO_2NR^{15}$-$Q^{4b}$-$R^{16}$; wherein $Q^{4a}$ and $Q^{4b}$ independently represent a covalent bond, optionally substituted $C_1$-$C_6$ alkylene or optionally substituted $C_2$-$C_6$ alkenylene;

$R^{14}$, $R^{15}$ and $R^{15a}$ each independently represent hydrogen or optionally substituted $C_1$-$C_6$ alkyl; and $R^{16}$ represents optionally substituted heterocyclyl, optionally substituted heteroaryl, optionally substituted aryl, or an optionally substituted cycloalkyl.

$R^{16}$ may be substituted with further optionally substituted 3 to 10 membered heterocyclyl, heteroaryl, aryl or cycloalkyl rings, either directly attached or via linking group. The linking group may be an oxygen, a carbonyl or an optionally substituted $C_1$-$C_6$ alkylene chain. The linking group may be oxygen, —CO— or a $C_1$-$C_6$ alkylene group. In one embodiment the linking group may be a carbonyl, or an alkylene chain, for example, —CO— or a $C_1$-$C_6$ alkylene group. In particular, $R^{16}$ is unsubstituted or substituted with one or more substituents selected from halogen, hydroxyl, thiol, cyano, amino, amido, nitro, $SF_5$, $C_1$-$C_3$ alkyl or $C_1$-$C_3$ alkoxy wherein the alkyl or alkoxy may be optionally substituted with hydroxyl, thiol, cyano, amino, amido, nitro or $SF_5$. Preferably, $R^{16}$ is unsubstituted.

In particular, D may be substituted with one or more substituents selected from optionally substituted $C_1$-$C_6$ alkyl, optionally substituted $C_1$-$C_6$ alkoxy and —$CONR^{14}R^{15}$ (i.e. -$Q^{4a}$-$CONR^{14}R^{14}$ where $Q^{4a}$ is a covalent bond), wherein $R^{14}$ and $R^{15}$ are as defined above.

More particularly, D may be unsubstituted or substituted with methyl, i-propyl, methoxy or —$C(O)NH_2$.

The optional substituents for the alkyl and alkoxy within the definitions of D and $R^{14}$, $R^{15}$ and $R^{15a}$ may be selected from halogen, hydroxyl, thiol, cyano, amino, amido, nitro and $SF_5$. In particular, the optional substituents are fluorine.

In one embodiment, D is unsubstituted, mono-substituted, di-substituted or tri-substituted. In particular, D is unsubstituted, mono-substituted or di-substituted. For example, D is unsubstituted or mono-substituted. In some embodiments, D is unsubstituted.

In certain instances, D is selected from phenyl, naphthyl, naphthalenyl, pyridinyl, pyrazinyl, pyrimidinyl, pyridazinyl, furyl, pyrrolyl, oxazolyl, thiazolyl, pyrazolyl, tetrazolyl, indolyl, indolizinyl, isoindolyl, indolinyl, purinyl, furazanyl, imidazolyl, indazolyl, isothiazolyl, isoxazolyl, oxadiazolyl, tetrazolyl, thiadiazolyl, benzofuranyl, isobenzofuranyl, benzothiophenyl, isobenzothiophenyl, benzimidazolyl, benzothiazolyl, napthyridinyl, pteridinyl, pyrazinyl, quinolinyl, isoquinolinyl, cinnolinyl, phthalazinyl, quinazolinyl, imidazopyridinyl, pyrazolopyridinyl, thiazolopyridinyl, isoindolinyl, triazinyl, dihydrophyridinyl, quinoxalinyl, dihydrobenzoxazinyl, dihydropyrrolopyridinyl which is either unsubstituted or substituted with one or more substituents selected from halogen, cyano, oxo, nitro, hydroxyl, —$SR^{14}$, optionally substituted —$C_1$-$C_6$ alkyl, optionally substituted —$C_1$-$C_6$ alkoxy, optionally substituted —$C_2$-$C_6$ alkenyl, optionally substituted —$C_2$-$C_6$ alkynyl, -$Q^{4a}$-$R^{16}$, -$Q^{4a}$-O-$Q^{4b}$-$R^{16}$, -$Q^{4a}$-S-$Q^{4b}$-$R^{16}$, -$Q^{4a}$-SO-$Q^{4b}$-$R^{16}$, -$Q^{4a}$-$NR^{14}CONR^{15}R^{15a}$, -$Q^{4a}$-$NR^{14}CONR^{15}$-$Q^{4b}$-$R^{16}$, -$Q^{4a}$-$NR^{14}R^{15}$, -$Q^{4a}$-$NR^{14}$-$Q^{4b}$-$R^{16}$, -$Q^{4a}$-$COR^{14}$, -$Q^{4a}$-CO-$Q^{4b}$-$R^{16}$, -$Q^{4a}$-$NR^{14}COR^{15}$, -$Q^{4a}$-$NR^{14}CO$-$Q^{4b}$-$R^{16}$, -$Q^{4a}$-$NR^{14}C(O)OR^{15}$, -$Q^{4a}$-$NR^{14}C(O)O$-$Q^{4b}$-$R^{16}$, -$Q^{4a}$-$SO_2R^{14}$, -$Q^{4a}$-$SO_2$-$Q^{4b}$-$R^{16}$, -$Q^{4a}$-$CONR^{14}R^{15}$, -$Q^{4a}$-$CONR^{14}$-$Q^{4b}$-$R^{16}$, -$Q^{4a}$-$CO_2R^{14}$, -$Q^{4a}$-$CO_2$-$Q^{4b}$-$R^{16}$, -$Q^{4a}$-$SO_2NR^{14}R^{15}$, -$Q^{4a}$-$SO_2NR^{14}$-$Q^{4b}$-$R^{16}$, -$Q^{4a}$-$NR^{14}SO_2R^{15}$, -$Q^{4a}$-$NR^{14}SO_2$-$Q^{4b}$-$R^{16}$ and -$Q^{4a}$-$NR^{14}SO_2NR^{15}R^{15a}$, -$Q^{4a}$-$NR^{14}SO_2NR^{15}$-$Q^{4b}$-$R^{16}$; wherein $Q^{4a}$ and $Q^{4b}$ independently represent a covalent bond, optionally substituted $C_1$-$C_6$ alkylene or optionally substituted $C_2$-$C_6$ alkenylene; $R^{14}$, $R^{15}$ and $R^{15a}$ each independently represent hydrogen or optionally substituted $C_1$-$C_6$ alkyl; and $R^{16}$ represents optionally substituted heterocyclyl, optionally substituted heteroaryl, optionally substituted aryl, or an optionally substituted cycloalkyl.

D may represent a ring selected from phenyl, isoquinolinyl and pyridinyl which may be unsubstituted or substituted with one or more substituents selected from halogen, cyano, oxo, nitro, hydroxyl, —$SR^{14}$, optionally substituted —$C_1$-$C_6$ alkyl, optionally substituted —$C_1$-$C_6$ alkoxy, optionally substituted —$C_2$-$C_6$ alkenyl, optionally substituted —$C_2$-$C_6$ alkynyl, -$Q^{4a}$-$R^{16}$, -$Q^{4a}$-O-$Q^{4b}$-$R^{16}$, -$Q^{4a}$-S-$Q^{4b}$-$R^{16}$, -$Q^{4a}$-SO-$Q^{4b}$-$R^{16}$, -$Q^{4a}$-$NR^{14}CONR^{15}R^{15a}$, -$Q^{4a}$-$NR^{14}CONR^{15}$-$Q^{4b}$-$R^{16}$, -$Q^{4a}$-$NR^{14}R^{15}$, -$Q^{4a}$-$NR^{14}$-$Q^{4b}$-$R^{16}$, -$Q^{4a}$-$COR^{14}$, -$Q^{4a}$-CO-$Q^{4b}$-$R^{16}$, -$Q^{4a}$-$NR^{14}COR^{15}$, -$Q^{4a}$-$NR^{14}CO$-$Q^{4b}$-$R^{16}$, -$Q^{4a}$-$NR^{14}C(O)OR^{15}$, -$Q^{4a}$-$NR^{14}C(O)O$-$Q^{4b}$-$R^{16}$, -$Q^{4a}$-$SO_2R^{14}$, -$Q^{4a}$-$SO_2$-$Q^{4b}$-$R^{16}$, $Q^{4a}$-$CONR^{14}R^{15}$, -$Q^{4a}$-$CONR^{14}$-$Q^{4b}$-$R^{16}$, $Q^{4a}$-$CO_2R^{14}$, -$Q^{4a}$-$CO_2$-$Q^{4b}$-$R^{16}$, -$Q^{4a}$-$SO_2NR^{14}R^{15}$, -$Q^{4a}$-$SO_2NR^{14}$-$Q^{4b}$-$R^{16}$, -$Q^{4a}$-$NR^{14}SO_2R^{15}$, -$Q^{4a}$—$NR^{14}SO_2$-$Q^{4b}$-$R^{16}$ and -$Q^{4a}$-$NR^{14}SO_2NR^{15}R^{15a}$, -$Q^{4a}$-$NR^{14}SO_2NR^{15}$-$Q^{4b}$-$R^{16}$; wherein $Q^{4a}$ and $Q^{4b}$ independently represent a covalent bond, optionally substituted $C_1$-$C_6$ alkylene or optionally substituted $C_2$-$C_6$ alkenylene; $R^{14}$, $R^{15}$ and $R^{15a}$ each independently represent hydrogen or optionally substituted $C_1$-$C_6$ alkyl; and $R^{16}$ represents optionally substituted heterocyclyl, optionally substituted heteroaryl, optionally substituted aryl, or an optionally substituted cycloalkyl.

D may represent a ring selected from phenyl, isoquinolinyl and pyridinyl which may which may unsubstituted or substituted with one or more (e.g. one, two or three) substituents selected from optionally substituted $C_1$-$C_6$ alkyl, optionally substituted $C_1$-$C_6$ alkoxy and —$CONR^{14}R^{15}$ wherein $R^{14}$ and $R^{15}$ each independently represent hydrogen or optionally substituted $C_1$-$C_6$ alkyl.

In one embodiment, there is provided a compound of formula I as defined above, or a pharmaceutically acceptable salt thereof, wherein the compound is not:

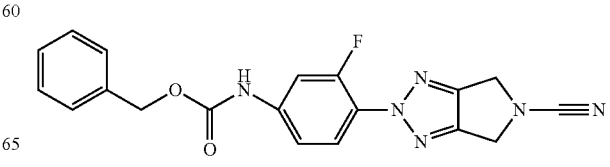

benzyl(4-(5-cyano-5,6-dihydropyrrolo[3,4-d][1,2,3]tri-azol-2(4H)-yl)-3-fluorophenyl)carbamate.

In one embodiment, there is provided a compound of formula I as defined above, or a pharmaceutically acceptable salt thereof, wherein the compound is not:

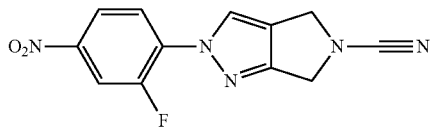 [SMILES: N#CN1Cc2cn(-c3ccc([N+](=O)[O-])cc3F)nc2C1]

2-(2-fluoro-4-nitrophenyl)-2,6-dihydropyrrolo[3,4-c]pyrazole-5(4H)-carbonitrile.

Examples of novel compounds of formula I include:
1-(4-methoxyphenyl)-4,6-dihydropyrrolo[3,4-c]pyrazole-5(1H)-carbonitrile;
1-phenyl-4,6-dihydropyrrolo[3,4-c]pyrazole-5(1H)-carbonitrile;
1-(4-fluorophenyl)-4,6-dihydropyrrolo[3,4-c]pyrazole-5(1H)-carbonitrile;
1-(2-fluorophenyl)-4,6-dihydropyrrolo[3,4-c]pyrazole-5(1H)-carbonitrile;
4-(5-cyano-5,6-dihydropyrrolo[3,4-c]pyrazol-1(4H)-yl)benzamide;
1-(quinolin-3-yl)-4,6-dihydropyrrolo[3,4-c]pyrazole-5(1H)-carbonitrile;
1-(3-methoxyphenyl)-4,6-dihydropyrrolo[3,4-c]pyrazole-5(1H)-carbonitrile;
1-(1-phenyl-1H-pyrazol-4-yl)-4,6-dihydropyrrolo[3,4-c]pyrazole-5(1H)-carbonitrile;
1-(1-phenyl-1H-imidazol-4-yl)-4,6-dihydropyrrolo[3,4-c]pyrazole-5(1H)-carbonitrile;
3-methyl-1-phenyl-4,6-dihydropyrrolo[3,4-c]pyrazole-5(1H)-carbonitrile;
N-benzyl-3-(5-cyano-5,6-dihydropyrrolo[3,4-c]pyrazol-1(4H)-yl)benzamide;
3-(5-cyano-5,6-dihydropyrrolo[3,4-c]pyrazol-1(4H)-yl)-N-(1-phenylethyl)benzamide;
3-(5-cyano-5,6-dihydropyrrolo[3,4-c]pyrazol-1(4H)-yl)-N-(pyridin-2-ylmethyl)benzamide;
4-(5-cyano-5,6-dihydropyrrolo[3,4-c]pyrazol-1(4H)-yl)-N-(pyridin-2-ylmethyl)benzamide;
4-(5-cyano-5,6-dihydropyrrolo[3,4-c]pyrazol-1(4H)-yl)-N-methylbenzamide;
4-(5-cyano-3-methyl-5,6-dihydropyrrolo[3,4-c]pyrazol-1(4H)-yl)benzamide;
1-(1-methyl-1H-indazol-5-yl)-4,6-dihydropyrrolo[3,4-c]pyrazole-5(1H)-carbonitrile;
5-(5-cyano-5,6-dihydropyrrolo[3,4-c]pyrazol-1(4H)-yl)-2-methoxy-N-methylbenzamide;
1-(1H-indazol-3-yl)-4,6-dihydropyrrolo[3,4-c]pyrazole-5(1H)-carbonitrile;
1-(3-phenyl-1H-pyrazol-5-yl)-4,6-dihydropyrrolo[3,4-c]pyrazole-5(1H)-carbonitrile;
1-methyl-3-phenyl-4,6-dihydropyrrolo[3,4-c]pyrazole-5(1H)-carbonitrile;
2-methyl-3-phenyl-2,6-dihydropyrrolo[3,4-c]pyrazole-5(4H)-carbonitrile;
1-isopropyl-3-phenyl-4,6-dihydropyrrolo[3,4-c]pyrazole-5(1H)-carbonitrile;
1-benzyl-3-phenyl-4,6-dihydropyrrolo[3,4-c]pyrazole-5(1H)-carbonitrile;
1-benzyl-3-(5-isopropyl-2-methoxyphenyl)-4,6-dihydropyrrolo[3,4-c]pyrazole-5(1H)-carbonitrile;
3-(5-isopropyl-2-methoxyphenyl)-4,6-dihydropyrrolo[3,4-c]pyrazole-5(1H)-carbonitrile;
3-(2-fluoro-5-methylphenyl)-4,6-dihydropyrrolo[3,4-c]pyrazole-5(1H)-carbonitrile;
5-(5-cyano-5,6-dihydropyrrolo[3,4-c]pyrazol-1(4H)-yl)-1H-pyrazole-3-carboxamide;
3-phenyl-4,6-dihydropyrrolo[3,4-c]pyrazole-5(1H)-carbonitrile;
3-(isoquinolin-3-ylamino)-2-methyl-2,6-dihydropyrrolo[3,4-c]pyrazole-5(4H)-carbonitrile;
3-(isoquinolin-3-ylamino)-4,6-dihydropyrrolo[3,4-c]pyrazole-5(1H)-carbonitrile;
1-benzyl-3-(isoquinolin-3-ylamino)-4,6-dihydropyrrolo[3,4-c]pyrazole-5(1H)-carbonitrile;
4-(5-cyano-3-(pyridin-2-ylamino)-5,6-dihydropyrrolo[3,4-c]pyrazol-1(4H)-yl)benzamide;
N-((5-cyano-1,4,5,6-tetrahydropyrrolo[3,4-c]pyrazol-3-yl)methyl)-3-phenyl-1H-pyrazole-5-carboxamide;
N-((5-cyano-1-phenyl-1,4,5,6-tetrahydropyrrolo[3,4-c]pyrazol-3-yl)methyl)-4-methylbenzamide;
N-((5-cyano-1-phenyl-1,4,5,6-tetrahydropyrrolo[3,4-c]pyrazol-3-yl)methyl)acetamide;
3-(4-(benzyloxy)phenyl)-4,6-dihydropyrrolo[3,4-c]pyrazole-5(1H)-carbonitrile;
3-(3-cyanophenyl)-4,6-dihydropyrrolo[3,4-c]pyrazole-5(1H)-carbonitrile;
3-(1-methyl-1H-pyrazol-5-yl)-4,6-dihydropyrrolo[3,4-c]pyrazole-5(1H)-carbonitrile;
3-(3-(trifluoromethoxy)phenyl)-4,6-dihydropyrrolo[3,4-c]pyrazole-5(1H)-carbonitrile;
3-(4-phenoxyphenyl)-4,6-dihydropyrrolo[3,4-c]pyrazole-5(1H)-carbonitrile;
3-(4-cyanophenyl)-4,6-dihydropyrrolo[3,4-c]pyrazole-5(1H)-carbonitrile;
3-(2-fluoro-4-(trifluoromethyl)phenyl)-4,6-dihydropyrrolo[3,4-c]pyrazole-5(1H)-carbonitrile;
3-(2-chloro-5-(trifluoromethoxy)phenyl)-4,6-dihydropyrrolo[3,4-c]pyrazole-5(1H)-carbonitrile;
5-(5-cyano-1,4,5,6-tetrahydropyrrolo[3,4-c]pyrazol-3-yl)-N-methylpicolinamide;
3-(6-methoxypyridin-3-yl)-4,6-dihydropyrrolo[3,4-c]pyrazole-5(1H)-carbonitrile;
3-(5-cyano-1,4,5,6-tetrahydropyrrolo[3,4-c]pyrazol-3-yl)-N,N-dimethylbenzenesulfonamide;
3-(5-fluoro-2-isopropoxyphenyl)-4,6-dihydropyrrolo[3,4-c]pyrazole-5(1H)-carbonitrile;
N-benzyl-4-(5-cyano-1,4,5,6-tetrahydropyrrolo[3,4-c]pyrazol-3-yl)benzamide;
3-(6-isopropoxypyridin-3-yl)-4,6-dihydropyrrolo[3,4-c]pyrazole-5(1H)-carbonitrile;
3-(4-(4-methylpiperazine-1-carbonyl)phenyl)-4,6-dihydropyrrolo[3,4-c]pyrazole-5(1H)-carbonitrile;
3-(1-methyl-1H-indazol-5-yl)-4,6-dihydropyrrolo[3,4-c]pyrazole-5(1H)-carbonitrile;
3-(1-benzyl-1H-pyrazol-5-yl)-4,6-dihydropyrrolo[3,4-c]pyrazole-5(1H)-carbonitrile;
3-(5-methyl-1H-indazol-4-yl)-4,6-dihydropyrrolo[3,4-c]pyrazole-5(1H)-carbonitrile;

3-(5-cyano-1,4,5,6-tetrahydropyrrolo[3,4-c]pyrazol-3-yl)-N-cyclopropylbenzenesulfonamide;
N-(3-(5-cyano-1,4,5,6-tetrahydropyrrolo[3,4-c]pyrazol-3-yl)phenyl)cyclopropanesulfonamide;
3-(3-fluorophenyl)-4,6-dihydropyrrolo[3,4-c]pyrazole-5(1H)-carbonitrile;
3-(2-fluorophenyl)-4,6-dihydropyrrolo[3,4-c]pyrazole-5(1H)-carbonitrile;
3-(4-fluorophenyl)-4,6-dihydropyrrolo[3,4-c]pyrazole-5(1H)-carbonitrile;
3-(2-fluoro-5-methylphenyl)-1-methyl-4,6-dihydropyrrolo[3,4-c]pyrazole-5(1H)-carbonitrile;
3-(2-fluoro-5-methylphenyl)-2-methyl-2,6-dihydropyrrolo[3,4-c]pyrazole-5(4H)-carbonitrile;
3-(5-isopropyl-2-methoxyphenyl)-1-methyl-4,6-dihydropyrrolo[3,4-c]pyrazole-5(1H)-carbonitrile;
3-(5-isopropyl-2-methoxyphenyl)-2-methyl-2,6-dihydropyrrolo[3,4-c]pyrazole-5(4H)-carbonitrile;
3-(5-ethyl-2-methoxyphenyl)-4,6-dihydropyrrolo[3,4-c]pyrazole-5(1H)-carbonitrile;
6-chloro-N-((5-cyano-1,4,5,6-tetrahydropyrrolo[3,4-c]pyrazol-3-yl)methyl)imidazo[1,2-a]pyridine-2-carboxamide;
3-(4-(4-methylpiperazin-1-yl)phenyl)-4,6-dihydropyrrolo[3,4-c]pyrazole-5(1H)-carbonitrile;
3-(4-chloro-2-methoxyphenyl)-4,6-dihydropyrrolo[3,4-c]pyrazole-5(4H)-carbonitrile;
3-(1-(1-methylpiperidin-4-yl)-1H-pyrazol-4-yl)-4,6-dihydropyrrolo[3,4-c]pyrazole-5(1H)-carbonitrile;
3-(6-(4-methylpiperazin-1-yl)pyridin-3-yl)-4,6-dihydropyrrolo[3,4-c]pyrazole-5(1H)-carbonitrile;
3-(2-methoxy-4-(1H-pyrazol-1-yl)phenyl)-4,6-dihydropyrrolo[3,4-c]pyrazole-5(4H)-carbonitrile;
3-(3-(4-methylpiperazin-1-yl)phenyl)-4,6-dihydropyrrolo[3,4-c]pyrazole-5(1H)-carbonitrile;
3-(4-morpholinophenyl)-4,6-dihydropyrrolo[3,4-c]pyrazole-5(1H)-carbonitrile;
3-(2-fluoro-4-(4-methylpiperazin-1-yl)phenyl)-4,6-dihydropyrrolo[3,4-c]pyrazole-5(1H)-carbonitrile;
3-(3-methyl-4-(4-methylpiperazin-1-yl)phenyl)-4,6-dihydropyrrolo[3,4-c]pyrazole-5(1H)-carbonitrile;
3-(3-(2-oxooxazolidin-3-yl)phenyl)-4,6-dihydropyrrolo[3,4-c]pyrazole-5(1H)-carbonitrile;
3-(3-(2-oxopyrrolidin-1-yl)phenyl)-4,6-dihydropyrrolo[3,4-c]pyrazole-5(1H)-carbonitrile;
3-(5-chloro-2-methoxyphenyl)-4,6-dihydropyrrolo[3,4-c]pyrazole-5(4H)-carbonitrile;
N-(3-(5-cyano-5,6-dihydropyrrolo[3,4-c]pyrazol-1(4H)-yl)phenyl)cyclopropanesulfonamide; and
N-benzyl-4-(5-cyano-1,4,5,6-tetrahydropyrrolo[3,4-c]pyrazol-3-yl)-3-fluorobenzamide.

It should be noted that each of the chemical compounds listed above represents a particular and independent aspect of the invention.

According to a further aspect of the invention there is provided a process for the preparation of a compound of formula I or a pharmaceutically acceptable salt thereof, or a compound of formula II or a pharmaceutically acceptable salt thereof, comprising the steps of reacting an amine of formula III or formula IV respectively with cyanogen bromide to form N—CN compounds:

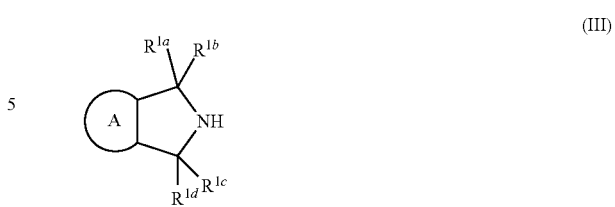

Wherein $R^{1a}$, $R^{1b}$, $R^{1c}$, $R^{1d}$ and A are as defined herein.

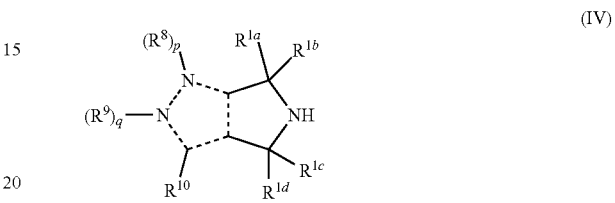

Wherein $R^{1a}$, $R^{1b}$, $R^{1c}$, $R^{1d}$, $R^8$, $R^9$, $R^{10}$ p and q are as defined herein.

According to a further aspect of the invention there is provided a pharmaceutical composition comprising a compound of the invention.

The compounds of the invention may be used in the treatment of disorders and diseases related to DUB or desumoylation inhibition, particularly USP7.

According to a further aspect of the invention there is provided a compound of formula (I) or pharmaceutical composition thereof for use in therapy. In particular, the compounds of the invention have use in the treatment of cancer and more particularly in the treatment of cancer linked to DUB or desumoylation activity. Compounds of the invention may be useful against any DUB or desumoylating enzyme, including but not limited to USP7, USP30, USP47, SENP2 and SENP6.

The compounds described herein may be used in the manufacture of a medicament for the treatment of cancer linked to DUB or desumoylation activity.

In a further aspect of the invention there is provided a method of treatment or prevention of cancer linked to USP7 activity, the method comprising administering a pharmaceutically effective amount of a compound of the invention or a pharmaceutical composition thereof to an individual suffering from cancer linked to USP7 activity.

The compounds or compositions disclosed herein may be used to treat cancer. References to "cancer" or "tumour" include but are not limited to breast, ovarian, prostate, lung, kidney, gastric, colon, testicular, head and neck, pancreas, brain, melanoma, bone, liver, soft tissue or other cancers of tissue organs and cancers of the blood cells such as lymphomas and leukaemias. Particular cancers include lymphoma, multiple myeloma, CML, AML, mantle cell lymphoma, neuroblastoma, colorectal cancer, melanoma, soft tissue sarcomas including liposarcoma, fibroblastic sarcoma and leiomyosarcoma, hepatocellular carcinoma, osteosarcoma, oesophageal cancer and non-small cell lung carcinoma.

The compounds or compositions disclosed herein may be used to treat additional diseases linked to USP7 activity.

The compounds of the invention or pharmaceutical compositions thereof as described herein may be combined with one or more additional agents. The compounds may be combined with one or more additional anti-tumour therapeutic agents, for example chemotherapeutic drugs immune checkpoint inhibitors or inhibitors of other regulatory proteins. In a one embodiment the one or more anti-tumour agent is a chemotherapeutic agent. Chemotherapeutic agents may be selected from olaparib, mitomycin C, cisplatin, carboplatin, oxaliplatin, ionizing radiation (IR), camptothecin, irinotecan, topotecan, temozolomide, taxanes, 5-fluoropyrimidines, gemcitabine, and doxorubicin. In a further embodiment the additional anti-tumour therapeutic agent is a BH-3 mimetic. In a further embodiment BH-3 mimetics may be selected from but not limited to one or more of ABT-737, ABT-199, ABT-263, and Obatoclax.

As discussed above, the compounds of the invention may be useful in the treatment of disorders and diseases related to USP30 inhibition. The compounds of the invention may therefore be useful in the treatment of disorders or diseases having a component relating to mitochondrial dysfunction.

Mitochondria are specialized subcellular organelles required for energy production in the form of ATP. In the case of mitochondrial dysfunction, cells cannot produce sufficient ATP resulting in cell injury or death. Diseases of the mitochondria appear most often in organs that are very energy demanding such as the brain, heart, liver, skeletal muscles, kidney and the endocrine and respiratory system.

The condition involving mitochondrial dysfunction may be selected from a condition involving a mitophagy defect, a condition involving a mutation in mitochondrial DNA, a condition involving mitochondrial oxidative stress, a condition involving a defect in mitochondrial membrane potential, mitochondrial biogenesis, a condition involving a defect in mitochondrial shape or morphology, and a condition involving a lysosomal storage defect.

In particular, the condition involving mitochondrial dysfunction may be selected from a neurodegenerative disease; multiple sclerosis (MS), mitochondrial myopathy, encephalopathy, lactic acidosis, and stroke-like episodes (MELAS) syndrome; Leber's hereditary optic neuropathy (LHON); cancer; neuropathy, ataxia, retinitis pigmentosa-maternally inherited Leigh syndrome (NARP-MILS); Danon disease; diabetes; diabetic nephropathy; metabolic disorders; heart failure; ischemic heart disease leading to myocardial infarction; psychiatric diseases, for example schizophrenia; multiple sulfatase deficiency (MSD); mucolipidosis II (ML II); mucolipidosis III (ML III); mucolipidosis IV (ML IV); GM1-gangliosidosis (GM1); neuronal ceroid-lipofuscinoses (NCL1); Alpers disease; Barth syndrome; Beta-oxidation defects; carnitine-acyl-carnitine deficiency; carnitine deficiency; creatine deficiency syndromes; co-enzyme Q10 deficiency; complex I deficiency; complex II deficiency; complex III deficiency; complex IV deficiency; complex V deficiency; COX deficiency; chronic progressive external ophthalmoplegia syndrome (CPEO); CPT I deficiency; CPT II deficiency; glutaric aciduria type II; Kearns-Sayre syndrome; lactic acidosis; long-chain acyl-CoA dehydrogenase deficiency (LCHAD); Leigh disease or syndrome; lethal infantile cardiomyopathy (LIC); Luft disease; glutaric aciduria type II; medium-chain acyl-CoA dehydrogenase deficiency (MCAD); myoclonic epilepsy and ragged-red fiber (MERRF) syndrome; mitochondrial cytopathy; mitochondrial recessive ataxia syndrome; mitochondrial DNA depletion syndrome; myoneurogastointestinal disorder and encephalopathy; Pearson syndrome; pyruvate dehydrogenase deficiency; pyruvate carboxylase deficiency; POLG mutations; medium/short-chain 3-hydroxyacyl-CoA dehydrogenase (M/SCHAD) deficiency; and very long-chain acyl-CoA dehydrogenase (VLCAD) deficiency.

The condition involving mitochondrial dysfunction may be a CNS disorder, for example a neurodegenerative disease. Neurodegenerative diseases include, but are not limited to, Parkinson's disease, Alzheimer's disease, amyotrophic lateral sclerosis (ALS), Huntington's disease, ischemia, stroke, dementia with Lewy bodies, and frontotemporal dementia.

Dosage Forms

The pharmaceutical compositions of the invention may be designed for administration by the oral, parenteral or mucosal route and the choice or the specific form of composition is dependent on the administration route. Thus for oral administration the composition may be in the form, for example, of tablets, lozenges, dragees, films, powders, elixirs, syrups, liquid preparations including dispersions, suspensions, emulsions, solutions or sprays, cachets, granules, capsules, etc. For administration to mucosa the composition may be in the form of sprays, inhalants, dispersions, suspensions, emulsions, solutions, gels, patches, films, ointments, creams, lotions, suppositories etc. For parenteral administration the composition is in the form of a liquid preparation such as a solution, dispersion, emulsion or suspension including liposome compositions.

Preparations according to the invention for parenteral administration include sterile aqueous, aqueous-organic, and organic solutions, suspensions and emulsions.

Such dosage forms are prepared according to techniques known in the art of pharmaceutical formulation. When in the form of sprays or inhalants the pharmaceutical compositions may be administered nasally. Suitable formulations for this purpose are known to those skilled in the art.

The pharmaceutical compositions of the invention may be administered by injection and may be in the form of a sterile liquid preparation for injection, including liposome preparations. The pharmaceutical compositions of the invention may also be in the form of suppositories for rectal administration. These are formulated so that the pharmaceutical composition is solid at room temperature and liquid at body temperature to allow release of the active compound.

The dosages may be varied depending upon the requirements of the patient, the severity of the condition being treated, and the compound being employed. Determination of the proper dosage for a particular situation is within the remit of the person skilled in the skill of the art. Generally, treatment is initiated with smaller dosages which are less than the optimal dose of the compound. Thereafter the dosage is increased by small increments until the optimum effect under the circumstances is reached.

The magnitude of an effective dose of a compound will, of course, vary with the nature of the severity of the condition to be treated and with the particular compound and its route of administration. The selection of appropriate dosages is within the ability of one of ordinary skill in this art, without undue burden. The daily dose range is about 10 µg to about 100 mg per kg body weight of a human and non-human animal and in general may be around 10 µg to 30 mg per kg body weight per dose. The above dose may be given from one to three times per day.

Synthetic Methodologies

Compounds of the invention may be prepared via a variety of synthetic routes. Exemplary routes to certain compounds of the invention are shown below. Representative compounds of the present invention can be synthesized in accordance with the general synthetic methods described below and are illustrated more particularly in the schemes that follow. Since the schemes are an illustration, the invention should not be construed as being limited by the chemical reactions and conditions expressed. The preparation of the various starting materials used in the schemes is well within the skill of persons versed in the art. Those skilled in the art appreciate that, where appropriate, the individual transformations within a scheme can be completed in a different order. The following schemes describe general synthetic methods whereby intermediate and target compounds of the present invention may be prepared. Additional representative compounds and stereoisomers, racemic mixtures, diastereomers and enantiomers thereof can be synthesized using the intermediates prepared in accordance to the general schemes and other materials, compounds and reagents known to those skilled in the art. All such compounds, stereoisomers, racemic mixtures, diastereomers and enantiomers thereof are intended to be encompassed within the scope of the present invention.

All the compounds were characterised by either liquid chromatography-mass spectroscopy (LCMS) or $^1$H NMR or both.

Abbreviations

AcOH Acetic acid
Ar Aryl
BEH Ethylene Bridged Hybrid
Boc Tert-butoxycarbonyl
br Broad (NMR signal)
d Doublet (NMR signal)
dba dibenzylideneacetone
DCM Dichloromethane
DIPEA Diisopropylethylamine
DMAP 4-Dimethylaminopyridine
DMA-DMA N,N-Dimethylacetamide dimethyl acetal
DMF N,N-Dimethylformamide
DMF-DMA N,N-Dimethylformamide dimethyl acetal
DMSO Dimethylsulphoxide
Dppf 1,1'-Bis(diphenylphosphino)ferrocene
ES Electrospray
EtOAc Ethyl acetate
EtOH Ethanol
g gram(s)
h Hour(s)
HATU 1-[Bis(dimethylamino)methylene]-1H-1,2,3-triazolo[4,5-b]pyridinium 3-oxid hexafluorophosphate
m Multiplet (NMR signal)
M Molar
MeCN Acetonitrile
MeOH Methanol
min Minutes
ml millilitre
mm millimetre
mM millimolar
mmol millimoles
μm micrometre
μM micromolar
NCS N-chlorosuccinimide
PE Petroleum Ether
Ruphos 2-Dicyclohexylphosphino-2',6'-diisopropoxybiphenyl
rt Room temperature
RT Retention time
s Singlet (NMR signal)
t Triplet (NMR signal)
TEA Triethylamine
TFA Trifluoroacetic acid
THF Tetrahydrofuran
TLC Thin layer chromatography

| Method 1 | |
|---|---|
| Column | BEH C18, 50 × 2.1 mm, 1.7 μm or equivalent |
| Mobile Phase | (A) 5 mM Ammonium Acetate + 0.1% Formic Acid in Water |
| | (B) 0.1% Formic Acid in MeCN |
| Flow Rate | 0.55 ml/min |

| Gradient | Time | % B |
|---|---|---|
| | 0.01 | 5 |
| | 0.40 | 5 |
| | 0.80 | 35 |
| | 1.20 | 55 |
| | 2.50 | 100 |
| | 3.30 | 100 |
| | 3.31 | 5 |
| | 4.00 | 5 |

| Method 2 | |
|---|---|
| Column | X-bridge C18, 150 × 4.6 mm, 5 μm or equivalent |
| Mobile Phase | (A) 0.1% Ammonia in Water |
| | (B) 0.1% Ammonia in MeCN |
| Flow Rate | 1.0 ml/min |

| Gradient | Time | % B |
|---|---|---|
| | 0.01 | 10 |
| | 5.00 | 90 |
| | 7.00 | 100 |
| | 11.00 | 100 |
| | 11.01 | 10 |
| | 12.00 | 10 |

| Method 3 | |
|---|---|
| Column | YMC Triart C18 150 × 4.6 mm, 5 μm or equivalent |
| Mobile Phase | (A) 10 mM Ammonium Acetate in Water |
| | (B) 100% MeCN |
| Flow Rate | 1.0 ml/min |

| Gradient | Time | % B |
|---|---|---|
| | 0.01 | 10 |
| | 5.00 | 90 |
| | 7.00 | 100 |
| | 11.00 | 100 |
| | 11.01 | 10 |
| | 12.00 | 10 |

| Method 4 | |
|---|---|
| Column | X-bridge C18, 50 × 4.6 mm, 3.5 μm or equivalent |
| Mobile Phase | (C) 0.1% Ammonia in Water |
| | (D) 0.1% Ammonia in MeCN |
| Flow Rate | 1.0 ml/min |

| Gradient | Time | % B |
|---|---|---|
| | 0.01 | 5 |
| | 5.00 | 90 |
| | 5.80 | 95 |
| | 7.20 | 95 |
| | 7.21 | 5 |
| | 10.00 | 5 |

| Method 5 | |
|---|---|
| Column | X-bridge C18, 250 × 4.6 mm, 5 μm or equivalent |
| Mobile Phase | (A) 0.1% Ammonia in Water |
| | (B) 0.1% Ammonia in MeCN |
| Flow Rate | 1.0 ml/min |

| Gradient | Time | % B |
|---|---|---|
| | 0.01 | 5 |
| | 5.00 | 5 |
| | 10.00 | 30 |
| | 15.00 | 30 |
| | 25.00 | 60 |
| | 30.00 | 90 |
| | 35.00 | 90 |
| | 35.01 | 5 |
| | 40.00 | 5 |

| Method 6 | |
|---|---|
| Column | BEH C18, 50 × 2.1 mm, 1.7 μm or equivalent |
| Mobile Phase | (A) 5 mM Ammonium Acetate + 0.1% Formic Acid in Water |
| | (B) 0.1% Formic Acid in MeCN |
| Flow Rate | 0.45 ml/min |

| Gradient | Time | % B |
|---|---|---|
| | 0.01 | 2 |
| | 0.50 | 2 |
| | 5.00 | 90 |
| | 6.00 | 95 |
| | 7.00 | 95 |
| | 7.01 | 2 |
| | 8.00 | 2 |

| Method 7 | |
|---|---|
| Column | Agilent TC-C18, 2.1 × 50 mm, 5 μm or equivalent |
| Mobile Phase | (A) 0.04% TFA in water |
| | (B) 0.02% TFA in MeCN |
| Flow Rate | 0.80 ml/min |

| Gradient | Time | % B |
|---|---|---|
| | 0.01 | 1 |
| | 3.40 | 100 |
| | 4.00 | 100 |
| | 4.01 | 1 |
| | 4.50 | 1 |

| Method 8 | |
|---|---|
| Column | Agilent TC-C18, 2.1 × 50 mm, 5 μm or equivalent |
| Mobile Phase | (A) 0.04% TFA in water |
| | (B) 0.02% TFA in MeCN |
| Flow Rate | 0.80 ml/min |

| Gradient | Time | % B |
|---|---|---|
| | 0.01 | 10 |
| | 3.40 | 100 |
| | 4.00 | 100 |
| | 4.01 | 10 |
| | 4.50 | 10 |

| Method 9 | |
|---|---|
| Column | XBridge ShieldRP18, 2.1 × 50 mm, 5 μm or equivalent |
| Mobile Phase | (A) 0.05% Ammonia in water |
| | (B) MeCN |
| Flow Rate | 0.80 ml/min |

| Gradient | Time | % B |
|---|---|---|
| | 0.01 | 5 |
| | 3.40 | 100 |
| | 4.00 | 100 |
| | 4.01 | 5 |
| | 4.50 | 5 |

| Method 10 | |
|---|---|
| Column | Sunfire C18 250 × 4.6 mm, 5 μm or equivalent |
| Mobile Phase | (A) 0.1% TFA in water |
| | (B) MeCN |
| Flow Rate | 1.0 ml/min |

| Gradient | Time | % B |
|---|---|---|
| | 0.01 | 0 |
| | 5.00 | 0 |
| | 15.00 | 10 |
| | 25.00 | 20 |
| | 50.00 | 25 |
| | 50.01 | 0 |
| | 55.00 | 0 |

| Method 11 | |
|---|---|
| Column | X-bridge C18, 250 × 4.6 mm, 5 μm or equivalent |
| Mobile Phase | (A) 0.1% Ammonia in Water |
| | (B) 0.1% Ammonia in MeCN |
| Flow Rate | 1.0 ml/min |

| Gradient | Time | % B |
|---|---|---|
| | 0.01 | 5 |
| | 5.00 | 5 |
| | 10.00 | 30 |
| | 15.00 | 30 |
| | 25.00 | 60 |
| | 30.00 | 90 |
| | 35.00 | 90 |
| | 35.01 | 5 |
| | 40.00 | 5 |

| Method 12 | |
|---|---|
| Column | YMC Triart C18 150 × 4.6 mm, 5 μm or equivalent |
| Mobile Phase | (A) 0.1% Formic Acid in Water |
| | (B) 0.1% Formic Acid in MeCN |
| Flow Rate | 1.0 ml/min |

| Gradient | Time | % B |
|---|---|---|
| | 0.01 | 0 |
| | 7.00 | 50 |
| | 9.00 | 95 |
| | 13.00 | 95 |
| | 13.01 | 0 |
| | 17.00 | 0 |

| Method 13 | |
|---|---|
| Column | Agilent Poroshell 120 (SB-C18, 4.6 mm × 30 mm, 2.7 μm) or equivalent |
| Mobile Phase | (A) 0.1% v/v formic acid in water<br>(B) 0.1% v/v formic acid in MeCN |
| Flow Rate | 2.0 ml/min |

| Gradient | Time | % B |
|---|---|---|
| | 0.5 | 5 |
| | 1.5 | 100 |
| | 4.0 | 100 |
| | 4.3 | 5 |
| | 4.5 | 5 |

| Method 14 | |
|---|---|
| Column | Agilent Poroshell 120 (SB-C18, 4.6 mm × 30 mm, 2.7 μm) or equivalent |
| Mobile Phase | (A) 0.1% v/v formic acid in water<br>(B) 0.1% v/v formic acid in MeCN |
| Flow Rate | 2.0 ml/min |

| Gradient | Time | % B |
|---|---|---|
| | 0.5 | 5 |
| | 3.0 | 100 |
| | 5.0 | 100 |
| | 5.5 | 5 |
| | 6.5 | 5 |

| Method 15 | |
|---|---|
| Column | Agilent Poroshell 120 (SB-C18, 4.6 mm × 30 mm, 2.7 μm) or equivalent |
| Mobile Phase | (A) 0.1% v/v formic acid in water<br>(B) 0.1% v/v formic acid in MeCN |
| Flow Rate | 2.0 ml/min |

| Gradient | Time | % B |
|---|---|---|
| | 0.5 | 5 |
| | 1.5 | 100 |
| | 4.5 | 100 |
| | 4.8 | 5 |
| | 5.0 | 5 |

Intermediate A tert-Butyl (Z)-3-((dimethylamino)methylene)-4-oxopyrrolidine-1-carboxylate

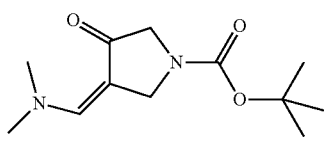 [SMILES: CN(C)/C=C1/CN(C(=O)OC(C)(C)C)CC1=O]

To a solution of tert-butyl 3-oxopyrrolidine-1-carboxylate (CAS Number 101385-93-7, available from Combi Blocks) (5.00 g, 27.0 mmol) in 1,4-dioxane (50 ml) was added DMF-DMA (4.79 g, 40.0 mmol) at rt. The reaction mixture was heated at 100° C. for 4 h. The resulting reaction mixture was cooled to rt and concentrated under reduced pressure. The resulting residue was co evaporated with n-hexane (25 ml). The resulting residue was triturated with n-hexane (2×5 ml) and finally dried yielding tert-butyl (Z)-3-((dimethylamino)methylene)-4-oxopyrrolidine-1-carboxylate (4.530 g, 18.87 mmol). This material was used directly for the next step without further purification. LCMS: Method 1, 1.843 min, MS: ES+ 241.23; $^1$H NMR (400 MHz, DMSO-d6) δ ppm 7.21 (s, 1H), 4.47 (d, J=9.60 Hz, 2H), 3.59 (d, J=11.20 Hz, 2H), 3.06 (s, 6H), 1.42 (d, J=6.00 Hz, 9H).

Intermediate B tert-Butyl (Z)-3-(1-(dimethylamino)ethylidene)-4-oxopyrrolidine-1-carboxylate

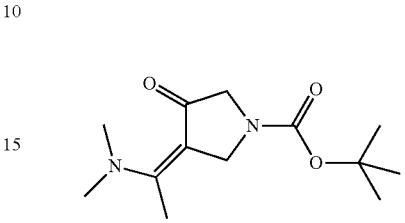

A solution of 1-N-Boc-3-pyrrolidinone (CAS Number 101385-93-7, available from Combi blocks) (1.0 g, 5.399 mmol) in DMF-DMA (3 ml) was heated at 80° C. for 3 h. The resulting reaction mixture was cooled to rt and concentrated under vacuum yielding tert-butyl (Z)-3-(1-(dimethylamino)ethylidene)-4-oxo-pyrrolidine-1-carboxylate (0.80 g, 3.137 mmol). LCMS: Method 1, 1.720 min.

Intermediate C
4-Hydrazinyl-1-phenyl-1H-imidazole Hydrochloride

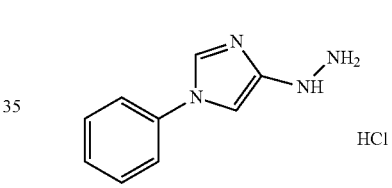

Step a. To a solution of 4-bromo-1H-imidazole (CAS Number 2302-25-2, available from Combi blocks) (5.0 g, 34.01 mmol) in MeOH (10 ml) were added phenylboronic acid (10.36 g, 85.03 mmol), NaOH (2.04 g, 51.0 mmol) and copper(II)chloride (0.55 g, 4.08 mmol) at rt. The reaction mixture was purged with oxygen. The resulting reaction mixture was heated at 65° C. for 3 h with continuous slow oxygen purging. The resulting reaction mixture was cooled to rt, poured into water (30 ml) and extracted with EtOAc (6×20 ml). The combined organic phase was dried over Na$_2$SO$_4$, filtered and concentrated under reduced pressure. The resulting residue was purified by flash chromatography (0.5% MeOH in DCM) yielding 4-bromo-1-phenyl-1H-imidazole (2.0 g, 9.049 mmol). LCMS: Method 1, 1.898 min, MS: ES+ 223.1.

Step b. To a solution of 4-bromo-1-phenyl-1H-imidazole (2.0 g, 9.010 mmol) in 1,4-dioxane (5 ml) were added di-tert-butyl hydrazinodicarboxylate (1.84 g, 8.144 mmol), N,N-dimethylethylenediamine (0.16 g, 1.809 mmol), K$_3$PO$_4$ (7.67 g, 36.198 mmol) and CuI (0.34 g, 1.809 mmol) at rt. The resulting reaction mixture was heated at 100° C. for 3 h. The resulting reaction mixture was poured into water (20 ml) and extracted with EtOAc (4×20 ml). The combined organic phase was collected, dried over Na$_2$SO$_4$, filtered and concentrated under reduced pressure yielding di-tert-butyl 1-(1-phenyl-1H-imidazol-4-yl)hydrazine-1,2-dicarboxylate (1.0 g, 2.67 mmol). LCMS: Method 1, 2.238 min, MS: ES+ 375.0.

Step c. Di-tert-butyl 1-(1-phenyl-1H-imidazol-4-yl)hydrazine-1,2-dicarboxylate (1.15 g, 3.073 mmol) was stirred in 4M HCl in 1,4-dioxane (5 ml) at rt for 30 min. The resulting reaction mixture was concentrated under reduced pressure yielding 4-hydrazinyl-1-phenyl-1H-imidazole HCl salt (1.15 g, quantitative). LCMS: Method 1, 1.507 min, MS: ES+ 175.19.

Intermediate D 4-Hydrazinyl-1-phenyl-1H-pyrazole

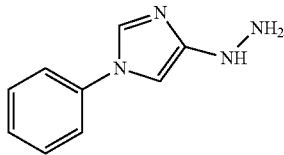 [SMILES: NNc1cn(-c2ccccc2)cn1]

Step a. To a solution of 4-nitro-1H-pyrazole (CAS Number 2075-46-9 available from Combi Blocks) (4.000 g, 35.4 mmol) in MeOH (30 ml) was added phenylboronic acid (7.700 g, 63.7 mmol). TEA (1.43 g, 14.16 mmol) was added to the reaction mixture at rt. The reaction mixture was purged with oxygen for 15 min at rt. $Cu_2O$ (0.500 g, 3.506 mmol) was added to the reaction mixture. The reaction mixture was heated at 65° C. for 34 h with continuous purging of oxygen. The resulting reaction mixture was cooled to rt, filtered through celite bed and washed with DCM:MeOH (1:1, 2×100 ml). The combined filtrate was dried over $Na_2SO_4$, filtered and concentrated under reduced pressure. The resulting residue was purified by column chromatography (100% DCM) yielding 4-nitro-1-phenyl-1H-pyrazole (3.400 g, 17.89 mmol). LCMS: Method 1, 2.071 min. No mass ion observed. This material was used directly for the next step without further purification.

Step b. To a solution of 4-nitro-1-phenyl-1H-pyrazole (0.600 g, 3.174 mmol) in EtOH:water (1:1, 10 ml) was added Fe powder (0.495 g, 9.52 mmol). AcOH (0.942 g, 15.7 mmol) was added to the reaction mixture at rt. The reaction mixture was heated at 80° C. for 2 h. The resulting reaction mixture was cooled to rt, filtered through celite bed and washed with MeOH (2×10 ml). The combined filtrate was concentrated under reduced pressure yielding 1-phenyl-1H-pyrazol-4-amine (0.500 g, 3.144 mmol). LCMS: Method 1, 1.341 min, MS: ES+ 160.14. This material was used directly for the next step without further purification.

Step c. To a solution of 1-phenyl-1H-pyrazol-4-amine (0.500 g, 3.144 mmol) in concentrated HCl (5 ml) was added solution of $NaNO_2$ (0.260 g, 3.768 mmol) in water (2 ml) at 0° C. The resulting reaction mixture was stirred at 0° C. for 1 h. A solution of $SnCl_2.2H_2O$ (1.780 g, 9.418 mmol) in concentrated HCl (5 ml) was added to the above reaction mixture at 0° C. The resulting reaction mixture was stirred at rt for 2 h. The obtained precipitates were collected by filtration and dried under vacuum yielding 4-hydrazinyl-1-phenyl-1H-pyrazole (1.000 g, quantitative). LCMS: Method 1, 1.339 min, MS: ES+ 175.19. This material was used directly for the next step without further purification.

Intermediate E 1-(3-Fluoro-4-(4,4,5,5-tetramethyl-1,3,2-dioxaborolan-2-yl)phenyl)-4-methylpiperazine

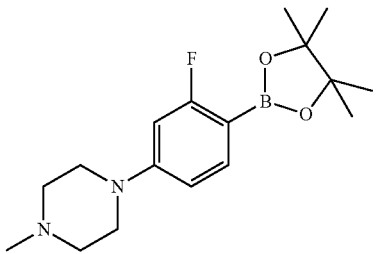

Step a. To a solution of 4-bromo-3-fluoroaniline (CAS Number 656-65-5; 1.000 g, 5.292 mmol) in EtOH (30 ml) were added TEA (2.21 ml, 15.9 mmol) followed by chlormethine hydrochloride (CAS Number 55-86-7; 2.037 g, 10.58 mmol) at rt. The reaction mixture was heated at 100° C. for 18 h. The reaction mixture was combined with one other batch prepared on the same scale by an identical method. The resulting mixture was cooled to rt, filtered and the filtrate was concentrated under reduced pressure. The residue was purified by flash column chromatography (90% EtOAc in n-hexane and further 10% MeOH in DCM) yielding 1-(4-bromo-3-fluorophenyl)-4-methylpiperazine (0.680 g, 2.500 mmol). LCMS: Method 1, 1.470 min, MS: ES+ 273.28, 275.28.

Step b. To a stirred solution of 1-(4-bromo-3-fluorophenyl)-4-methylpiperazine (0.680 g, 2.50 mmol) in toluene (30 ml) were added $K_2CO_3$ (0.690 g, 5.00 mmol) and bispinacolatodiboron (0.950 g, 3.75 mmol) at rt. The reaction mixture was degassed for 10 min before addition of $Pd(PPh_3)_4$ (0.289 g, 0.250 mmol) at rt. The reaction mixture was heated at 100° C. for 8 h. The resulting mixture was cooled to rt, filtered under vacuum and the filtrate was concentrated under reduced pressure. The residue was purified by flash column chromatography (100% n-hexane) to yield 1-(3-fluoro-4-(4,4,5,5-tetramethyl-1,3,2-dioxaborolan-2-yl)phenyl)-4-methylpiperazine (0.980 g, quantitative). LCMS: Method 1, 1.554 min, MS: ES+ 321.53.

Intermediate F 3-(3-(4,4,5,5-Tetramethyl-1,3,2-dioxaborolan-2-yl)phenyl)oxazolidin-2-one

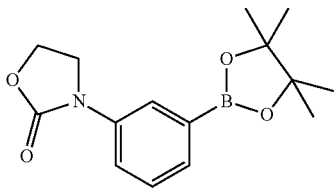 [SMILES: CC1(C)OB(c2cccc(N3CCOC3=O)c2)OC1(C)C]

To a stirred solution of 3-(3-bromophenyl)oxazolidin-2-one (CAS Number 1086221-37-5; 0.600 g, 2.489 mmol) in 1,4-dioxane (10 ml) was added KOAc (0.488 g, 4.98 mmol) and bispinacolatodiboron (0.948 g, 3.734 mmol) at rt. The reaction mixture was degassed for 15 min before addition of $PdCl_2(dppf)$ (0.181 g, 0.248 mmol) at rt. The resulting reaction mixture was heated at 100° C. for 2 h. The reaction mixture was combined with one other batch prepared on the same scale by an identical method. The reaction mixture was cooled to rt and poured into water (70 ml). The resulting mixture was extracted with EtOAc (3×50 ml). The combined organic phase was dried over Na$_2$SO$_4$, filtered and concentrated under reduced pressure yielding 3-(3-(4,4,5,5-tetramethyl-1,3,2-dioxaborolan-2-yl)phenyl)oxazolidin-2-one (1.500 g). This material was directly used for next step without any further purification.

Scheme 1

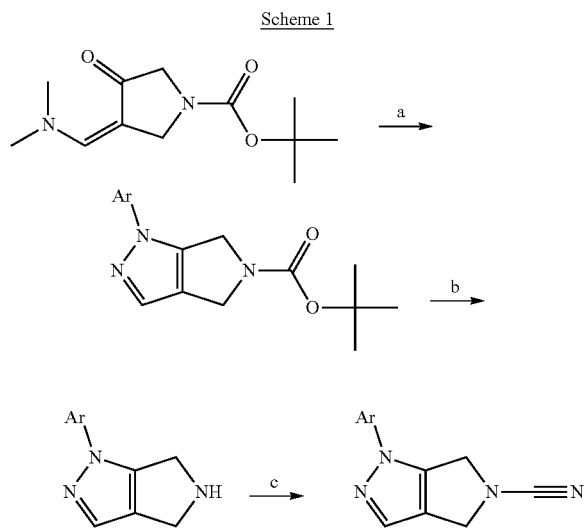

Reagents and conditions: a) Ar—NHNH$_2$, EtOH, cat. AcOH; b) 4M HCl in 1,4-dioxane; c) BrCN, K$_2$CO$_3$.

Example 1 1-(4-Methoxyphenyl)-4,6-dihydropyrrolo[3,4-c]pyrazole-5(1H)-carbonitrile Synthesised According to Scheme 1

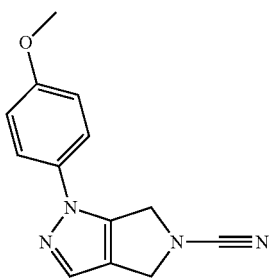 [SMILES: COc1ccc(-n2ncc3c2CN(C#N)C3)cc1]

Step a. To a solution of tert-butyl (Z)-3-((dimethylamino)methylene)-4-oxopyrrolidine-1-carboxylate (Intermediate A, 0.3 g, 1.250 mmol) and (4-methoxyphenyl)hydrazine hydrochloride (CAS Number 19501-58-7, available from Spectrochem) (0.66 g, 3.750 mmol) in EtOH (10 ml) was added AcOH (0.1 ml) at rt. The reaction mixture was stirred at rt for 10 min and then heated at 80° C. for 4 h. The resulting reaction mixture was cooled to rt, diluted with water (50 ml) and extracted with EtOAc (2×50 ml). The combined organic phase was washed with brine (30 ml) and dried over Na$_2$SO$_4$, filtered and concentrated under reduced pressure. The resulting residue was purified by flash chromatography (30% EtOAc in hexane) yielding tert-butyl 1-(4-methoxyphenyl)-4,6-dihydropyrrolo[3,4-c]pyrazole-5(1H)-carboxylate (0.20 g, 0.634 mmol). LCMS: Method 1, 2.314 min, MS: ES+ 316.33.

Step b. A solution of tert-butyl 1-(4-methoxyphenyl)-4,6-dihydropyrrolo[3,4-c]pyrazole-5(1H)-carboxylate (0.15 g, 0.474 mmol) in 4M HCl in 1,4-dioxane (5 ml) was stirred at rt for 30 min. The resulting reaction mixture was concentrated under reduced pressure. The obtained residue was azeotropically distilled with diethyl ether (20 ml) and dried under high vacuum yielding 1-(4-methoxyphenyl)-1,4,5,6-tetrahydropyrrolo[3,4-c]pyrazole HCl salt (0.08 g, 0.318 mmol). LCMS: Method 1, 1.416 min, MS: ES+ 216.23.

Step c. To a solution of 1-(4-methoxyphenyl)-1,4,5,6-tetrahydropyrrolo[3,4-c]pyrazole HCl salt (0.075 g, 0.347 mmol) in a mixture of THF:MeOH (10 ml+1 ml) was added K$_2$CO$_3$ (0.14 g, 1.041 mmol) at rt. The reaction mixture was stirred at rt for 10 min. Cyanogen bromide (0.074 g, 0.694 mmol) was added to the reaction mixture at rt. The reaction mixture was stirred at rt for 1 h. The resulting reaction mixture was poured into saturated NaHCO$_3$ solution (20 ml) and extracted with EtOAc (2×30 ml). The combined organic phase was washed with brine (20 ml), dried over Na$_2$SO$_4$, filtered and concentrated under reduced pressure. The resulting residue was purified by flash chromatography (15% EtOAc in n-hexane) yielding the title compound (0.025 g, 0.104 mmol). LCMS: Method 3, 5.586 min, MS: ES+ 241.15; $^1$H NMR (400 MHz, DMSO-d6) δ ppm 7.51-7.54 (m, 3H), 7.054 (d, J=8.8 Hz, 2H), 4.97 (s, 2H), 4.58 (s, 2H), 3.79 (s, 3H).

Compounds in Table 1 were synthesised using a procedure similar to that described for Example 1.

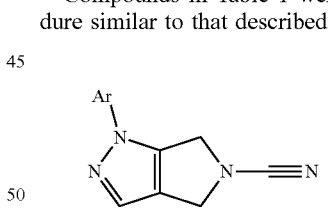

TABLE 1

| Ex | Ar— | Name | Aryl hydrazine CAS Number | LCMS method | LCMS RT | MS ES+ |
|---|---|---|---|---|---|---|
| Example 2 | phenyl | 1-Phenyl-4,6-dihydropyrrolo[3,4-c]pyrazole-5(1H)-carbonitrile | 100-63-0 | 2 | 5.444 min | 211.13 |

TABLE 1-continued

| Ex | Ar— | Name | Aryl hydrazine CAS Number | LCMS method | LCMS RT | MS ES+ |
|---|---|---|---|---|---|---|
| Example 3 | 4-fluorophenyl | 1-(4-Fluorophenyl)-4,6-dihydropyrrolo[3,4-c]pyrazole-5(1H)-carbonitrile | 371-14-2 | 3 | 5.656 min | 229.10 |
| Example 4 | 2-fluorophenyl | 1-(2-Fluorophenyl)-4,6-dihydropyrrolo[3,4-c]pyrazole-5(1H)-carbonitrile | 2368-80-1 | 4 | 3.677 min | 229.00 |
| Example 5 | 4-carbamoylphenyl | 4-(5-Cyano-5,6-dihydropyrrolo[3,4-c]pyrazol-1(4H)-yl)benzamide | 74885-67-9 | 3 | 4.408 min | 254.15 |
| Example 6 | quinolin-3-yl | 1-(Quinolin-3-yl)-4,6-dihydropyrrolo[3,4-c]pyrazole-5(1H)-carbonitrile | 15793-78-9 | 6 | 3.406 min | 262.07 |
| Example 7 | 3-methoxyphenyl | 1-(3-Methoxyphenyl)-4,6-dihydropyrrolo[3,4-c]pyrazole-5(1H)-carbonitrile | 15384-39-1 | 6 | 3.573 min | 241.06 |
| Example 8 | 1-phenyl-1H-pyrazol-4-yl | 1-(1-Phenyl-1H-pyrazol-4-yl)-4,6-dihydropyrrolo[3,4-c]pyrazole-5(1H)-carbonitrile | Intermediate D | 6 | 3.722 min | 277.28 |
| Example 9 | 1-phenyl-1H-imidazol-4-yl | 1-(1-Phenyl-1H-imidazol-4-yl)-4,6-dihydropyrrolo[3,4-c]pyrazole-5(1H)-carbonitrile | Intermediate C | 4 | 3.796 min, 3.952 min | 277.02, 277.02 |

Example 10 3-Methyl-1-phenyl-4,6-dihydropyrrolo[3,4-c]pyrazole-5(1H)-carbonitrile

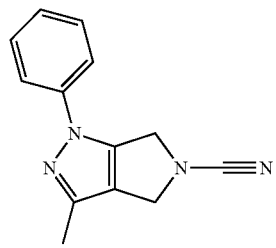 [SMILES: Cc1nn(-c2ccccc2)c2c1CN(C#N)C2]

Synthesised using a procedure similar to that described for Example 1, using intermediate B in place of intermediate A. LCMS Method 4, 4.038 min, MS: ES+ 225.05.

Scheme 2

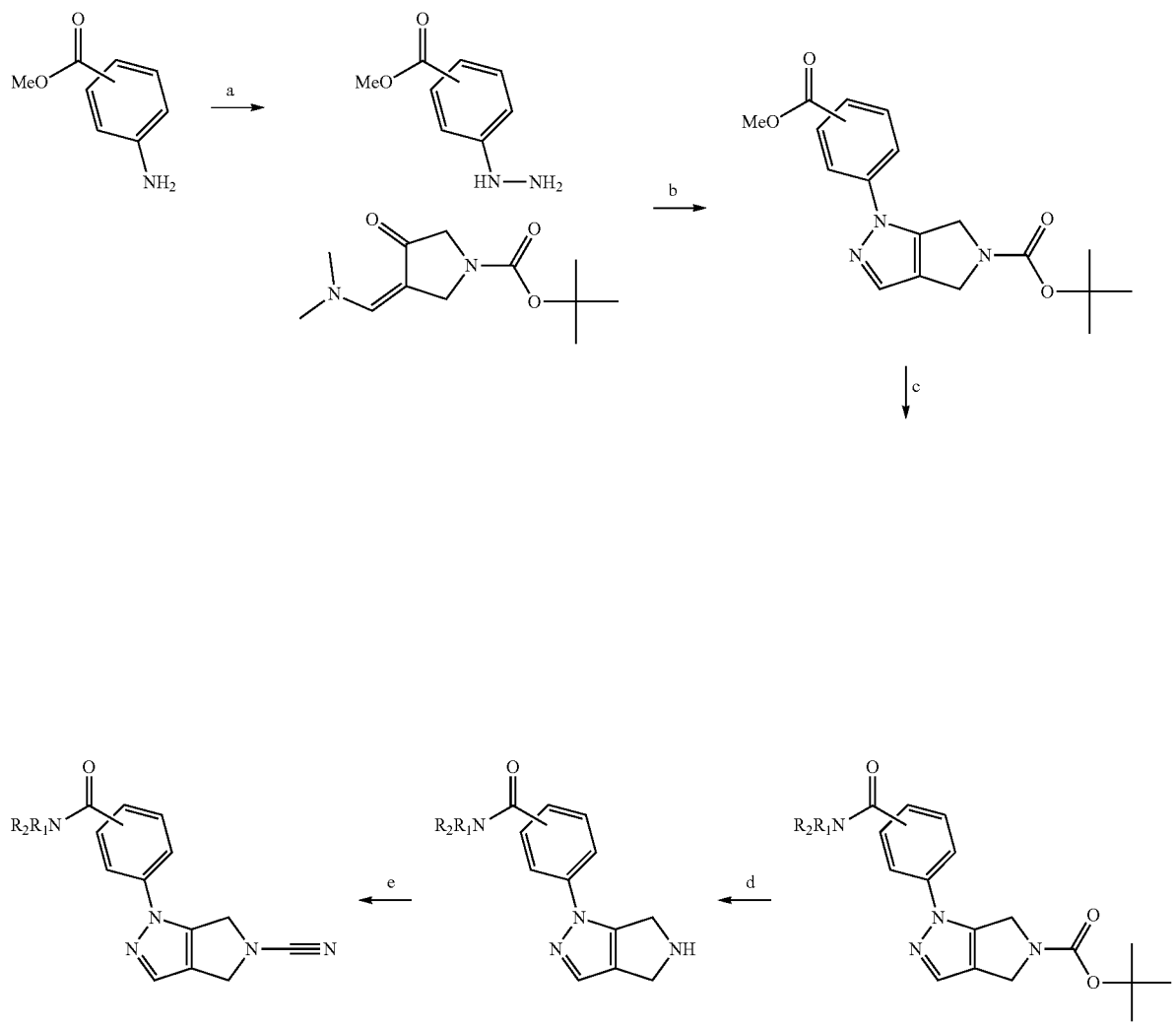

Reagents and conditions: a) Conc. HCl, NaNO₂, SnCl₂; b) Ar—NHNH₂, EtOH, cat. AcOH; c) R₁R₂NH, Me₃Al, DIPEA, THF; d) TFA, DCM; e) BrCN, K₂CO₃.

Example 11 N-Benzyl-3-(5-cyano-5,6-dihydropyrrolo[3,4-c]pyrazol-1(4H)-yl)benzamide Synthesised According to Scheme 2

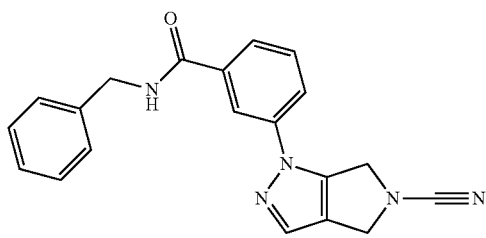 [SMILES: N#CN1Cc2cnn(-c3cccc(C(=O)NCc4ccccc4)c3)c2C1]

Step a. A mixture of methyl 3-aminobenzoate (CAS Number 4518-10-9, available from Combi Blocks) (8 g, 52.9 mmol) in concentrated HCl (70 ml) was cooled to 0° C. A solution of NaNO₂ (4.38 g, 63.4 mmol) in water (5 ml) was added to the reaction mixture at 0° C. and stirred for 30 min. A mixture of SnCl₂ (30 g, 158 mmol) in HCl (30 ml) was added to the reaction mixture at 0° C. The reaction mixture was stirred at a temperature between 0 to 10° C. for 2 h. The resulting solids were filtered off under vacuum, washed with diethyl ether (2×5 ml) and finally dried to yield methyl 3-hydrazinylbenzoate (30 g, crude). LCMS: Method 4, 2.806 min, MS: ES+ 167.07. This material was used directly for the next step without further purification.

Step b. To a solution of tert-butyl (Z)-3-((dimethylamino)methylene)-4-oxopyrrolidine-1-carboxylate (Intermediate A, 6 g, 25 mmol) in EtOH (30 ml) was added methyl 3-hydrazinylbenzoate (4.98 g, 30 mmol) at rt. Glacial AcOH (2 ml) was added to the reaction mixture at rt. The reaction mixture was heated at 80° C. for 16 h. The resulting reaction mixture was cooled to rt and poured into saturated aqueous NaHCO₃ solution (80 ml). The obtained mixture was extracted with EtOAc (2×50 ml). The combined organic phase was washed with brine (100 ml), dried over Na₂SO₄, filtered and concentrated under reduced pressure. The resulting residue was purified by column chromatography (20% EtOAc in hexane) yielding tert-butyl 1-(3-(methoxycarbonyl)phenyl)-4,6-dihydropyrrolo[3,4-c]pyrazole-5(1H)-carboxylate (1.7 g, 4.95 mmol). LCMS: Method 1, 2.423 min, MS: ES+ 344.3

Step c. To a solution of tert-butyl 1-(3-(methoxycarbonyl) phenyl)-4,6-dihydropyrrolo[3,4-c]pyrazole-5(1H)-carboxylate (0.7 g, 2.04 mmol) in THF (10 ml) was added DIPEA (0.17 ml, 1.02 mmol) at 0° C. Trimethylaluminium (2 M in toluene; 5.10 ml, 10.20 mmol) was added to the reaction mixture at 0° C. and stirred for 15 min. Benzylamine (0.27 g, 2.44 mmol) was added to the reaction mixture at 0° C. The reaction mixture was heated at 50° C. for 6 h. The resulting reaction mixture was cooled to rt and poured into saturated NaHCO$_3$ solution (80 ml) and extracted with EtOAc (2×20 ml). The combined organic phase was dried over Na$_2$SO$_4$, filtered and concentrated under reduced pressure. The resulting residue was purified by column chromatography (37% EtOAc in hexane) yielding tert-butyl 1-(3-(benzylcarbamoyl)phenyl)-4,6-dihydropyrrolo[3,4-c]pyrazole-5(1H)-carboxylate (0.15 g, 0.35 mmol). LCMS: Method 1, 2.342 min, MS: ES+ 419.33

Step d. To a solution of tert-butyl 1-(3-(benzylcarbamoyl) phenyl)-4,6-dihydropyrrolo[3,4-c]pyrazole-5(1H)-carboxylate (0.15 g, 0.35 mmol) in DCM (5 ml) was added TFA (1.5 ml) at 0° C. The reaction mixture was stirred at rt for 4 h. The resulting reaction mixture was concentrated under reduced pressure to yield N-benzyl-3-(5,6-dihydropyrrolo[3,4-c] pyrazol-1(4H)-yl)benzamide TFA Salt (0.3 g, quantitative). LCMS: Method 1, 1.541 min, MS: ES+ 319.23. This material was used directly for the next step without further purification.

Step e. To a solution of N-benzyl-3-(5,6-dihydropyrrolo [3,4-c]pyrazol-1(4H)-yl)benzamide TFA Salt (0.3 g, 0.69 mmol) in THF (5 ml) was added K$_2$CO$_3$ (0.52 g, 3.77 mmol) at 0° C. Cyanogen bromide (0.099 g, 0.94 mmol) was added at 0° C. The reaction mixture was stirred for 1 h at rt. The resulting reaction mixture was poured into water (20 ml) and extracted with EtOAc (2×5 ml). The combined organic phase was dried over Na$_2$SO$_4$, filtered and concentrated under reduced pressure. The resulting residue was purified by column chromatography (62% EtOAc in hexane) to yield N-benzyl-3-(5-cyano-5,6-dihydropyrrolo[3,4-c]pyrazol-1 (4H)-yl)benzamide (0.042 g, 0.122 mmol). LCMS: Method 4, 3.993 min, MS: ES+ 343.9; $^1$H NMR (400 MHz, DMSO-d6) δ ppm 9.24 (t, J=6 Hz, 1H), 8.11 (s, 1H), 7.85 (d, J=8 Hz, 1H), 7.72 (dd, J=1.2, 8 Hz, 1H), 7.59-7.65 (m, 2H), 7.31-7.40 (m, 4H), 7.24-7.27 (m, 1H), 5.08 (s, 2H), 4.60 (s, 2H), 4.51 (d, J=5.6 Hz, 2H).

Compounds in Table 2 were synthesised using a procedure similar to that described for Example 11, varying the amine used in step c.

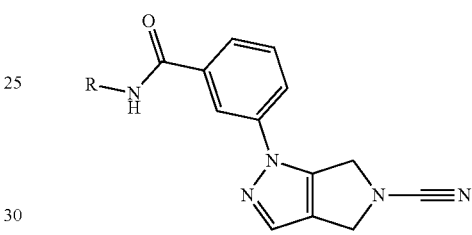

TABLE 2

| Ex | R | Name | Amine CAS Number | LCMS method | LCMS RT | MS ES+ |
|---|---|---|---|---|---|---|
| Example 12 | ![structure] | 3-(5-Cyano-5,6-dihydropyrrolo[3,4-c]pyrazol-1(4H)-yl)-N-(1-phenylethyl)benzamide | 618-36-0 | 4 | 4.181 min | 357.90 |
| Example 13 | ![structure] | 3-(5-Cyano-5,6-dihydropyrrolo[3,4-c]pyrazol-1(4H)-yl)-N-(pyridin-2-ylmethyl)benzamide | 3731-51-9 | 4 | 3.252 min | 344.98 |

Compounds in Table 3 were synthesised using a procedure similar to that described for Example 11 using methyl 4-aminobenzoate (CAS Number 619-45-4) in step a.

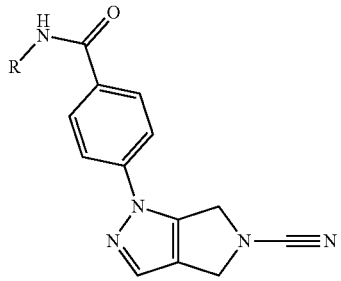

Intermediate B in step b and methanolic ammonia in step c. LCMS: Method 1, 1.729 min, MS: ES+ 268.18.

Scheme 3

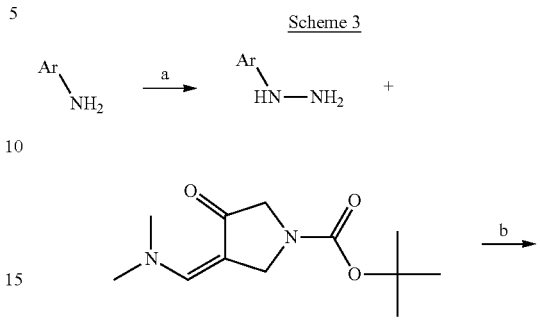

TABLE 3

| Ex | R— | Name | Amine CAS Number | LCMS method | LCMS RT/ min | MS ES+ |
|---|---|---|---|---|---|---|
| Example 14 | pyridin-2-ylmethyl | 4-(5-Cyano-5,6-dihydro-pyrrolo[3,4-c]pyrazol-1(4H)-yl)-N-(pyridin-2-ylmethyl)benzamide | 3731-51-9 | 6 | 2.635 min | 345.38 |
| Example 15 | CH₃ | 4-(5-Cyano-5,6-dihydropyrrolo[3,4-c]pyrazol-1(4H)-yl)-N-methylbenzamide | 74-89-5 | 12 | 7.208 min | 268.15 |

Example 16 4-(5-Cyano-3-methyl-5,6-dihydropyrrolo[3,4-c]pyrazol-1(4H)-yl)benzamide

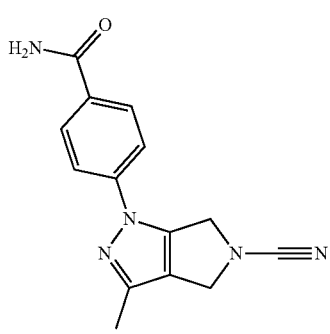 [SMILES: Cc1nn(-c2ccc(C(N)=O)cc2)c2c1CN(C#N)C2]

Synthesised using a procedure similar to that described for Example 11, using ethyl 4-aminobenzoate in step a, -continued

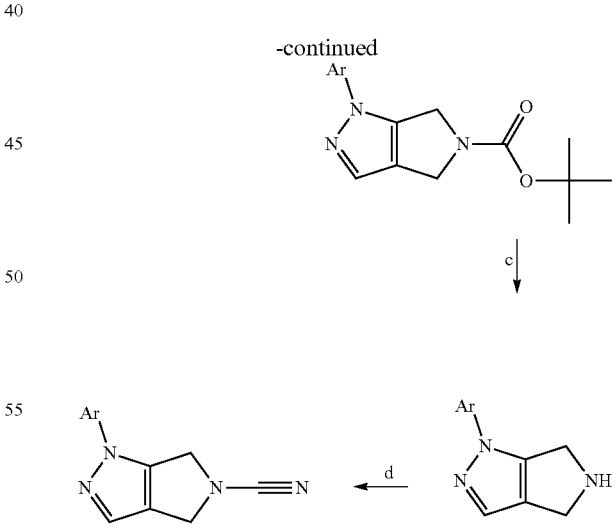

Reagents and conditions: a) Conc. HCl, NaNO₂, SnCl₂•2H₂O; b) EtOH, cat. AcOH; c) 4M HCl in 1,4 -dioxane; d) BrCN, K₂CO₃.

Compounds in Table 4 were synthesised according to scheme 3, with step a using a procedure similar to step a of Example 12, and steps b-d using a procedure similar to that described for steps a-c of Example 1.

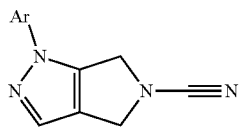

TABLE 4

| Ex | Ar— | Name | Amine CAS Number | LCMS method | LCMS RT | MS ES+ |
|---|---|---|---|---|---|---|
| Example 17 | 1-methyl-1H-indazol-5-yl | 1-(1-Methyl-1H-indazol-5-yl)-4,6-dihydropyrrolo[3,4-c]pyrazole-5(1H)-carbonitrile | 50593-24-3 | 6 | 3.208 min | 265.18 |
| Example 18 | 2-methoxy-5-(N-methylcarbamoyl)phenyl | 5-(5-Cyano-5,6-dihydropyrrolo[3,4-c]pyrazol-1(4H)-yl)-2-methoxy-N-methylbenzamide | 194025-85-9 | 5 | 3.467 min | 298.05 |
| Example 19 | 1H-indazol-3-yl | 1-(1H-Indazol-3-yl)-4,6-dihydropyrrolo[3,4-c]pyrazole-5(1H)-carbonitrile | 874-05-5 | 4 | 4.008 min | 251.00 |
| Example 20 | 3-phenyl-1H-pyrazol-5-yl | 1-(3-Phenyl-1H-pyrazol-5-yl)-4,6-dihydropyrrolo[3,4-c]pyrazole-5(1H)-carbonitrile | 1572-10-7 | 4 | 3.983 min | 277.00 |

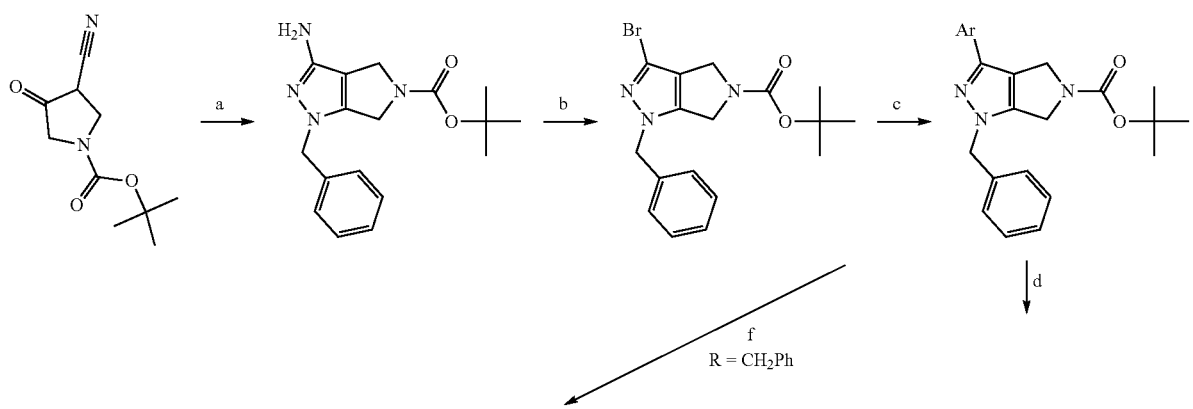

Scheme 4

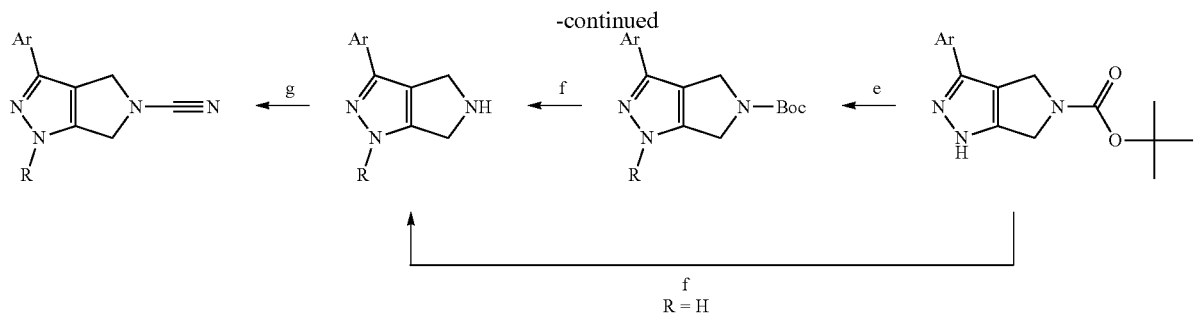

Reagents and conditions: a) i) BnNHNH₂, EtOH, cat. AcOH; ii) Boc₂O, TEA; b) CuBr₂, isoamylnitrile, MeCN; c) ArB(OH)₂, Pd(PPh₃)₄, 1,4-dioxane, water; d) polymethylhydroxysilane 20% Pd(OH)₂/C, EtOH; e) RBr, Cs₂CO₃, DMF f) TFA, DCM; g) BrCN, K₂CO₃.

Example 21 1-Methyl-3-phenyl-4,6-dihydropyrrolo[3,4-c]pyrazole-5(1H)-carbonitrile Synthesised According to Scheme 4

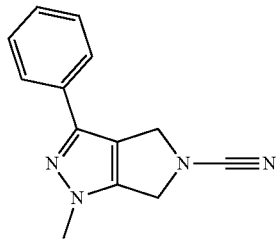 [SMILES: Cn1nc(-c2ccccc2)c2c1CN(C#N)C2]

Step a. A solution of tert-butyl 3-cyano-4-oxopyrrolidine-1-carboxylate (CAS Number 175463-32-8, available from Combi blocks) (5.0 g, 23.81 mmol) and benzylhydrazine di-hydrochloride (CAS Number 20570-96-1, available from Combi blocks) (9.27 g, 47.62 mmol) in EtOH (50 ml) was heated at 70° C. for 1 h. The resulting reaction mixture was cooled to rt. (Boc)₂O (10.39 g, 47.62 mmol) and TEA (7.2 g, 71.43 mmol) were added to the reaction mixture at rt. The reaction mixture was stirred at rt for 1 h. The resulting reaction mixture was poured into saturated NaHCO₃ solution (25 ml) and extracted with EtOAc (2×100 ml). The combined organic phase was collected, dried over Na₂SO₄, filtered and concentrated under reduced pressure. The resulting residue was purified by flash chromatography (2% MeOH in DCM) yielding tert-butyl 3-amino-1-benzyl-4,6-dihydropyrrolo[3,4-c]pyrazole-5(1H)-carboxylate (3.0 g, 9.55 mmol). LCMS: Method 1, 2.126 min, MS: ES+ 314.9; ¹H NMR (400 MHz, DMSO-d6) δ ppm 7.29-7.32 (m, 2H), 7.22-7.25 (m, 1H), 7.14-7.16 (m, 2H), 5.47 (s, 2H), 5.07 (d, J=3.2 Hz, 2H), 4.17 (s, 2H), 4.14 (d, J=6.4 Hz, 2H), 1.43 (s, 9H).

Step b. To a solution of tert-butyl 3-amino-1-benzyl-4,6-dihydropyrrolo[3,4-c]pyrazole-5(1H)-carboxylate (1.0 g, 3.182 mmol) in MeCN (10 ml) was added CuBr₂ (1.06 g, 4.774 mmol) at rt under argon atmosphere. The reaction mixture was stirred at rt for 15 min. Isoamyl nitrite (0.6 g, 4.774 mmol) was added to the reaction mixture at rt. The reaction mixture was stirred at rt for 3 h. The resulting reaction mixture was combined with two other batches prepared on the same scale by an identical method. The resulting reaction mixture was quenched by 2M HCl (10 ml) and extracted with EtOAc (2×50 ml). The combined organic phase was wash with brine (10 ml), saturated NaHCO₃ solution, dried over Na₂SO₄, filtered and concentrated under reduced pressure. The resulting residue was purified by flash chromatography (50% EtOAc in hexane) yielding tert-butyl 1-benzyl-3-bromo-4,6-dihydropyrrolo[3,4-c]pyrazole-5(1H)-carboxylate (1.5 g, 3.978 mmol). LCMS: Method 1, 2.760 min, MS: ES+ 378.2; ¹H NMR (400 MHz, CDCl₃) δ ppm 7.23-7.39 (m, 5H), 5.33 (d, J=14.8 Hz, 2H), 4.50 (d, J=24.8 Hz, 2H), 4.39 (d, J=11.2 Hz, 2H), 1.52 (s, 9H).

Step c. A solution of tert-butyl 1-benzyl-3-bromo-4,6-dihydropyrrolo[3,4-c]pyrazole-5(1H)-carboxylate (1.5 g, 3.978 mmol) and phenylboronic acid (0.72 g, 5.967 mmol) in 1,4-dioxane:water (8:2) (20 ml) was degassed with nitrogen for 30 min at rt. Tetrakis(triphenylphosphine)palladium (0) (0.91 g, 0.795 mmol) and K₂CO₃ (1.14 g, 9.94 mmol) were added to the reaction mixture at rt. The reaction mixture was heated at 90° C. for 6 h. The resulting reaction mixture was cooled to rt. The resulting reaction mixture was poured into water (20 ml) and extracted with EtOAc (3×50 ml). The combined organic phase was dried over Na₂SO₄, filtered and concentrated under reduced pressure. The resulting residue was purified by flash chromatography (20% EtOAc in hexane) yielding tert-butyl 1-benzyl-3-phenyl-4,6-dihydropyrrolo[3,4-c]pyrazole-5(1H)-carboxylate (1.5 g, quantitative). LCMS: Method 1, 2.840 min, MS: ES+ 376.40.

Step d. To a solution of tert-butyl 1-benzyl-3-phenyl-4,6-dihydropyrrolo[3,4-c]pyrazole-5(1H)-carboxylate (0.5 g, 1.3 mmol) in EtOH (10 ml) was added 20% Pd(OH)₂ (50% moisture) (0.25 g) at rt. Poly(methylhydrosiloxane) (0.5 g) was added to the reaction mixture at 0° C. and the reaction mixture was stirred at rt for 24 h. The resulting reaction mixture was combined with two batches prepared on the same scale by an identical method. The reaction mixture was filtered through celite pad and washed with EtOH (5 ml). The resulting filtrate was concentrated under reduced pressure. The resulting residue was purified by flash chromatography (10% MeOH in DCM) yielding tert-butyl 3-phenyl-4,6-dihydropyrrolo[3,4-c]pyrazole-5(1H)-carboxylate (1.10 g, 3.86 mmol). LCMS: Method 1, 2.131 min, MS: ES+ 286.63.

Step e. To a solution of tert-butyl 3-phenyl-4,6-dihydropyrrolo[3,4-c]pyrazole-5(1H)-carboxylate (0.5 g, 1.754 mmol) in DMF (5 ml) was added Cs₂CO₃ (1.14 g, 3.508 mmol) at rt. Methyl iodide (0.33 ml, 5.26 mmol) was added drop wise to the reaction mixture at 0° C. The reaction mixture was stirred at rt for 1 h. The resulting reaction mixture was diluted with water (100 ml) and extracted with EtOAc (2×75 ml). The combined organic phase was dried over Na₂SO₄, filtered and concentrated under reduced pressure. The residue was purified by flash chromatography (10-11% EtOAc in hexane) yielding two regioisomeric products; tert-butyl 1-methyl-3-phenyl-4,6-dihydropyrrolo[3,4-c]pyrazole-5(1H)-carboxylate (0.04 g, 0.133 mmol): LCMS: Method 1, 2.355 min, MS: ES+ 300.42; $^1$H NMR (400 MHz, DMSO-d6) δ ppm 7.59 (t, J=6.8 Hz, 2H), 7.39-7.43 (m, 2H), 7.27-7.31 (m, 1H), 4.48-4.57 (m, 4H), 3.80 (d, J=2.8 Hz, 3H), 1.47 (s, 9H) and tert-butyl 2-methyl-3-phenyl-2,6-dihydropyrrolo[3,4-c]pyrazole-5(4H)-carboxylate (0.04 g, 0.133 mmol): LCMS: Method 1, 2.346 min, MS: ES+ 300.42; $^1$H NMR (400 MHz, DMSO-d6) δ ppm 7.23-7.59 (m, 5H), 4.42 (d, J=8.4 Hz, 2H), 4.37 (d, J=9.2 Hz, 2H), 3.86 (d, J=3.2 Hz, 3H), 1.45 (d, J=6 Hz, 9H). Regio chemistry was confirmed by NOE analysis.

Step f. To a solution of tert-butyl 1-methyl-3-phenyl-4,6-dihydropyrrolo[3,4-c]pyrazole-5(1H)-carboxylate (0.035 g, 0.120 mmol) in DCM (3 ml) was added TFA (0.35 ml) at rt. The reaction mixture was stirred at rt for 1 h. The resulting reaction mixture was concentrated under reduced pressure. The obtained residue was azeotropically distilled with diethyl ether (2 ml), triturated with diethyl ether (3 ml) and finally dried under high vacuum to yield 1-methyl-3-phenyl-1,4,5,6-tetrahydropyrrolo[3,4-c]pyrazole TFA salt (0.03 g, 0.095 mmol). LCMS: Method 1, 1.547 min, MS: ES+ 200.77. This material was used directly for the next step without further purification.

Step g. To a solution of 1-methyl-3-phenyl-1,4,5,6-tetrahydropyrrolo[3,4-c]pyrazole TFA salt (0.03 g, 0.095 mmol) in THF (3 ml) was added K$_2$CO$_3$ (0.03 g, 0.210 mmol) at rt. Cyanogen bromide (0.01 g, 0.096 mmol) was added to the reaction mixture at rt. The reaction mixture was stirred at rt for 30 min. The resulting reaction mixture was poured into water (30 ml) and extracted with EtOAc (2×25 ml). The combined organic phase was dried over Na$_2$SO$_4$, filtered and concentrated under reduced pressure. The resulting residue was purified by flash chromatography (2% MeOH in DCM) yielding the title compound (0.021 g, 0.093 mmol). LCMS: Method 4, 3.826 min, MS: ES+ 225.01; $^1$H NMR (400 MHz, DMSO-d6) δ ppm 7.58 (d, J=7.6 Hz, 2H), 7.40 (t, J=7.6 Hz, 2H), 7.31 (t, J=7.2 Hz, 2H), 4.79 (s, 2H), 4.69 (S, 2H), 3.79 (3H).

Example 22 2-Methyl-3-phenyl-2,6-dihydropyrrolo[3,4-c]pyrazole-5(4H)-carbonitrile

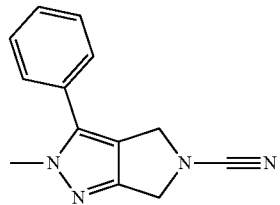 [SMILES: Cn1nc2c(c1-c1ccccc1)CN(C#N)C2]

Synthesised using a procedure similar to that described for Example 21, using tert-butyl 2-methyl-3-phenyl-2,6-dihydropyrrolo[3,4-c]pyrazole-5(4H)-carboxylate (prepared as described in steps a-e of Example 21). LCMS: Method 4, 3.857 min, MS: ES+ 225.01; $^1$H NMR (400 MHz, DMSO-d6) δ ppm 7.50-7.55 (m, 4H), 7.45-7.47 (m, 1H), 4.65 (s, 2H), 4.58 (s, 2H), 3.87 (s, 3H).

Example 23 1-Isopropyl-3-phenyl-4,6-dihydropyrrolo[3,4-c]pyrazole-5(1H)-carbonitrile

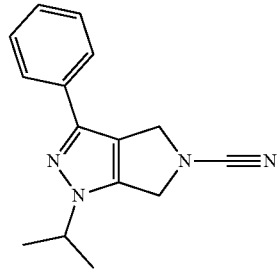 [SMILES: CC(C)n1nc(-c2ccccc2)c2c1CN(C#N)C2]

Synthesised using a procedure similar to that described for Example 21, using 2-bromopropane in step e. LCMS: Method 4, 4.515 min, MS: ES+ 253.0.

Compounds in Table 5 were synthesised using a procedure similar to that described for Example 21, omitting step e:

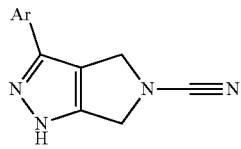

TABLE 5

| Ex | Ar— | Name | Boronic acid CAS Number | LCMS method | LCMS RT | MS ES+ |
|---|---|---|---|---|---|---|
| Example 24 | (phenyl) | 1-Benzyl-3-phenyl-4,6-dihydropyrrolo[3,4-c]pyrazole-5(1H)-carbonitrile | 98-80-6 | 4 | 4.780 min | 301.01 |

TABLE 5-continued

| Ex | Ar— | Name | Boronic acid CAS Number | LCMS method | LCMS RT | MS ES+ |
|---|---|---|---|---|---|---|
| Example 25 | | 1-Benzyl-3-(5-isopropyl-2-methoxyphenyl)-4,6-dihydropyrrolo[3,4-c]pyrazole-5(1H)-carbonitrile | 216393-63-4 | 4 | 5.521 min | 373.06 |
| Example 64 | | 3-(5-Ethyl-2-methoxyphenyl)-4,6-dihydropyrrolo[3,4-c]pyrazole-5(1H)-carbonitrile | 847345-37-3 | 15 | 3.49 | 269.2 |

Compounds in Table 6 were synthesised using a procedure similar to that described for Example 21, omitting steps d and e:

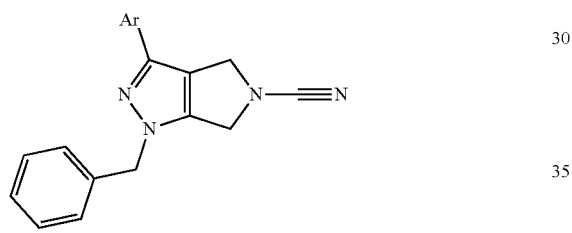

TABLE 6

| Ex | Ar— | Name | Boronic acid CAS Number | LCMS method | LCMS RT | MS ES+ |
|---|---|---|---|---|---|---|
| Example 26 | | 3-(5-Isopropyl-2-methoxyphenyl)-4,6-dihydropyrrolo[3,4-c]pyrazole-5(1H)-carbonitrile | 216393-63-4 | 4 | 4.527 min | 282.99 |
| Example 27 | | 3-(2-Fluoro-5-methylphenyl)-4,6-dihydropyrrolo[3,4-c]pyrazole-5(1H)-carbonitrile | 166328-16-1 | 4 | 3.873 min | 242.89 |

Example 28 5-(5-Cyano-5,6-dihydropyrrolo[3,4-c]pyrazol-1(4H)-yl)-1H-pyrazole-3-carboxamide

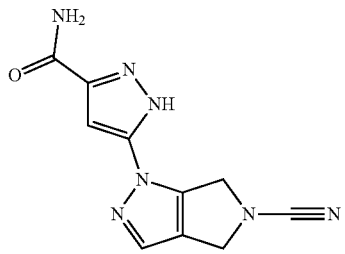 [SMILES: N#CN1Cc2cnn(-c3cc(C(N)=O)n[nH]3)c2C1]

Step a. To a solution of methyl 5-nitro-1H-pyrazole-3-carboxylate (CAS Number 181585-93-3, available from Ark Pharma) (0.200 g, 1.168 mmol) in MeOH (10 ml) was added 10% Pd/C (0.020 g, 10% w/w) at rt. The reaction mixture was purged with hydrogen gas at rt for 1 h. The resulting reaction mixture was carefully filtered through celite hyflow. The celite bed was washed with MeOH (2×5 ml) and the combined filtrate was concentrated under reduced pressure. The resulting residue was washed with pentane (2×5 ml) and dried under vacuum yielding methyl 5-amino-1H-pyrazole-3-carboxylate (0.185 g, 1.312 mmol). This material was used directly for the next step without further purification. LCMS: Method 4, 1.713 min, MS: ES+ 141.88

Step b. To a solution of methyl 5-amino-1H-pyrazole-3-carboxylate (0.150 g, 1.063 mmol) in concentrated HCl (2 ml) was added a solution of NaNO$_2$ (0.074 g, 1.084 mmol) in water (1.5 ml) at 0° C. The resulting reaction mixture was stirred at 0° C. for 30 min. A solution of SnCl$_2$ (0.403 g, 2.126 mmol) in concentrated HCl (3.3 ml) was added to above resulting mixture at 0° C. The reaction mixture was stirred at rt for 2 h. The resulting reaction mixture was concentrated under reduced pressure and co evaporated with EtOH (2×5 ml) yielding methyl 5-hydrazinyl-1H-pyrazole-3-carboxylate (0.158 g, 1.012 mmol). This material was used directly for the next step without further purification. LCMS: Method 1, 0.269 min, MS: ES+ 157.0

Step c. To a solution of tert-butyl (Z)-3-((dimethylamino)methylene)-4-oxopyrrolidine-1-carboxylate (Intermediate A, 0.200 g, 0.835 mmol) in EtOH (4 ml) was added methyl 5-hydrazinyl-1H-pyrazole-3-carboxylate (0.156 g, 1.000 mmol) at rt. Sodium tert-butoxide (0.170 g, 2.507 mmol) was added to the reaction mixture at rt. The reaction mixture was heated at 80° C. for 8 h. The resulting reaction mixture was cooled to rt and concentrated under reduced pressure. The resulting residue was triturated with n-pentane (2 ml), dried and purified by column chromatography (40% EtOAc in hexane) yielding tert-butyl 1-(3-(methoxycarbonyl)-1H-pyrazol-5-yl)-4,6-dihydropyrrolo[3,4-c]pyrazole-5(1H)-carboxylate (0.110 g, 0.330 mmol). LCMS: Method 1, 2.040 min, MS: ES+ 334.35.

Steps d-e. These were carried out using a procedure similar to that described for steps d-e of Example 11. LCMS: Method 4, 1.82 min, MS: ES+ 243.96.

Example 29 3-Phenyl-4,6-dihydropyrrolo[3,4-c]pyrazole-5(1H)-carbonitrile

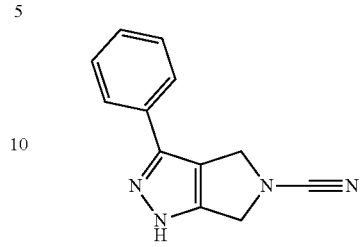

Step a. To a solution of tert-butyl 3-cyano-4-oxopyrrolidine-1-carboxylate (CAS Number 175463-32-8; 8.00 g, 38.1 mmol) in EtOH (85 ml) was added NH$_2$NH$_2$.2HCl (4.40 g, 41.9 mmol) at rt. The reaction mixture was heated at 80° C. for 30 min. The resulting mixture was concentrated under reduced pressure. The residue was poured into saturated NaHCO$_3$ solution (400 ml) and extracted with EtOAc (3×200 ml). The combined organic layer was dried over Na$_2$SO$_4$, filtered and concentrated under reduced pressure. The residue was purified by flash chromatography (4-5% MeOH in DCM) yielding tert-butyl 3-amino-4,6-dihydropyrrolo[3,4-c]pyrazole-5(1H)-carboxylate (2.600 g, 11.607 mmol). LCMS: Method 1, 1.657, 1.665 min, MS: ES+ 225.29.

Step b. To a solution of tert-butyl 3-amino-4,6-dihydropyrrolo[3,4-c]pyrazole-5(1H)-carboxylate (2.600 g, 11.607 mmol) in THF (30 ml) was added DIPEA (11.8 ml, 69.6 mmol) at 0° C. Ethyl chloroformate (1.11 ml, 11.72 mmol) was added dropwise to the reaction mixture at 0° C. The reaction mixture was stirred at 0° C. for 10 min and then at rt for 2 h. The reaction mixture was poured into water (60 ml) and extracted with EtOAc (3×60 ml). The combined organic layer was dried over Na$_2$SO$_4$, filtered and concentrated under reduced pressure. The residue was purified by flash chromatography (2-3% MeOH in DCM) yielding 5-tert-butyl 1-ethyl 3-amino-4,6-dihydropyrrolo[3,4-c]pyrazole-1,5-dicarboxylate (3.200 g, 10.81 mmol). LCMS: Method 1, 1.986, MS: ES+ 297.43.

Step c. To a solution of iodine (3.330 g, 13.120 mmol) in DCM (35 ml) was added isoamyl nitrite (2.95 ml, 21.99 mmol) at rt. 5-Tert-butyl 1-ethyl 3-amino-4,6-dihydropyrrolo[3,4-c]pyrazole-1,5-dicarboxylate (3.200 g, 10.81 mmol) was added to the reaction mixture at rt. The reaction mixture was stirred at rt for 1 h. The resulting reaction mixture was poured into saturated aqueous Na$_2$S$_2$O$_3$ solution (150 ml) and extracted with DCM (3×150 ml). The combined organic layer was dried over Na$_2$SO$_4$, filtered and concentrated under reduced pressure. The residue was purified by column chromatography (20-30% EtOAc in hexane) yielding 5-tert-butyl 1-ethyl 3-iodo-4,6-dihydropyrrolo[3,4-c]pyrazole-1,5-dicarboxylate (1.980 g, 4.86 mmol). LCMS: Method 1, 2.543 min, MS: ES+ 408.50

Step d. To a solution of 5-tert-butyl 1-ethyl 3-iodo-4,6-dihydropyrrolo[3,4-c]pyrazole-1,5-dicarboxylate (1.98 g, 4.86 mmol) in MeOH (16 ml) was added TEA (4 ml) at rt. The reaction mixture was stirred at rt for 30 min. The resulting reaction mixture was concentrated under reduced pressure yielding tert-butyl 3-iodo-4,6-dihydropyrrolo[3,4-c]pyrazole-5(1H)-carboxylate (1.630 g, 4.865 mmol). This material was used directly for the next step without further purification. LCMS: Method 1, 2.029 min, MS: ES+ 336.20;

$^1$H NMR (400 MHz, MeOD) δ ppm 4.49-4.51 (m, 2H), 4.31-4.34 (m, 2H), 1.53 (s, 9H).

Step e. To a solution of tert-butyl 3-iodo-4,6-dihydropyrrolo[3,4-c]pyrazole-5(1H)-carboxylate (1.630 g, 4.865 mmol) in DCM (18 ml) was added DMAP (0.891 g, 7.29 mmol) at 0° C. Boc anhydride (1.27 g, 5.82 mmol) was added to the reaction mixture at 0° C. and stirred for 10 min. The reaction mixture was then stirred at rt for 30 min. The resulting reaction mixture was poured into water (100 ml) and extracted with DCM (3×50 ml). The combined organic layer was dried over Na$_2$SO$_4$, filtered and concentrated under reduced pressure. The residue was purified by flash chromatography (20-30% EtOAc in hexane) yielding di-tert-butyl 3-iodo-4,6-dihydropyrrolo[3,4-c]pyrazole-1,5-dicarboxylate (1.070 g, 2.454 mmol). LCMS: Method 1, 2.772 min, MS: ES+ 436.50; $^1$H NMR (400 MHz, CDCl$_3$) δ ppm 4.69-4.72 (m, 2H), 4.33-4.36 (m, 2H), 1.53-1.65 (m, 18H).

Step f. To a solution of di-tert-butyl 3-iodo-4,6-dihydropyrrolo[3,4-c]pyrazole-1,5-dicarboxylate (0.500 g, 1.147 mmol) in 1,4-dioxane:water (4.5:0.5, 5 ml) prepared in a microwave tube was added phenylboronic acid (0.419 g, 3.434 mmol) at rt. K$_2$CO$_3$ (0.747 g, 3.435 mmol) was added to the reaction mixture at rt. The reaction mixture was degassed for 10-15 min. Tetrakis(triphenylphosphine)palladium(0) (0.132 g, 0.114 mmol) was added to reaction mixture at rt. The tube was sealed and reaction mixture was heated at 100° C. for 2 h in a microwave. The resulting mixture was cooled to rt, poured into water (30 ml) and extracted with EtOAc (3×30 ml). The combined organic phase was dried over Na$_2$SO$_4$, filtered and concentrated under reduced pressure. The resulting residue was purified by flash chromatography (34% MeOH in DCM) yielding tert-butyl 3-phenyl-4,6-dihydropyrrolo[3,4-c]pyrazole-5(1H)-carboxylate (0.170 g, 0.440 mmol). LCMS: Method 1, 2.165 min, MS: ES+ 286.29 (M-100); $^1$H NMR (400 MHz, DMSO-d6) δ ppm 13.11-13.21 (m, 1H), 7.59-7.62 (m, 2H), 7.46-7.50 (m, 2H), 7.31-7.41 (m, 1H), 4.34-4.38 (m, 2H), 4.21-4.13 (m, 2H), 1.44-1.48 (m, 9H).

Step g. To a solution of di-tert-butyl 3-phenyl-4,6-dihydropyrrolo[3,4-c]pyrazole-1,5-dicarboxylate (0.170 g, 0.44 mmol) in DCM (6 ml) was added TFA (3.5 ml) at 0° C. The reaction mixture was stirred at 0° C. for 10 min. The reaction mixture was stirred at rt for 2 h. The resulting reaction mixture was evaporated under reduced pressure. The residue was co evaporated with DCM (2×2 ml) and then triturated with diethyl ether (2×2 ml) and dried yielding 3-phenyl-1,4,5,6-tetrahydropyrrolo[3,4-c]pyrazole TFA salt (0.241 g, quantitative). This material was used directly for the next step without further purification. LCMS: Method 1, 1.447 min, MS: ES+ 186 07.

Step h. To a solution of 3-phenyl-1,4,5,6-tetrahydropyrrolo[3,4-c]pyrazole TFA salt (0.246 g, 0.596 mmol) in THF (5 ml) was added K$_2$CO$_3$ (0.250 g, 1.812 mmol) at 0° C. Cyanogen bromide (0.069 g, 0.651 mmol) was added to the reaction mixture at 0° C. The reaction mixture was stirred at 0° C. for 1 h. The resulting reaction mixture was poured into ice cold water (20 ml) and extracted with EtOAc (3×20 ml). The combined organic phase was dried over Na$_2$SO$_4$, filtered and concentrated under reduced pressure. The residue was purified by preparative TLC using 2.5% MeOH in DCM as mobile phase yielding the title compound (0.042 g, 0.20 mmol). LCMS: Method 6, 3.23 min, MS: ES+ 211.11; $^1$H NMR (400 MHz, DMSO-d6) δ ppm 13.34 (s, 1H), 7.58-7.65 (m, 3H), 7.53-7.55 (m, 2H), 7.38-7.49 (m, 1H), 4.79 (d, 2H), 4.57 (s, 2H).

Scheme 5

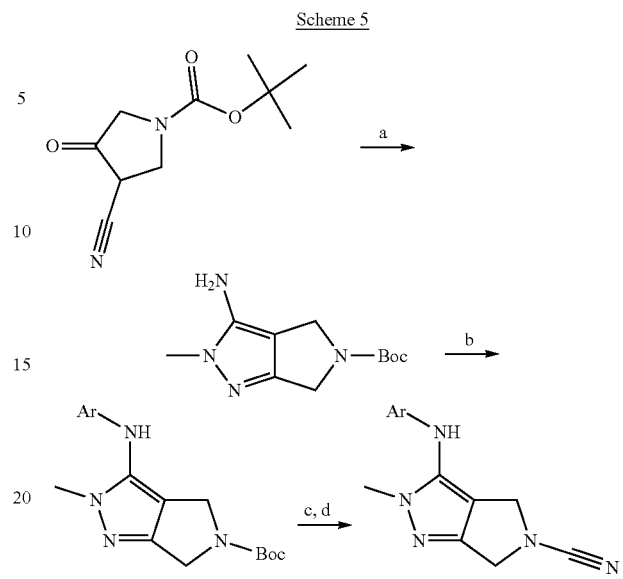

Reagents and conditions: a) RNHNH$_2$, EtOH; b) ArCl, Ruphos, Pd$_2$(dba)$_3$, KtBuO, toluene; c) TFA, DCM; d) BrCN, K$_2$CO$_3$.

Example 30 3-(Isoquinolin-3-ylamino)-2-methyl-2,6-dihydropyrrolo[3,4-c]pyrazole-5(4H)-carbonitrile Synthesised According to Scheme 5

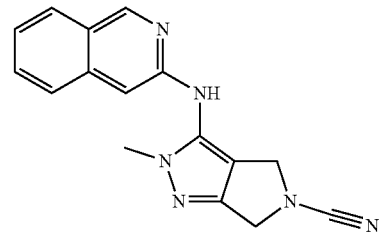 [SMILES: Cn1nc2c(c1Nc1cc3ccccc3cn1)CN(C#N)C2]

Step a. To a solution of tert-butyl 3-cyano-4-oxopyrrolidine-1-carboxylate (CAS Number 175463-32-8 available from Combi Blocks) (2.00 g, 9.52 mmol) in EtOH (20 ml) was added methyl hydrazine (0.44 g, 9.52 mmol) at rt. The reaction mixture was heated at 80° C. for 10 h. The resulting reaction mixture was cooled to rt and concentrated under reduced pressure. The residue was purified by column chromatography (42% EtOAc in hexane) yielding tert-butyl 3-amino-2-methyl-2,6-dihydropyrrolo[3,4-c]pyrazole-5(4H)-carboxylate (0.600 g, 2.521 mmol). LCMS: Method 1, 2.00 min, MS: ES+ 239.23; $^1$H NMR (400 MHz, DMSO-d6) δ ppm 4.97 (s, 2H), 4.20 (d, J=7.6 Hz, 2H), 4.09 (d, J=10.8 Hz, 2H), 3.18 (d, J=6.8 Hz, 3H), 1.41 (s, 9H). LCMS analysis showed an approximately 8:1 regioisomer ratio in favour of the desired isomer, confirmed by NOE analysis.

Step b. To a solution of tert-butyl 3-amino-2-methyl-2,6-dihydropyrrolo[3,4-c]pyrazole-5(4H)-carboxylate (0.700 g, 2.944 mmol) in toluene (5 ml) was added 3-chloroisoquinoline (CAS Number 19493-45-9; 0.400 g, 2.453 mmol), potassium tert-butoxide (0.549 g, 4.906 mmol) and Ru-Phos (0.114 g, 0.245 mmol) at rt. The reaction mixture was degassed for 15 min before addition of Pd$_2$(dba)$_3$ (0.224 g, 0.245 mmol). The reaction mixture was heated at 110° C. for 2.5 h. The resulting reaction mixture was cooled to rt. The reaction mixture was poured into water (50 ml) and extracted with EtOAc (4×20 ml). The combined organic phase was dried over Na$_2$SO$_4$, filtered and concentrated under reduced pressure. The resulting residue was purified by column chromatography (62% EtOAc in hexane) yielding tert-butyl 3-(isoquinolin-3-ylamino)-2-methyl-2,6-dihydropyrrolo[3,4-c]pyrazole-5(4H)-carboxylate (0.400 g, 1.095 mmol). LCMS: Method 1, 2.295 min, MS: ES+ 366.33.

Steps c, d. The title compound was synthesised from the intermediate above using a procedure similar to that described for steps g and h of Example 29. LCMS: Method 6, 3.530 min, MS: ES+ 290.80; $^1$H NMR (400 MHz, DMSO-d6) δ ppm 9.45 (s, 1H), 8.99 (s, 1H), 7.89 (d, J=8.4 Hz, 1H), 7.66 (d, J=8.4 Hz, 1H), 7.53-7.57 (m, 1H), 7.38 (s, 1H), 7.27-7.30 (m, 1H), 4.64 (d, 4H), 3.66 (s, 3H).

Example 31 3-(Isoquinolin-3-ylamino)-4,6-dihydropyrrolo[3,4-c]pyrazole-5(1H)-carbonitrile

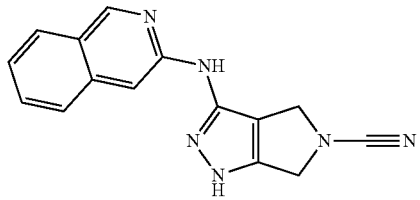 [SMILES: N#CN1Cc2[nH]nc(Nc3cc4ccccc4cn3)c2C1]

Step a. To a solution of tert-butyl 3-cyano-4-oxopyrrolidine-1-carboxylate (CAS Number 175463-32-8; 0.400 g, 1.904 mmol) in EtOH (5 ml) was added 4-methoxybenzylhydrazine HCl salt (CAS Number 2011-48-5; 0.718 g, 3.805 mmol) at rt. The resulting reaction mixture was heated at 70° C. for 1 h. The resulting reaction mixture was cooled to 0° C., neutralized with saturated NaHCO$_3$ solution (15 ml). The resulting reaction mixture was concentrated under reduced pressure to remove the EtOH. The residue was diluted with water (20 ml) and extracted with EtOAc (2×20 ml). The combined organic phase was washed with brine solution (20 ml), dried over Na$_2$SO$_4$, filtered and concentrated under reduced pressure yielding tert-butyl 3-amino-1-(4-methoxybenzyl)-4,6-dihydropyrrolo[3,4-c]pyrazole-5(1H)-carboxylate (0.500 g, 1.453 mmol). LCMS: Method 1, 1.962, MS: ES+ 345.50. This material was used directly for the next step without further purification.

Step b. This was carried out using the intermediate above by a procedure similar to that described for Example 30 step b giving tert-butyl 3-(isoquinolin-3-ylamino)-1-(4-methoxybenzyl)-4,6-dihydropyrrolo[3,4-c]pyrazole-5(1H)-carboxylate Step c. A solution of tert-butyl 3-amino-1-(4-methoxybenzyl)-4,6-dihydropyrrolo[3,4-c]pyrazole-5(1H)-carboxylate (0.200 g, 0.424 mmol) in TFA (2.0 ml) was heated at 70° C. for 16 h. The resulting reaction mixture was cooled to rt and concentrated under reduced pressure. The resulting residue was co evaporated with DCM (2×5 ml). The obtained residue was triturated with diethyl ether (2×10 ml) and finally dried under high vacuum yielding N-(1,4,5,6-tetrahydropyrrolo[3,4-c]pyrazol-3-yl)isoquinolin-3-amine (0.150 g, 0.410 mmol). LCMS: Method 1, 1.632 min, MS: ES+ 252.18.

Step d. The title compound was synthesized by using the intermediate mentioned above by a procedure similar to that described for step h of Example 29. LCMS: Method 1, 1.946 min, MS: ES+ 277.18; $^1$H NMR (400 MHz, DMSO-d6) δ ppm 12.09-12.32 (m, 1H), 9.45-9.56 (m, 1H), 9.00-9.05 (m, 1H), 7.91-7.93 (m, 1H), 7.65-7.75 (m, 1H), 7.44-7.57 (m, 2H), 7.30-7.35 (m, 1H), 4.51-4.63 (m, 4H).

Example 32 1-Benzyl-3-(isoquinolin-3-ylamino)-4,6-dihydropyrrolo[3,4-c]pyrazole-5(1H)-carbonitrile

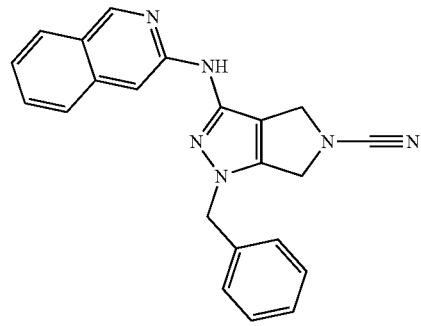 [SMILES: N#CN1Cc2c(Nc3cc4ccccc4cn3)nn(Cc3ccccc3)c2C1]

The title compound was synthesised using a procedure similar to that described for Example 31. LCMS: Method 1 RT 2.302 min, MS: ES+ 367.48.

Example 33 4-(5-Cyano-3-(pyridin-2-ylamino)-5,6-dihydropyrrolo[3,4-c]pyrazol-1(4H)-yl)benzamide

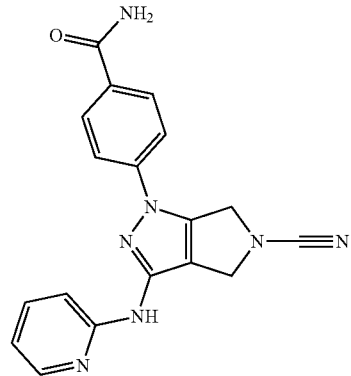 [SMILES: N#CN1Cc2c(Nc3ccccn3)nn(-c3ccc(C(N)=O)cc3)c2C1]

Step a. This was carried out using 4-carboxamidophenylhydrazine by a procedure similar to that described for step a of Example 31.

Step b. To a solution of tert-butyl 3-amino-1-(4-carbamoylphenyl)-4,6-dihydropyrrolo[3,4-c]pyrazole-5(1H)-carboxylate (0.200 g, 0.583 mmol) in DMSO (7 ml) was added NaH (60% dispersion in paraffin oil, 0.070 g, 2.92 mmol) portion wise at 15° C. The resulting reaction mixture was stirred at rt for 30 min. 2-Iodopyridine (0.143 g, 0.70 mmol) was added and the reaction mixture was heated at 130° C. for 12 h. The resulting reaction mixture was cooled to rt, poured into water (30 ml) and extracted with EtOAc (3×30 ml). The combined organic phase was dried over Na$_2$SO$_4$, filtered and concentrated under reduced pressure. The residue was purified by flash chromatography using (10% MeOH in DCM) yielding tert-butyl 1-(4-carbamoylphenyl)-3-(pyridin-2-ylamino)-4,6-dihydropyrrolo[3,4-c]pyrazole-5(1H)-carboxylate (0.073 g, 0.173 mmol). LCMS: Method 1, 1.816 min, MS: ES+ 421.70.

Steps c, d. These were carried out by a procedure similar to that described for steps c and d of Example 31 to give the title compound. LCMS: Method 6, 2.951 min, MS: ES+ 346.62; $^1$H NMR (400 MHz, DMSO-d6) δ ppm 9.22 (s, 1H), 8.16 (d, J=4.0 Hz, 1H), 8.06 (s, 1H), 7.99 (d, J=8.8 Hz, 2H), 7.64 (d, J=8.8 Hz, 2H), 7.58 (t, J=7.2 Hz, 1H), 7.45 (s, 1H), 6.79-6.82 (m, 2H), 4.60 (d, J=12.0 Hz, 4H).

Example 34 N-((5-Cyano-1,4,5,6-tetrahydropyrrolo[3,4-c]pyrazol-3-yl)methyl)-3-phenyl-1H-pyrazole-5-carboxamide

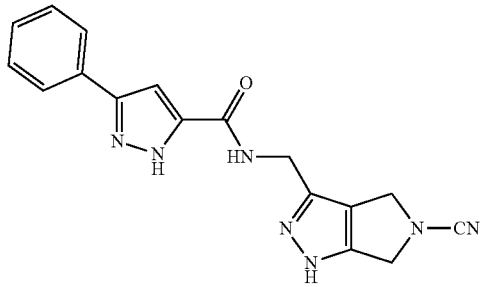 [SMILES: N#CN1Cc2[nH]nc(CNC(=O)c3cc(-c4ccccc4)n[nH]3)c2C1]

Step a. To a solution of 3-phenylpyrazole-5-carboxylic acid (CAS Number 5071-61-4, 0.2 mmol) in DCM (1 ml) was added HATU (0.2 mmol). The reaction mixture was stirred at 0° C. for 20 min. Pyrrolo[3,4-c]pyrazole-5(1H)-carboxylic acid, 3-(aminomethyl)-4,6-dihydro-, 1,1-dimethylethyl ester (CAS Number 1251002-81-9, available from Wuxi, 0.2 mmol) and DIPEA (0.6 mmol) were added to the reaction mixture at rt. The reaction mixture was stirred at rt for 16 h. The resulting mixture was concentrated under reduced pressure. The resulting residue was purified by prep-TLC (PE/EtOAc).

Step b. To a solution of the product of step a in EtOAc (1 ml) was added HCl/EtOAc (4 M, 1 ml). The reaction mixture was stirred at rt for 2 h. The resulting mixture was concentrated under reduced pressure. The residue was used for next step directly without further purification.

Step c. To a solution of the product of step b in EtOH (2 ml) was added cyanogen bromide (0.2 mmol) and NaHCO$_3$ (0.6 mmol). The reaction mixture was stirred at rt for 16 h. The resulting mixture was concentrated under reduced pressure. The crude was purified by preparative reverse phase HPLC (A: 0.078% CH$_3$COONH$_4$ in water, B: MeCN) to obtain the desired compound. LCMS Method 7, RT 2.283 min, MS: ES+ 334

Example 65 6-Chloro-N-((5-cyano-1,4,5,6-tetrahydropyrrolo[3,4-c]pyrazol-3-yl)methyl)-imidazo[1,2-a]pyridine-2-carboxamide

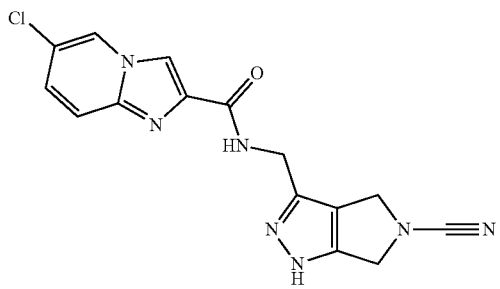 [SMILES: N#CN1Cc2[nH]nc(CNC(=O)c3cn4cc(Cl)ccc4n3)c2C1]

This was synthesised using a procedure similar to that described for Example 34, using 6-chloroimidazo[1,2-a]pyridine-2-carboxylic acid (CAS Number 182181-19-7) in step a. LCMS: Method 9, 2.011 min, MS: ES+ 342.

Example 35 N-((5-Cyano-1-phenyl-1,4,5,6-tetrahydropyrrolo[3,4-c]pyrazol-3-yl)methyl)-4-methylbenzamide

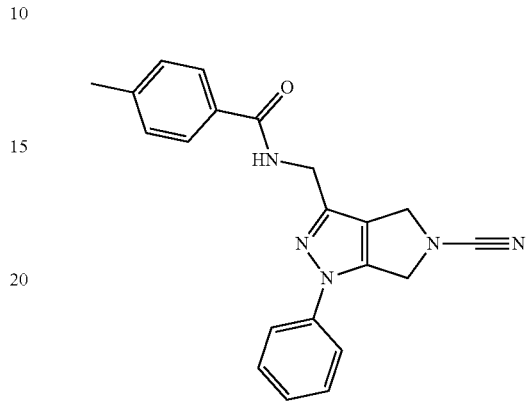

Step a. To a solution of tert-butyl 3-(aminomethyl)-4,6-dihydro-1H-pyrrolo[3,4-c]pyrazole-5-carboxylate (200 mg, 0.84 mmol) in DMF (4 ml) was added HATU (351 mg, 0.92 mmol), TEA (93 mg, 0.92 mmol, 0.13 ml), then 4-methylbenzoic acid (114 mg, 0.84 mmol) was added, the reaction mixture was stirred at rt for 16 h. The reaction mixture was diluted with water (20 ml) and extracted with EtOAc (20 ml×2). The combined organic layers were washed with water (20 ml), dried over Na$_2$SO$_4$, filtered and concentrated under reduced pressure. The residue was purified by column chromatography (SiO$_2$, PE:EtOAc=10:1 to 3:1) to provide tert-butyl 3-[[(4-methylbenzoyl)-amino]methyl]-4,6-dihydro-1H-pyrrolo[3,4-c]pyrazole-5-carboxylate (150 mg, 0.42 mmol, 50% yield) as a light yellow oil.

Step b. To a solution of tert-butyl 3-[[(4-methylbenzoyl)-amino]methyl]-4,6-dihydro-1H-pyrrolo[3,4-c]pyrazole-5-carboxylate (180 mg, 0.505 mmol), phenylboronic acid (92 mg, 0.757 mmol) in DCM (5 ml) was added Cu(OAc)$_2$ (138 mg, 0.757 mmol), pyridine (80 mg, 1.01 mmol, 0.08 ml), the reaction mixture was stirred at rt for 16 h under O$_2$. The reaction mixture was concentrated under reduced pressure to remove solvent. The residue was diluted with water (40 ml) and extracted with EtOAc (30 ml×2). The combined organic layers were washed with brine (30 ml), dried over Na$_2$SO$_4$, filtered and concentrated under reduced pressure to give a residue. The residue was purified by prep-TLC (SiO$_2$, PE:EtOAc=8:1) to get tert-butyl 3-[[(4-methylbenzoyl)amino]methyl]-1-phenyl-4,6-dihydropyrrolo[3,4-c]pyrazole-5-carboxylate (20 mg, 46 μmol, 9.16% yield) as a white solid.

Step c. To a solution of tert-butyl 3-[[(4-methylbenzoyl)amino]methyl]-1-phenyl-4,6-dihydropyrrolo[3,4-c]pyrazole-5-carboxylate (20 mg, 46 μmol) in EtOAc (1 ml) was added HCl/EtOAc (4 M, 1 ml). The reaction mixture was stirred at rt for 2 h. The resulting mixture was concentrated under reduced pressure. The residue 4-methyl-N-((1-phenyl-1,4,5,6-tetrahydropyrrolo[3,4-c]pyrazol-3-yl)methyl)benzamide was used for next step directly without further purification.

Step d. To a solution of 4-methyl-N-((1-phenyl-1,4,5,6-tetrahydropyrrolo[3,4-c]pyrazol-3-yl)methyl)benzamide in EtOH (2 ml) was added cyanogen bromide (0.2 mmol) and NaHCO₃ (0.6 mmol). The reaction mixture was stirred at rt for 16 h. The resulting mixture was concentrated under reduced pressure. The crude was purified by preparative reverse phase HPLC (A: 0.078% CH₃COONH₄ in water, B: MeCN) to provide N-((5-cyano-1-phenyl-1,4,5,6-tetrahydropyrrolo[3,4-c]pyrazol-3-yl)methyl)-4-methylbenzamide (5.2 mg, 14.5 umol). LCMS: Method 7, 2.841 min, MS: ES+ 358.1

Example 36 N-((5-Cyano-1-phenyl-1,4,5,6-tetrahydropyrrolo[3,4-c]pyrazol-3-yl)methyl)acetamide

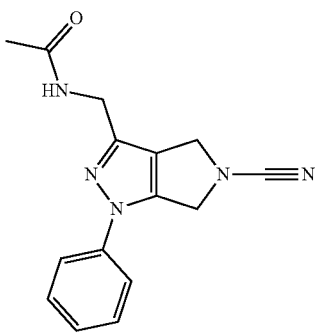 [SMILES: CC(=O)NCc1nn(-c2ccccc2)c2c1CN(C#N)C2]

Step a. To a solution of tert-butyl 3-(acetamidomethyl)-4,6-dihydro-1H-pyrrolo[3,4-c]pyrazole-5-carboxylate (500 mg, 1.78 mmol, 1.00 eq) in DCM (3 ml) was added pyridine (66 mg, 0.84 mmol), then acetic anhydride (43 mg, 0.42 mmol) dissolved in DCM (1 ml) was added slowly at 0° C., the reaction mixture was stirred at 0° C. for 30 min. The reaction mixture was poured into water (20 ml) and extracted with DCM (20 ml×2), the organic phase was washed with brine (20 ml), dried over Na₂SO₄ and concentrated to afford tert-butyl 3-(acetamidomethyl)-4,6-dihydro-1H-pyrrolo[3,4-c]pyrazole-5-carboxylate (100 mg, crude) as a white solid, the crude product was used into the next step without further purification. LCMS confirmed the structure. MS: ES+ 281.3

Step b. To a solution of tert-butyl 3-(acetamidomethyl)-4,6-dihydro-1H-pyrrolo[3,4-c]pyrazole-5-carboxylate (500 mg, 1.78 mmol) in DCM (10 ml) was added phenylboronic acid (217 mg, 1.78 mmol), pyridine (282 mg, 3.56 mmol), Cu(OAc)₂ (485 mg, 2.67 mmol), and the reaction mixture was stirred at rt for 16 h. The reaction mixture was concentrated under reduced pressure. The residue was purified by prep-HPLC (A: 0.01% TFA in water, B: MeCN) to provide tert-butyl 3-(acetamidomethyl)-1-phenyl-4,6-dihydropyrrolo[3,4-c]pyrazole-5-carboxylate (80 mg, crude) as a white solid. ¹H NMR (400 MHz, DMSO-d6) δ ppm 7.50-7.60 (m, 4H), 7.30-7.49 (m, 2H), 4.77 (s, 2H), 4.24-4.31 (m, 4H), 3.75 (d, J=4.8 Hz, 3H), 1.47 (s, 9H).

Step c. To a solution of tert-butyl 3-(acetamidomethyl)-1-phenyl-4,6-dihydropyrrolo[3,4-c]pyrazole-5-carboxylate (80 mg, crude) in EtOAc (1 ml) was added HCl/EtOAc (4 M, 1 ml). The reaction mixture was stirred at rt for 2 h. The resulting mixture was concentrated under reduced pressure. The residue N-((1-phenyl-1,4,5,6-tetrahydropyrrolo[3,4-c]pyrazol-3-yl)methyl)acetamide was used for next step directly without further purification.

Step d. To a solution of N-((1-phenyl-1,4,5,6-tetrahydropyrrolo[3,4-c]pyrazol-3-yl)methyl)acetamide in EtOH (2 ml) was added cyanogen bromide (0.2 mmol) and NaHCO₃ (0.6 mmol). The reaction mixture was stirred at rt for 16 h. The resulting mixture was concentrated under reduced pressure. The crude was purified by preparative reverse phase HPLC (A: 0.078% CH₃COONH₄ in water, B: MeCN) to provide N-((5-cyano-1-phenyl-1,4,5,6-tetrahydropyrrolo[3,4-c]pyrazol-3-yl)methyl)acetamide (3.6 mg, 12.6 μmol). LCMS: Method 9, 1.750 min, MS: ES+ 282.1; ¹H NMR (400 MHz, MeOD) δ ppm 7.48-7.57 (m, 4H), 7.32-7.36 (m, 1H), 4.93 (d, J=2.8 Hz, 2H), 4.57 (d, J=7.2 Hz, 2H), 4.38 (S, 2H), 2.02 (s, 3H).

Scheme 6

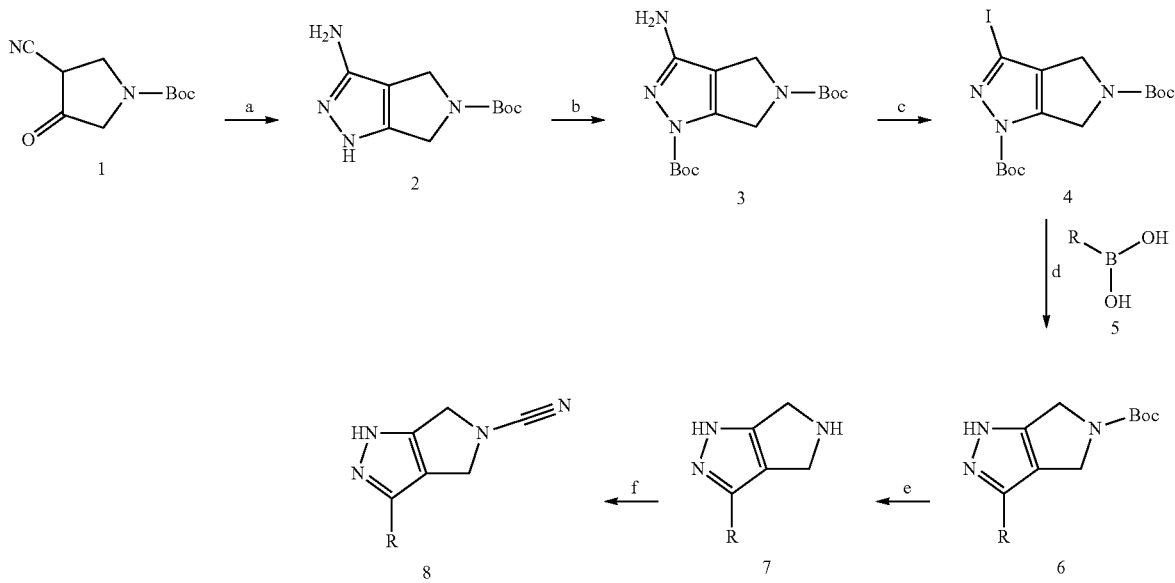

Reagents and conditions: a) hydrazine hydrate, AcOH, EtOH, 85° C., 16 h; b) (Boc)₂O, DCM, THF, rt, 16 h; c) isoamyl nitrite, iodine, rt, 1 h; d) Pd(PPh₃)₄, Cs₂CO₃, 1-4 dioxane, water, 100° C., 16 h; e) HCl/EtOAc, rt, 2 h ; f) cyanogen bromide, NaHCO₃, EtOH, rt, 16 h Step a. Hydrazine hydrate (951 mmol) was added dropwise to a solution of tert-butyl 3-cyano-4-oxopyrrolidine-1-carboxylate (190 mmol) and AcOH (1.5 mol) in EtOH (800 ml), the reaction mixture was stirred at 85° C. for 16 h. The solvents were evaporated and the residue was taken up in EtOAc (600 ml) and water (400 ml), the biphasic mixture was basified to pH=8 with solid $K_2CO_3$, the layers were separated, and the aqueous layer was extracted further with EtOAc (2×400 ml). The combined organic extracts were washed with brine (2×300 ml), dried over $Na_2SO_4$, and concentrated to obtain tert-butyl 3-amino-4,6-dihydropyrrolo[3,4-c]pyrazole-5(1H)-carboxylate (178 mmol) as a light yellow solid. MS: ES+ 225.0

Step b. To a solution of tert-butyl 3-amino-4,6-dihydropyrrolo[3,4-c]pyrazole-5(1H)-carboxylate (267.6 mmol) in DCM (1.6 L) and was added dropwise a solution of $(Boc)_2O$ (294.3 mmol) in THF (400 ml). The reaction mixture was stirred at rt for 16 h. The reaction mixture was concentrated to provide di-tert-butyl 3-amino-4,6-dihydropyrrolo[3,4-c]pyrazole-1,5-dicarboxylate (231.2 mmol). MS: ES+ 325.0

Step c. Di-tert-butyl 3-amino-4,6-dihydropyrrolo[3,4-c]pyrazole-1,5-dicarboxylate (92.5 mmol) in DCM (80 ml) was added to a solution of iodine (110.9 mmol) and isoamyl nitrite (184.9 mmol) in DCM (600 ml). The reaction mixture was stirred at rt for 1 h. The reaction mixture was poured into saturated $Na_2S_2O_3$ (150 ml) solution, the reaction mixture was separated and the aqueous layers was extracted with DCM (100 ml×2), the organic layers were washed with brine (150 ml) then dried over $Na_2SO_4$, filtered and evaporated. The residue was purified by column chromatography ($SiO_2$, PE:EtOAc=30:1 to 10:1) to provide di-tert-butyl 3-iodo-4,6-dihydropyrrolo[3,4-c]pyrazole-1,5-dicarboxylate (27.6 mmol). $^1$H NMR (400 MHz, DMSO-d6) δ ppm 1.40-1.60 (m, 2H), 4.23 (d, J=1.6 Hz, 2H), 4.38-4.62 (m, 2H).

Step d. To a solution of di-tert-butyl 3-iodopyrrolo[3,4-c]pyrazole-1,5(4H,6H)-dicarboxylate (0.2 mmol), compound 5 (0.2 mmol) and $Cs_2CO_3$ (0.6 mmol, 3 eq) in 1,4-dioxane (1 ml) and water (0.2 ml) was added tetrakis (triphenylphosphine)palladium(0) (0.2 eq) at rt under nitrogen. The reaction mixture was stirred at 100° C. for 16 h. The resulting mixture was concentrated under reduced pressure. The resulting residue was purified by prep-TLC (PE/EtOAc=1:1) yielding compound 6.

Step e. To a solution of compound 6 in EtOAc (1 ml) was added HCl/EtOAc (4 M, 1 ml). The reaction mixture was stirred at rt for 2 h. The resulting mixture was concentrated under reduced pressure. The residue compound 7 was used for next step directly without further purification.

Step f. To a solution of compound 7 in EtOH (2 ml) was added cyanogen bromide (0.2 mmol) and $NaHCO_3$ (0.6 mmol). The reaction mixture was stirred at rt for 16 h. The resulting mixture was concentrated under reduced pressure. The crude was purified by preparative reverse phase HPLC (A: 0.078% $CH_3COONH_4$ in water, B: MeCN) to provide compound 8.

Compounds in Table 7 were synthesised according to Scheme 6.

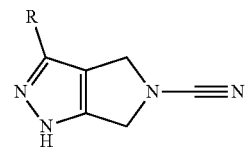

TABLE 7

| Ex | R— | Name | Boronic Acid or ester CAS Number | LCMS method | LCMS RT | MS ES+ |
|---|---|---|---|---|---|---|
| Example 37 | 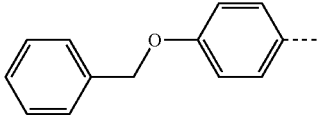 | 3-(4-(Benzyloxy)phenyl)-4,6-dihydropyrrolo[3,4-c]pyrazole-5(1H)-carbonitrile | 146631-00-7 | 7 | 2.779 min | 317 |
| Example 38 | 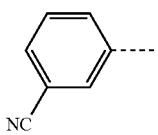 | 3-(3-Cyanophenyl)-4,6-dihydropyrrolo[3,4-c]pyrazole-5(1H)-carbonitrile | 1072945-82-4 | 9 | 2.158 min | 236.2 |
| Example 39 | 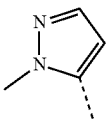 | 3-(1-Methyl-1H-pyrazol-5-yl)-4,6-dihydropyrrolo[3,4-c]pyrazole-5(1H)-carbonitrile | 847818-74-0 | 9 | 1.421 min | 215 |
| Example 40 | 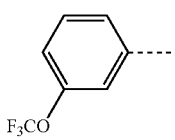 | 3-(3-(Trifluoromethoxy)phenyl)-4,6-dihydropyrrolo[3,4-c]pyrazole-5(1H)-carbonitrile | 179113-90-7 | 7 | 2.419 min | 295.1 |

TABLE 7-continued

| Ex | R— | Name | Boronic Acid or ester CAS Number | LCMS method | LCMS RT | MS ES+ |
|---|---|---|---|---|---|---|
| Example 41 | (3-phenoxyphenyl group) | 3-(4-Phenoxyphenyl)-4,6-dihydropyrrolo[3,4-c]pyrazole-5(1H)-carbonitrile | 51067-38-0 | 8 | 2.221 min | 303.1 |
| Example 42 | (4-cyanophenyl, NC–) | 3-(4-Cyanophenyl)-4,6-dihydropyrrolo[3,4-c]pyrazole-5(1H)-carbonitrile | 126747-14-6 | 9 | 2.127 min | 236.2 |
| Example 43 | (2-fluoro-4-(trifluoromethyl)phenyl, F₃C–, F) | 3-(2-Fluoro-4-(trifluoromethyl)phenyl)-4,6-dihydropyrrolo[3,4-c]pyrazole-5(1H)-carbonitrile | 503309-11-3 | 7 | 2.87 min | 297 |
| Example 44 | (2-chloro-5-(trifluoromethoxy)phenyl, Cl, F₃CO) | 3-(2-Chloro-5-(trifluoromethoxy)phenyl)-4,6-dihydropyrrolo[3,4-c]pyrazole-5(1H)-carbonitrile | 1022922-16-2 | 9 | 2.551 min | 329 |
| Example 45 | (MeHN–C(O)–pyridin-2-yl) | 5-(5-Cyano-1,4,5,6-tetrahydropyrrolo[3,4-c]pyrazol-3-yl)-N-methylpicolinamide | 1006876-27-2 | 9 | 1.806 min | 269 |
| Example 46 | (6-methoxypyridin-3-yl, MeO) | 3-(6-Methoxypyridin-3-yl)-4,6-dihydropyrrolo[3,4-c]pyrazole-5(1H)-carbonitrile | 13472-61-2 | 9 | 1.995 min | 242.1 |
| Example 47 | (3-(N,N-dimethylsulfamoyl)phenyl) | 3-(5-Cyano-1,4,5,6-tetrahydropyrrolo[3,4-c]pyrazol-3-yl)-N,N-dimethylbenzenesulfonamide | 871329-59-8 | 9 | 1.915 min | 318 |
| Example 48 | (5-fluoro-2-isopropoxyphenyl) | 3-(5-Fluoro-2-isopropoxyphenyl)-4,6-dihydropyrrolo[3,4-c]pyrazole-5(1H)-carbonitrile | 480438-63-9 | 7 | 2.79 min | 287 |
| Example 49 | (4-(N-benzylcarbamoyl)phenyl) | N-Benzyl-4-(5-cyano-1,4,5,6-tetrahydropyrrolo[3,4-c]pyrazol-3-yl)benzamide | 252663-47-1 | 7 | 2.524 min | 344 |
| Example 50 | (6-isopropoxypyridin-3-yl) | 3-(6-Isopropoxypyridin-3-yl)-4,6-dihydropyrrolo[3,4-c]pyrazole-5(1H)-carbonitrile | 870521-30-5 | 7 | 2.569 min | 270 |

TABLE 7-continued

| Ex | R— | Name | Boronic Acid or ester CAS Number | LCMS method | LCMS RT | MS ES+ |
|---|---|---|---|---|---|---|
| Example 51 | | 3-(4-(4-Methylpiperazine-1-carbonyl)phenyl)-4,6-dihydropyrrolo[3,4-c]pyrazole-5(1H)-carbonitrile | 832114-06-4 | 9 | 1.562 min | 337 |
| Example 52 | | 3-(1-Methyl-1H-indazol-5-yl)-4,6-dihydropyrrolo[3,4-c]pyrazole-5(1H)-carbonitrile | 590418-08-9 | 9 | 1.753 min | 265 |
| Example 53 | | 3-(1-Benzyl-1H-pyrazol-5-yl)-4,6-dihydropyrrolo[3,4-c]pyrazole-5(1H)-carbonitrile | 1362243-50-2 | 7 | 2.426 min | 291 |
| Example 54 | | 3-(5-Methyl-1H-indazol-4-yl)-4,6-dihydropyrrolo[3,4-c]pyrazole-5(1H)-carbonitrile | 1245816-10-7 | 9 | 1.758 min | 265 |
| Example 55 | | 3-(5-Cyano-1,4,5,6-tetrahydropyrrolo[3,4-c]pyrazol-3-yl)-N-cyclopropylbenzenesulfonamide | 913835-28-6 | 9 | 2.539 min | 330 |
| Example 56 | | N-(3-(5-Cyano-1,4,5,6-tetrahydropyrrolo[3,4-c]pyrazol-3-yl)phenyl)cyclopropanesulfonamide | 1072945-67-5 | 9 | 1.422 min | 330.1 |
| Example 66 | | 3-(4-(4-Methylpiperazin-1-yl)phenyl)-4,6-dihydropyrrolo[3,4-c]pyrazole-5(1H)-carbonitrile | 229009-40-9 | 4 | 3.235 | 309.08 |
| Example 67 | | 3-(4-Chloro-2-methoxyphenyl)-4,6-dihydropyrrolo[3,4-c]pyrazole-5(4H)-carbonitrile | 762287-57-0 | 4 | 4.097 | 274.97 |
| Example 68 | | 3-(1-(1-Methylpiperidin-4-yl)-1H-pyrazol-4-yl)-4,6-dihydropyrrolo[3,4-c]pyrazole-5(1H)-carbonitrile | 1323919-64-7 | 4 | 2.775 | 298.07 |
| Example 69 | | 3-(6-(4-Methylpiperazin-1-yl)pyridin-3-yl)-4,6-dihydropyrrolo[3,4-c]pyrazole-5(1H)-carbonitrile | 918524-63-7 | 4 | 2.974 | 310.07 |

TABLE 7-continued

| Ex | R— | Name | Boronic Acid or ester CAS Number | LCMS method | LCMS RT | MS ES+ |
|---|---|---|---|---|---|---|
| Example 70 | | 3-(2-Methoxy-4-(1H-pyrazol-1-yl)phenyl)-4,6-dihydropyrrolo[3,4-c]pyrazole-5(4H)-carbonitrile | 1562338-80-0 | 4 | 3.650 | 307.08 |
| Example 71 | | 3-(3-(4-Methylpiperazin-1-yl)phenyl)-4,6-dihydropyrrolo[3,4-c]pyrazole-5(1H)-carbonitrile | 1139717-76-2 | 4 | 3.417 | 309.08 |
| Example 72 | | 3-(4-Morpholinophenyl)-4,6-dihydropyrrolo[3,4-c]pyrazole-5(1H)-carbonitrile | 186498-02-2 | 4 | 3.236 | 296.04 |
| Example 73 | | 3-(2-Fluoro-4-(4-methylpiperazin-1-yl)phenyl)-4,6-dihydropyrrolo[3,4-c]pyrazole-5(1H)-carbonitrile | Intermediate E | 4 | 3.136 | 326.96 |
| Example 74 | | 3-(3-Methyl-4-(4-methylpiperazin-1-yl)phenyl)-4,6-dihydropyrrolo[3,4-c]pyrazole-5(1H)-carbonitrile | 1310704-51-8 | 4 | 2.568 | 323.04 |
| Example 75 | | 3-(3-(2-Oxooxazolidin-3-yl)phenyl)-4,6-dihydropyrrolo[3,4-c]pyrazole-5(1H)-carbonitrile | Intermediate F | 4 | 2.679 | ES-294.10 |
| Example 76 | | 3-(3-(2-Oxopyrrolidin-1-yl)phenyl)-4,6-dihydropyrrolo[3,4-c]pyrazole-5(1H)-carbonitrile | 1185265-61-5 | 4 | 2.676 | ES-292.10 |
| Example 77 | | 3-(5-Chloro-2-methoxyphenyl)-4,6-dihydropyrrolo[3,4-c]pyrazole-5(4H)-carbonitrile | 89694-48-4 | 4 | 4.015 | 275.04 |

Scheme 7

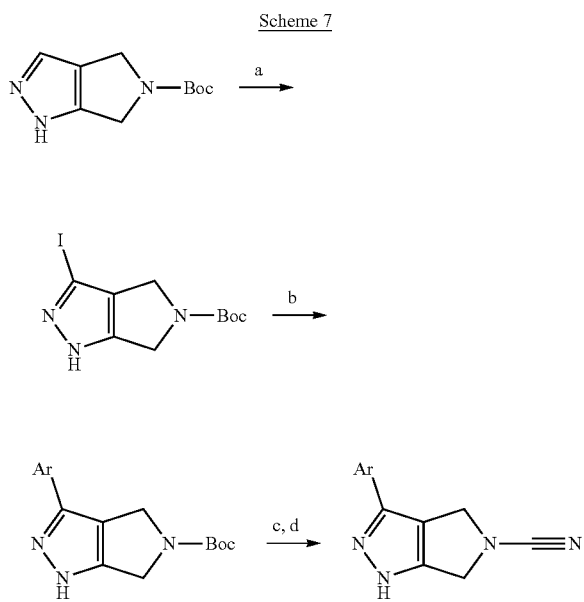

Reagents and conditions: a) Iodine, K₂CO₃, DMF; b) ArB(OH)₂, Pd(PPh₃)₄, Cs₂CO₃, 1,4-dioxane/water; c) TFA, DCM; d) BrCN, TEA, THF.

Example 57 3-(3-Fluorophenyl)-4,6-dihydropyrrolo[3,4-c]pyrazole-5(1H)-carbonitrile Synthesised According to Scheme 7

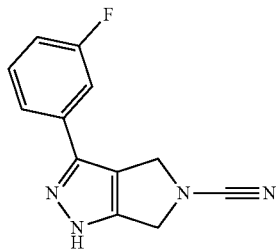 [SMILES: N#CN1Cc2[nH]nc(-c3cccc(F)c3)c2C1]

Step a. A stirred mixture of 4,6-dihydro-1H-pyrrolo[3,4-c]pyrazole-5-carboxylic acid tert-butyl ester (1.00 g, 4.78 mmol), iodine (2.43 g, 9.57 mmol) and K₂CO₃ (1.32 g, 9.57 mmol) in DMF (15 ml) was heated to 75° C. under a nitrogen atmosphere for 18 h. The mixture was cooled to rt, diluted with EtOAc (50 ml) and washed with 10% Na₂S₂O₃ (50 ml). The separated aqueous layer was extracted with EtOAc (50 ml), the combined organic extracts were dried over Na₂SO₄ and evaporated. The solid residue was triturated with DCM (2×20 ml) to give tert-butyl 3-iodo-4,6-dihydropyrrolo[3,4-c]pyrazole-5(1H)-carboxylate (628 mg, 1.87 mmol, 39%) as a white solid. LCMS: Method 1, 3.34 min, MS: ES+ 336; ¹H NMR (400 MHz, MeOD) δ ppm 4.48 (d, J=8.3 Hz, 2H), 4.31 (d, J=8.3 Hz, 2H), 1.51 (s, 9H).

Step b. A mixture of tert-butyl 3-iodo-4,6-dihydropyrrolo[3,4-c]pyrazole-5(1H)-carboxylate (200 mg, 0.60 mmol), 3-fluorobenzeneboronic acid (125 mg, 0.90 mmol) and Cs₂CO₃ (487 mg, 1.49 mmol) in 1,4-dioxane/water (4:1, 10 ml) was degassed by nitrogen bubbling for 10 min. Tetrakis(triphenylphosphine) palladium(0) (104 mg, 0.09 mmol) was added and degassing continued for 10 min. The stirred mixture was heated at reflux for 18 h, then cooled to rt. Water (10 ml) and brine (5 ml) were added and the mixture was extracted successively with EtOAc (2×50 ml) and DCM (2×15 ml). The combined organic extracts were dried over Na₂SO₄ and evaporated. The solid residue was partially dissolved in DCM/MeOH and purified by flash column chromatography with a gradient of (10-50% EtOAc/hexane) to give tert-butyl 3-(3-fluorophenyl)-4,6-dihydropyrrolo[3,4-c]pyrazole-5(1H)-carboxylate (105 mg, 0.35 mmol, 58%) as a white solid. LCMS: Method 1, 3.36 min, MS: ES+ 304; ¹H NMR (400 MHz, CDCl₃+MeOD) δ ppm 7.40-7.46 (m, 1H), 7.26-7.35 (m, 2H), 7.02-7.08 (m, 1H), 4.62 (s, 2H), 4.48 (s, 2H), 1.53 (s, 9H).

Step c. TFA (0.5 ml, 6.53 mmol) was added to a stirred suspension of tert-butyl 3-(3-fluorophenyl)-4,6-dihydropyrrolo[3,4-c]pyrazole-5(1H)-carboxylate (105 mg, 0.35 mmol) in DCM (3 ml). The resulting yellow solution was stirred at rt for 2 h. The mixture was evaporated and azeotroped with toluene:MeCN (1:1 mixture, 3×20 ml) to give 3-fluorophenyl)-1,4,5,6-tetrahydropyrrolo[3,4-c]pyrazole 2,2,2-trifluoroacetate (128 mg, 0.40 mmol, quantitative) as a pale yellow oily solid. LCMS: Method 1, 0.64 min, MS: ES+ 204; ¹H NMR (400 MHz, CDCl₃+MeOD) δ ppm 7.40-7.48 (m, 1H), 7.20-7.30 (m, 2H), 7.02-7.08 (m, 1H), 4.40 (s, 2H), 3.67 (s, 1H), 3.31 (s, 1H).

Step d. TEA (0.15 ml, 1.05 mmol) was added to a stirred suspension of 3-(3-fluorophenyl)-1,4,5,6-tetrahydropyrrolo[3,4-c]pyrazole 2,2,2-trifluoroacetate (128 mg, 0.35 mmol) in THF (5 ml) under a nitrogen atmosphere. Further TEA (0.15 ml, 1.05 mmol) was added to dissolve all solids. The resulting yellow solution was cooled to 0° C. and cyanogen bromide (5 M in MeCN, 0.08 ml, 0.42 mmol) was added slowly to give an orange suspension. Stirring was continued at 0° C. for 2 h. Water (10 ml) and brine (5 ml) were added and the mixture was extracted with EtOAc (2×30 ml). The combined organic extracts were dried over Na₂SO₄ and evaporated. The solid residue was partially dissolved in DCM/EtOAc and purified by flash column chromatography with a gradient of 10-50% EtOAc/hexane to give a white solid (22 mg) which contained small amounts of trimethylamine salts. This was triturated with MeCN (×3) to give 3-(3-fluorophenyl)-4,6-dihydropyrrolo[3,4-c]pyrazole-5(1H)-carbonitrile (20 mg, 0.087 mmol, 25% over 2 steps) as a white solid. LCMS: Method 14, 3.70 min, MS: ES+ 229; ¹H NMR (400 MHz, DMSO-d6) δ ppm 8.04 (1H, s), 7.61-7.64 (m, 1H), 7.50-7.58 (m, 2H), 7.22-7.30 (m, 1H), 4.84 (s, 4H).

Compounds in Table 8 were synthesised using a procedure similar to that described for Example 57.

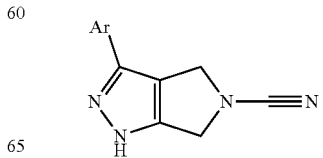

TABLE 8

| Ex | Ar— | Name | Boronic acid CAS Number | LCMS method | LCMS RT | MS ES+ |
|---|---|---|---|---|---|---|
| Example 58 | 2-fluorophenyl | 3-(2-Fluorophenyl)-4,6-dihydropyrrolo[3,4-c]pyrazole-5(1H)-carbonitrile | 1993-03-9 | 14 | 3.69 min | 229 |
| Example 59 | 4-fluorophenyl | 3-(4-Fluorophenyl)-4,6-dihydropyrrolo[3,4-c]pyrazole-5(1H)-carbonitrile | 1765-93-1 | 13 | 3.29 min | 229 |

Example 60 3-(2-fluoro-5-methylphenyl)-1-methyl-4,6-dihydropyrrolo[3,4-c]pyrazole-5(1H)-carbonitrile

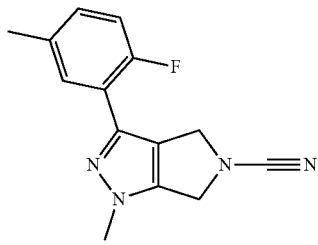 [SMILES: Cc1ccc(F)c(-c2nn(C)c3c2CN(C#N)C3)c1]

Steps a, b. Following a similar procedure to Example 57, steps a and b using 2-fluoro-5-methylbenzeneboronic acid (CAS Number 166328-16-1) in step b to give tert-butyl 3-(2-fluoro-5-methylphenyl)-4,6-dihydropyrrolo[3,4-c]pyrazole-5(1H)-carboxylate.

Step c. NaH (60% w/w dispersion in oil, 55 mg, 1.36 mmol) was added to a stirred solution of tert-butyl 3-(2-fluoro-5-methylphenyl)-4,6-dihydropyrrolo[3,4-c]pyrazole-5(1H)-carboxylate (360 mg, 1.14 mmol) in DMF (10 ml) under a nitrogen atmosphere. After 30 minutes, iodomethane (194 mg, 1.36 mmol) was added and the solution stirred at rt for 6 h. Water (10 ml) was added, followed by brine (20 ml), and the mixture was extracted with EtOAc (2×50 ml). The combined organic extracts were dried over $Na_2SO_4$ and evaporated to leave a yellow oily solid (330 mg). This was purified by flash column chromatography (10-50% EtOAc/hexane) to give the less polar minor isomer: tert-butyl 3-(2-fluoro-5-methylphenyl)-2-methyl-4,6-dihydropyrrolo[3,4-c]pyrazole-5(1H)-carboxylate as a yellow oil (38 mg). LCMS: Method 3, 5.34 min, MS: ES+ 332; $^1$H NMR (400 MHz, $CDCl_3$) δ ppm 7.22-7.18 (m, 1H), 7.04-7.10 (m, 2H), 4.54-4.39 (m, 4H), 3.81 (s, 3H), 2.37 (m, 3H), 1.50 (m, 9H) and the more polar major isomer, tert-butyl 3-(2-fluoro-5-methylphenyl)-1-methyl-4,6-dihydropyrrolo[3,4-c]pyrazole-5(1H)-carboxylate as an off-white solid (210 mg). Overall yield (248 mg, 66%). LCMS: Method 3, 5.26 min, MS: ES+ 332; $^1$H NMR (400 MHz, $CDCl_3$) δ ppm 7.75-7.70 (m, 1H), 7.10-7.04 (m, 1H), 6.98-6.95 (m, 1H), 4.60-4.50 (m, 4H), 3.88 (s, 3H), 2.35 (s, 3H), 1.52 (s, 9H)

Steps d, e. The title compound was synthesised from tert-butyl 3-(2-fluoro-5-methylphenyl)-1-methyl-4,6-dihydropyrrolo[3,4-c]pyrazole-5(1H)-carboxylate using a procedure similar to that described for Example 57, steps c and d. LCMS: Method 14, 5.07 min, MS: ES+ 257.

Example 61 3-(2-fluoro-5-methylphenyl)-2-methyl-2,6-dihydropyrrolo[3,4-c]pyrazole-5(4H)-carbonitrile

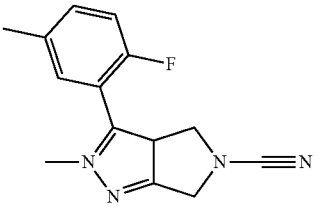

Synthesised using a procedure similar to that described for Example 60, using tert-butyl 3-(2-fluoro-5-methylphenyl)-2-methyl-2,6-dihydropyrrolo[3,4-c]pyrazole-5(1H)-carboxylate (prepared as described in steps a-c of Example 60). LCMS: Method 14, 4.97 min, MS: ES+ 257.

Example 62 3-(5-Isopropyl-2-methoxyphenyl)-1-methyl-4,6-dihydropyrrolo[3,4-c]pyrazole-5(1H)-carbonitrile

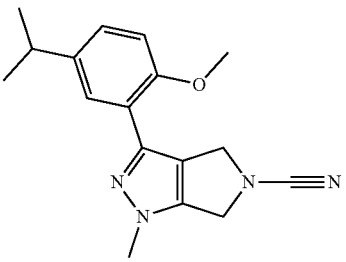 [SMILES: COc1ccc(C(C)C)cc1-c1nn(C)c2c1CN(C#N)C2]

Synthesised using a procedure similar to that described for Example 60/61, using 5-isopropyl-2-methoxyphenylboronic acid (CAS Number 216393-63-4). LCMS: Method 4, 4.925 min, MS: ES+ 296.91

Example 63 3-(5-Isopropyl-2-methoxyphenyl)-2-methyl-2,6-dihydropyrrolo[3,4-c]pyrazole-5(4H)-carbonitrile

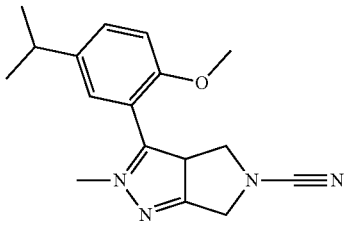

Synthesised using a procedure similar to that described for Example 60/61, using 5-isopropyl-2-methoxyphenylboronic acid (CAS Number 216393-63-4). LCMS: Method 4, 4.836 min, MS: ES+ 296.91.

Example 78 N-(3-(5-Cyano-5,6-dihydropyrrolo[3,4-c]pyrazol-1(4H)-yl)phenyl) cyclopropanesulfonamide

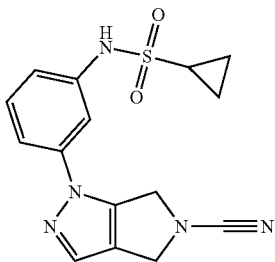 [SMILES: N#CN1Cc2cnn(-c3cccc(NS(=O)(=O)C4CC4)c3)c2C1]

Step a. A solution of N-Boc-3-pyrrolidinone (CAS Number 101385-93-7; 5.0 g, 27.0 mmol) in DMF-DMA (32.17 g, 270 mmol) was heated at 100° C. for 1.5 h. The resulting mixture was cooled to rt and concentrated under reduced pressure. The obtained residue was triturated with n-pentane (100 ml). The resulting solid was dried under high vacuum yielding tert-butyl 3-((dimethylamino)methylene)-4-oxopyrrolidine-1-carboxylate (4.700 g, 19.58 mmol). LCMS: Method 1, 1.556 min, MS: ES+ 241.43.

Step b. A solution of tert-butyl 3-((dimethylamino) methylene)-4-oxopyrrolidine-1-carboxylate (1.250 g, 5.208 mmol) in EtOH (12 ml) were added 3-nitrophenylhydrazine hydrochloride (CAS Number 636-95-3; 0.987 g, 5.21 mmol) and AcOH (0.5 ml) at rt. The reaction mixture was heated at 85° C. for 2 h. The resulting reaction mixture was combined with one batch prepared on the same scale by an identical method. The resulting mixture was cooled to rt and concentrated under reduced pressure. The resulting residue was purified by flash chromatography (10% EtOAc in n-hexane) yielding tert-butyl 1-(3-nitrophenyl)-4,6-dihydropyrrolo[3,4-c]pyrazole-5(1H)-carboxylate (0.866 g, 2.624 mmol). LCMS: Method 1, 2.336 min, MS: ES+ 331.40.

Step c. To a solution of tert-butyl 1-(3-nitrophenyl)-4,6-dihydropyrrolo[3,4-c]pyrazole-5(1H)-carboxylate (0.866 g, 2.624 mmol) in MeOH (10 ml) was added 10% dry Pd/C (0.130 g) at rt. The resulting reaction mixture was purged with $H_2$ for 3 h. The reaction mixture was filtered throw celite pad and washed with EtOH (4×10 ml). The combined filtrate was concentrated under reduced pressure to yield tert-butyl 1-(3-aminophenyl)-4,6-dihydropyrrolo[3,4-c]pyrazole-5(1H)-carboxylate (0.530 g, 1.766 mmol). LCMS: Method 1, 1.927 min, MS: ES+ 301.48.

Step d. A solution of tert-butyl 1-(3-aminophenyl)-4,6-dihydropyrrolo[3,4-c]pyrazole-5(1H)-carboxylate (0.300 g, 1.000 mmol) in DCM (3 ml) was added pyridine (0.396 g, 5.000 mmol) at 0° C. The reaction mixture was stirred at 0° C. for 15 min. Cyclopropanesulfonyl chloride (CAS Number 139631-62-2, 0.155 g, 1.100 mmol) was added to the reaction mixture at 0° C. The resulting mixture was stirred at rt for 3 h. The resulting reaction mixture was poured into water (10 ml) and extracted with EtOAc (3×10 ml). The combined organic phase was dried over $Na_2SO_4$, filtered and concentrated under reduced pressure. The residue was purified by flash chromatography (20% EtOAc in hexane) yielding tert-butyl 1-(3-(cyclopropanesulfonamido)phenyl)-4,6-dihydropyrrolo[3,4-c]pyrazole-5(1H)-carboxylate (0.285 g, 0.705 mmol). LCMS: Method 1, 2.055 min, MS: ES+ 405.38; $^1$H NMR (400 MHz, DMSO-$d_6$) δ ppm 10.01 (s, 1H), 7.60-7.56 (m, 2H), 7.47-7.42 (m, 1H), 7.35-7.28 (m, 1H), 7.16 (t, J=8.4 Hz, 1H), 4.77 (s, 2H), 4.37 (d, J=11.2 Hz, 2H), 2.69 (t, J=5.2 Hz, 1H), 1.47 (s, 9H), 0.96 (d, J=8.0 Hz, 4H).

Step e. To a solution of tert-butyl 1-(3-(cyclopropanesulfonamido)phenyl)-4,6-dihydropyrrolo[3,4-c]pyrazole-5 (1H)-carboxylate (0.285 g, 0.705 mmol) in DCM (3 ml) was added TFA (0.402 g, 3.527 mmol) at 0° C. The reaction mixture was stirred at rt for 15 min. The resulting reaction mixture was concentrated under reduced pressure. The obtained residue was co-distilled with DCM (4×5 ml). The obtained residue was dried under high vacuum yielding N-(3-(5,6-dihydropyrrolo[3,4-c]pyrazol-1(4H)-yl)phenyl)-cyclopropanesulfonamide TFA salt (0.170 g, 0.406 mmol). LCMS: Method 1, 1.341 min, MS: ES+ 305.48. This material was used directly for the next step without further purification.

Step f. To a solution of N-(3-(5,6-dihydropyrrolo[3,4-c] pyrazol-1(4H)-yl)phenyl)-cyclopropanesulfonamide TFA salt (0.150 g, 0.358 mmol) in THF (3 ml) was added $K_2CO_3$ (0.099 g, 0.717 mmol) at 0° C. The reaction mixture was stirred at 0° C. for 5 min. Cyanogen bromide (0.038 g, 0.358 mmol) was added to the reaction mixture at 0° C. The reaction mixture was stirred at rt for 15 min. The resulting reaction mixture was poured into water (10 ml) and extracted with EtOAc (3×10 ml). The combined organic phase was dried over $Na_2SO_4$, filtered and concentrated under reduced pressure. The resulting residue was purified by flash chromatography (2% MeOH in DCM) yielding the title compound (0.115 g, 0.349 mmol). LCMS: Method 4, 3.593 min, MS: ES+ 330.02; $^1$H NMR (400 MHz, DMSO-$d_6$) δ ppm 10.00 (s, 1H), 7.61 (s, 1H), 7.56 (t, J=2.0 Hz, 1H), 7.44 (t, J=8.0 Hz, 1H), 7.26 (dd, J=1.2 Hz, 1.6 Hz, 1H), 7.18 (dd, J=1.2 Hz, 1.2 Hz, 1H), 5.00 (t, J=2.0 Hz, 2H), 4.59 (d, J=2.4 Hz, 2H), 2.72-2.67 (m, 1H), 0.96 (t, J=2.8 Hz, 4H).

Example 79 N-Benzyl-4-(5-cyano-1,4,5,6-tetrahydropyrrolo[3,4-c]pyrazol-3-yl)-3-fluorobenzamide

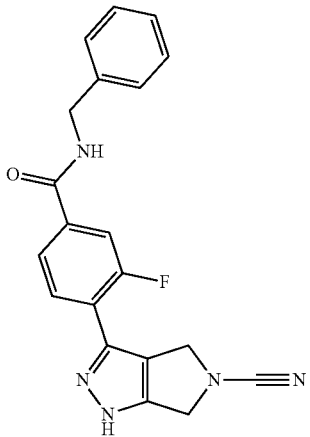 [SMILES: N#CN1Cc2[nH]nc(-c3ccc(C(=O)NCc4ccccc4)cc3F)c2C1]

Step a. A solution of tert-Butyl 3-cyano-4-oxopyrrolidine-1-carboxylate (CAS Number 175463-32-8; 30.00 g, 142.7 mmol) in EtOH (600 ml) was added AcOH (57 ml, 1000 mmol) and hydrazine hydrate 99% (35 ml, 714 mmol) at rt. The reaction mixture was heated at 85° C. for 14 h. The reaction mixture was cooled to rt and concentrated under reduced pressure. The residue was diluted with EtOAc (400 ml) and water (400 ml), pH was adjusted up to ~8 with by portion wise addition of solid $Na_2CO_3$. The resulting mixture extracted with EtOAc (2×400 ml). The combined organic phase was collected, dried over $Na_2SO_4$, filtered and concentrated under reduced pressure. The residue was purified by column chromatography (5% MeOH in DCM) yielding tert-butyl 3-amino-4,6-dihydropyrrolo[3,4-c]pyrazole-5(1H)-carboxylate (18.0 g, 80.357 mmol). LCMS: Method 1, 1.707 min, MS: ES+ 225.33.

Step b. To a solution of tert-butyl 3-amino-4,6-dihydropyrrolo[3,4-c]pyrazole-5(1H)-carboxylate (5.000 g, 22.32 mmol) in DCM:THF (4:1, 50 ml) was added $(Boc)_2O$ (5.352 g, 24.55 mmol) at rt. The resulting reaction mixture was stirred at rt for 18 h. The resulting reaction mixture was combined with one other batch prepared on the same scale by an identical method. The resulting mixture was concentrated under vacuum. The residue was purified by column chromatography (40 to 60% EtOAc in n-hexane) yielding di-tert-butyl 3-amino-4,6-dihydropyrrolo[3,4-c]pyrazole-1,5-dicarboxylate (17.8 g, quantitative). LCMS: Method 1, 2.269 min, MS: ES+ 325.43; $^1$H NMR (400 MHz, DMSO-d6) δ ppm 6.51 (d, J=9.6 Hz, 2H), 4.19 (d, J=5.2 Hz, 2H), 4.13 (d, J=19.2 Hz, 2H), 1.54 (s, 9H), 1.43 (s, 9H).

Step c. To a mixture of iodine (1.880 g, 7.407 mmol) and isoamyl nitrite (1.68 ml, 12.3 mmol) in DCM (10 ml) was added to a solution of di-tert-butyl 3-amino-4,6-dihydropyrrolo[3,4-c]pyrazole-1,5-dicarboxylate (2.000 g, 6.165 mmol) in DCM (40 ml) over 30 min at rt. The reaction mixture was stirred at rt for 14 h. The resulting reaction mixture was poured into saturated $Na_2S_2O_3$ solution (20 ml) and extracted with DCM (2×20 ml). The combined organic phase was dried over $Na_2SO_4$, filtered and concentrated under reduced pressure. The residue was purified by column chromatography (7-10% EtOAc in hexane) yielding di-tert-butyl 3-iodo-4,6-dihydropyrrolo[3,4-c]pyrazole-1,5-dicarboxylate (0.730 g, 1.678 mmol). LCMS: Method 1, 2.558 min, MS: ES+ 436.38; $^1$H NMR (400 MHz, DMSO-d6) δ ppm 4.41 (d, J=8.0 Hz, 2H), 4.23 (d, J=15.6 Hz, 2H), 4.39 (d, J=11.2 Hz, 2H), 1.58 (s, 9H), 1.45 (s, 9H).

Step d. A mixture of di-tert-butyl 3-iodo-4,6-dihydropyrrolo[3,4-c]pyrazole-1,5-dicarboxylate (0.400 g, 0.918 mmol), 2-fluoro-4-(methoxycarbonyl)phenylboronic acid (CAS Number 603122-84-5; 0.218 g, 1.102 mmol) and $NaHCO_3$ (0.154 g, 1.837 mmol) in DMF:water (9:1) (8 ml) was degassed with nitrogen for 10 min at rt before addition of $PdCl_2$(dppf) DCM complex (0.91 g, 0.795 mmol). The reaction mixture was heated at 100° C. for 4 h. The resulting reaction mixture was cooled to rt and poured into ice cold water (20 ml). The resulting precipitates were collected by filtration and dried under high vacuum. The resulting solid was purified by flash chromatography (2-3% MeOH in DCM) yielding tert-butyl 3-(2-fluoro-4-(methoxycarbonyl)phenyl)-4,6-dihydropyrrolo[3,4-c]pyrazole-5(1H)-carboxylate (0.220 g, 0.609 mmol). LCMS: Method 1, 2.219 min, MS: ES+ 362.43.

Step e. To a solution of tert-butyl 3-(2-fluoro-4-(methoxycarbonyl)phenyl)-4,6-dihydropyrrolo[3,4-c]pyrazole-5(1H)-carboxylate (0.180 g, 0.498 mmol) in MeOH (5 ml) was added $LiOH.H_2O$ (0.837, 1.994 mmol) at rt. The reaction mixture was heated at 85° C. for 12 h. The reaction mixture cooled to rt and concentrated under vacuum. The obtained crude was diluted with water (10 ml) and extracted with EtOAc (2×10 ml). Aqueous layer was separated and acidified to ~4 pH using 10% citric acid solution and extracted with EtOAc (2×10 ml). The combined organic phase was concentrated under reduced pressure. The residue was purified by trituration using diethyl ether (2×5 ml) to yield 4-(5-(tert-butoxycarbonyl)-1,4,5,6-tetrahydropyrrolo[3,4-c]pyrazol-3-yl)-3-fluorobenzoic acid (0.145 g, 0.417 mmol). LCMS: Method 1, 1.874 min, MS: ES+ 348.38

Step f. To a solution of 4-(5-(tert-butoxycarbonyl)-1,4,5,6-tetrahydropyrrolo[3,4-c]pyrazol-3-yl)-3-fluorobenzoic acid (0.145 g, 0.417 mmol) in DMF (5 ml) were added HATU (0.476 g, 1.253 mmol) and DIPEA (0.215 ml, 1.253 mmol) at 0° C. The reaction mixture was stirred at 0° C. for 30 min before addition of benzylamine (0.053 g, 0.501 mmol). The resulting reaction mixture was stirred at rt for 12 h. The reaction mixture was diluted with water (10 ml) and extracted with EtOAc (3×10 ml). The combined organic phase was dried over $Na_2SO_4$, filtered and concentrated under reduced pressure. The residue was purified by flash chromatography (3.5 to 4% MeOH in DCM) yielding tert-butyl 3-(4-(benzylcarbamoyl)-2-fluorophenyl)-4,6-dihydropyrrolo[3,4-c]pyrazole-5(1H)-carboxylate (0.105 g, 0.240 mmol). LCMS: Method 1, 2.173 min, MS: ES+ 436.12;

Steps g and h were carried out in a similar manner to Example 78. LCMS: Method 4, 3.867 min, MS: ES+ 362.08; $^1$H NMR (400 MHz, DMSO-d6) δ ppm 13.46 (s, 1H), 9.20 (t, J=5.6 Hz, 1H), 7.85-7.79 (m, 3H), 7.34-7.25 (m, 5H), 4.72 (s, 2H), 4.61 (s, 2H), 4.50 (d, J=5.6 Hz, 2H).

Biological Activity of Compounds of the Invention

Abbreviations

TAMRA carboxytetramethylrhodamine
PCR polymerase chain reaction
PBS phosphate buffered saline
EDTA ethylenediaminetetraacetic acid
Tris 2-amino-2-(hydroxymethyl)-1,3-propanediol
NP40 Nonidet P-40, octylphenoxypolyethoxyethanol
BSA bovine serum albumin
In Vitro USP7 Inhibition Assay
Expression and Purification of USP7

The USP7 construct was PCR amplified and cloned into a pFLAG-CMV-6a vector (Sigma-Aldrich) with an N-terminal FLAG tag. HEK293T cells were transfected with FLAG-USP7 using TransIT-LT1 transfection reagent (Mirus) according to the manufacturer's instructions. Cells were harvested 40 hours after transfection. Cells were washed once with PBS and scraped in lysis buffer (50 mM Tris, pH 7.5, 150 mM NaCl, 3 mM EDTA, 0.5% NP40, 10% glycerol, 5 mM beta-mercaptoethanol, protease inhibitors (complete mini, Roche) and phosphatase inhibitors (PhosSTOP mini, Roche). Lysates were incubated for 30 min on ice and centrifuged at 4000 rpm for 10 min at 4° C. Soluble supernatant was added to FLAG affinity resin (EZview Rad ANTI-FLAG M2 affinity gel, Sigma-Aldrich) equilibrated in low salt buffer (20 mM Tris, pH 7.5, 150 mM NaCl, 0.5 mM EDTA, 5 mM beta-mercaptoethanol) and incubated at 4° C. for 3 hours rotating. The resin was spun at 2000 rpm for 2 min and the supernatant was removed. The resin was washed two times with low salt buffer plus protease inhibitors (complete mini, Roche) and phosphatase inhibitors (PhosSTOP mini, Roche) and one time with high salt buffer (20 mM Tris, pH 7.5, 500 mM NaCl, 0.5 mM EDTA, 5 mM beta-mercaptoethanol, protease inhibitors (complete mini, Roche) and phosphatase inhibitors (PhosSTOP mini, Roche). To elute the bound USP7, elution buffer (10 mM Tris, pH 7.5, 150 mM NaCl, 0.5 mM EDTA, 10% glycerol, 0.5% NP40, 5 mM beta-mercaptoethanol, 0.15 mg/ml 3×FLAG peptide (Sigma-Aldrich)) was added to the resin and incubated at 4° C. for 2.5 hours rotating. The resin was centrifuged at 4000 rpm for 30 seconds, and the supernatant containing purified FLAG-USP7 was removed and stored at −80° C.

USP7 Biochemical Kinetic Assay

Reactions were performed in duplicate in black 384 well plates (small volume, Greiner 784076) in a final reaction volume of 21 µl. USP7 was diluted in reaction buffer (20 mM Tris, pH 7.5, 100 mM NaCl, 0.05% Tween 20, 0.5 mg/ml BSA, 5 mM—beta mercaptoethanol) to the equivalent of 0, 0.0005, 0.001, 0.0025, and 0.005 µl/well. Buffer was optimised for optimal temperature, pH, reducing agent, salts, time of incubation, and detergent. Reactions were initiated by the addition of 50 nM of TAMRA labelled peptide linked to ubiquitin via an iso-peptide bond as fluorescence polarisation substrate. Reactions were incubated at room temperature and read every 2 min for 120 min. Readings were performed on a Pherastar Plus (BMG Labtech). λ Excitation 540 nm; λ Emission 590 nm.

USP7 Biochemical IC$_{50}$ Assay

Dilution plates were prepared at 21 times the final concentration (2100 µM for a final concentration of 100 µM) in 50% DMSO in a 96-well polypropylene V-bottom plate (Greiner #651201). A typical 8-point dilution series would be 100, 30, 10, 3, 1, 0.3, 0.1, 0.03 µM final. Reactions were performed in duplicate in black 384 well plates (small volume, Greiner 784076) in a final reaction volume of 21 µl. Either 1 µl of 50% DMSO or diluted compound was added to the plate. USP7 was diluted in reaction buffer (20 mM Tris, pH 7.5, 100 mM NaCl, 0.05% Tween 20, 0.5 mg/ml BSA, 5 mM—beta mercaptoethanol) to the equivalent of 0.0025 µl/well and 10 µl of diluted USP7 was added to the compound. Enzyme and compound were incubated for 30 min at room temp. Reactions were initiated by the addition of 50 nM of TAMRA labelled peptide linked to ubiquitin via an iso-peptide bond as fluorescence polarisation substrate. Reactions were read immediately after addition of substrate and following a 2 hr incubation at room temperature. Readings were performed on a Pherastar Plus (BMG Labtech). λ Excitation 540 nm; λ Emission 590 nm.

Activity of Exemplary Compounds in USP7 Biochemical IC50 Assay

Ranges:
A<10 µM;
10 µM<B<30 µM;
30 µM<C<100 µM

| Example | IC50 range |
|---|---|
| 1 | B |
| 2 | B |
| 3 | A |
| 4 | B |
| 5 | B |
| 6 | A |
| 7 | B |
| 8 | A |
| 9 | B |
| 10 | B |
| 11 | B |
| 12 | B |
| 13 | A |
| 14 | B |
| 15 | B |
| 16 | A |
| 17 | A |
| 18 | C |
| 19 | A |
| 20 | B |
| 21 | A |
| 22 | A |
| 23 | A |
| 24 | B |
| 25 | B |
| 26 | A |
| 27 | A |
| 28 | B |
| 29 | A |
| 30 | A |
| 31 | A |
| 32 | A |
| 33 | B |
| 34 | A |
| 35 | A |
| 36 | B |
| 37 | A |
| 38 | A |
| 39 | B |
| 40 | B |
| 41 | A |
| 42 | A |
| 43 | A |
| 44 | A |
| 45 | A |
| 46 | A |
| 47 | A |
| 48 | A |
| 49 | A |
| 50 | A |
| 51 | A |
| 52 | A |
| 53 | B |
| 54 | A |
| 55 | A |
| 56 | A |
| 57 | A |
| 58 | A |
| 59 | A |
| 60 | A |
| 61 | B |
| 62 | A |
| 63 | B |
| 64 | A |
| 65 | A |
| 66 | A |
| 67 | A |
| 68 | A |

-continued

| Example | IC50 range |
|---|---|
| 69 | A |
| 70 | A |
| 71 | A |
| 72 | A |
| 73 | A |
| 74 | A |
| 75 | A |
| 76 | A |
| 77 | A |
| 78 | B |
| 79 | A |

The invention claimed is:

1. A compound of formula II:

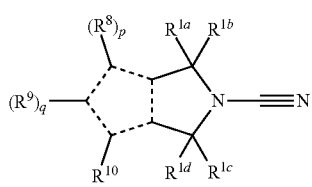

(II)

or a pharmaceutically acceptable salt thereof, wherein ⁓⁓⁓ represents an aromatic bond;

p is 0 or 1;
q is 0 or 1;
wherein p and q are not both 0 and one of p and q is 1;
$R^8$ is hydrogen, -$Q^1$-B or -$Q^2$-$(D)_m$;
$R^9$ is hydrogen or $C_1$-$C_6$ alkyl, which is optionally substituted by halogen, hydroxyl or cyano;
$R^{10}$ is hydrogen, -$Q^1$-B or -$Q^2$-$(D)_m$;
wherein one of $R^8$ or $R^{10}$ is -$Q^1$-B;
$R^{1a}$, $R^{1b}$, $R^{1c}$, $R^{1d}$ are each independently hydrogen or $C_1$-$C_6$ alkyl, or $R^{1a}$ and $R^{1b}$ together form a $C_3$-$C_6$ cycloalkyl ring, or $R^{1c}$ and $R^{1d}$ together form a $C_3$-$C_6$ cycloalkyl ring;
m is 0 or 1,
$Q^1$ is a covalent bond, an oxygen atom, a sulphur atom, —$OR^4$—, —SO—, —$SO_2$—, —C(O)—, —C(O)O—, —$C_0$-$C_3$-alkylene-C(O)$NR^2$—$C_0$-$C_3$ alkylene, —$C_0$-$C_3$-alkylene-$NR^2$—$C_0$-$C_3$-alkylene-, —$C_0$-$C_3$-alkylene-$NR^2$C(O)—$C_0$-$C_3$-alkylene, —$NR^2$C(O)$NR^3$—, —$SO_2NR^2$—, $NR^2SO_2$—, —$NR^2SO_2$—, —$NR^2SO_2NR^3$—, —$NR^2$C(O)—, —$NR^2$C(O)$OR^4$—, —$C_1$-$C_6$ alkylene, or —$C_2$-$C_6$ alkenylene;
$R^2$ and $R^3$ are each independently hydrogen or $C_1$-$C_6$ alkyl;
$R^4$ is $C_1$-$C_6$ alkylene;
B is a 5 to 10-membered, monocyclic or bicyclic, aryl or heteroaryl ring, wherein said heteroaryl ring comprises 1 to 5 heteroatoms, each independently selected from N, O and S;
wherein B is unsubstituted or substituted with one to four substituents, each independently selected from halogen, cyano, oxo, hydroxyl, —$SR^{11}$, —$C_1$-$C_6$ alkyl, —$C_1$-$C_6$ alkoxy, —$C_2$-$C_6$ alkenyl, —$C_2$-$C_6$ alkynyl, -$Q^{3a}$-$R^{13}$, -$Q^{3a}$-O-$Q^{3b}$-$R^{13}$, -$Q^{3a}$-S-$Q^{3b}$-$R^{13}$, -$Q^{3a}$-SO-$Q^{3b}$-$R^{13}$, -$Q^{3a}$-$NR^{11}$CONR$^{12}$R$^{12a}$, -$Q^{3a}$-NR$^{11}$CONR$^{12}$-$Q^{3a}$-$R^{13}$, -$Q^{3a}$-$NR^{11}R^{12}$, -$Q^{3a}$-$NR^{11}$-$Q^{3b}$-$R^{13}$, -$Q^{3a}$-COR$^{11}$, -$Q^{3a}$-CO-$Q^{3b}$-$R^{13}$, -$Q^{3a}$-$NR^{11}COR^{12}$, -$Q^{3a}$-$NR^{11}$CO-$Q^{3b}$-$R^{13}$, -$Q^{3a}$-$NR^{11}$C(O)$OR^{12}$, -$Q^{3a}$-$SO_2R^{11}$, -$Q^{3a}$-$SO_2$-$Q^{3b}$-$R^{13}$, $Q^{3a}$-CONR$^{11}R^{12}$, -$Q^{3a}$-CONR$^{11}$-$Q^{3b}$-$R^{13}$, -$Q^{3a}$-$CO_2R^{11}$, -$Q^{3a}$-$CO_2$-$Q^{3b}$-$R^{13}$, -$Q^{3a}$-$SO_2NR^{11}R^{12}$, -$Q^{3a}$-$SO_2NR^{11}$-$Q^{3b}$-$R^{13}$, -$Q^{3a}$-$NR^{11}SO_2R^{12}$, -$Q^{3a}$-$NR^{11}SO_2$-$Q^{3b}$-$R^{13}$ and -$Q^{3a}$-$NR^{11}SO_2NR^{12}R^{12a}$, -$Q^{3a}$-$NR^{11}SO_2NR^{12}$-$Q^{3b}$-$R^{13}$;

$Q^{3a}$ and $Q^{3b}$ are each independently a covalent bond, $C_1$-$C_6$ alkylene, or $C_2$-$C_6$ alkenylene;
$R^{11}$, $R^{12}$ and $R^{12a}$ are each independently hydrogen or $C_1$-$C_6$ alkyl;
$R^{13}$ is a 3 to 10-membered, monocyclic or bicyclic, heterocyclyl, heteroaryl, aryl, or cycloalkyl ring; wherein said heterocyclyl and heteroaryl rings comprise 1 to 5 heteroatoms, each independently selected from N, O and S;
wherein $R^{13}$ is unsubstituted or substituted with one to four substituents, each independently selected from halogen, hydroxyl, thiol, cyano, amino, amido, nitro, $SF_5$, $C_1$-$C_3$ alkyl, and $C_1$-$C_3$ alkoxy;
each $Q^2$ is independently halogen, cyano, nitro, $OR^5$, —$SR^5$, —$NR^5R^6$, —$CONR^5R^6$, —$C_0$-$C_3$-alkylene-$NR^5COR^6$—, —$NR^5CONR^6R^{6a}$, —$COR^5$, —C(O)$OR^5$, —$SO_2R^5$, —$SO_2NR^5R^6$, —$NR^5SO_2R^6$, —$NR^5SO_2NR^6R^{6a}$, —$NR^5C(O)OR^6$, —$C_1$-$C_6$ alkyl, —$C_2$-$C_6$ alkenyl, a covalent bond, an oxygen atom, a sulphur atom, —$OR^7$—, —SO—, —$SO_2$—, —CO—, —C(O)O—, —$C_0$-$C_3$-alkylene-C(O)$NR^5$—$C_0$-$C_3$ alkylene, —$C_0$-$C_3$-alkylene-$NR^5$—$C_0$-$C_3$ alkylene, —$C_0$-$C_3$ alkylene-$NR^5$C(O)—$C_0$-$C_3$ alkylene, —$NR^5CONR^6$—, —$SO_2NR^5$—, $NR^5SO_2$—, —$NR^5SO_2NR^6$—, —$NR^5$C(O)O—, —$NR^5$C(O)$OR^7$—, $C_1$-$C_6$ alkylene, or —$C_2$-$C_6$ alkenylene,
$R^5$, $R^6$, $R^{6a}$ are each independently hydrogen or $C_1$-$C_6$ alkyl,
$R^7$ is $C_1$-$C_6$ alkylene;
each D is independently a 3 to 10-membered, monocyclic or bicyclic, heterocyclyl, heteroaryl, cycloalkyl or aryl ring; wherein said heterocyclyl and heteroaryl rings comprise 1 to 5 heteroatoms, each independently selected from N, O and S;
wherein D is unsubstituted or substituted with one to four substituents, each independently selected from $C_1$-$C_6$ alkyl, $C_1$-$C_6$ alkoxy, and —$CONR^{14}R^{15}$;
$R^{14}$ and $R^{15}$ are each independently hydrogen or $C_1$-$C_6$ alkyl, and
wherein the alkyl, alkoxy, alkenyl, alkynyl, alkylene and alkenylene groups of $R^{1a}$, $R^{1b}$, $R^{1c}$, $R^{1d}$, $R^2$, $R^3$, $R^4$, $R^5$, $R^6$, $R^{6a}$, $R^7$, $R^{11}$, $R^{12}$, $R^{12a}$, $R^{14}$, $R^{15}$, $Q^1$, $Q^2$, $Q^{3a}$, $Q^{3b}$, ring B substituents and ring D substituents, are optionally substituted with halogen, hydroxyl or cyano.

2. The compound according to claim 1, wherein $R^8$ is -$Q^1$-B; and $R^{10}$ is hydrogen or -$Q^2$-$(D)_m$.

3. The compound according to claim 1, wherein $R^8$ is hydrogen or -$Q^2$-$(D)_m$; and $R^{10}$ is -$Q^1$-B.

4. The compound according to claim 1, wherein $Q^1$ is selected from a covalent bond, $CH_2NHC(O)$, NH, $CH_2$, or $CH_2NHC(O)CH_2$.

5. The compound according to claim 1, wherein B is selected from phenyl, quinolinyl, pyridinyl, pyrazolyl, indazolyl, imidazolyl, isoquinolinyl and imidazopyridinyl.

6. The compound according to claim 1, wherein B is substituted with one to four substituents selected from fluorine, chlorine, cyano, methyl, propyl, $CF_3$, methoxy, propoxy, $OCF_3$, $C(O)NH_2$, $C(O)NHCH_3$, $C(O)N(CH_3)_2$, $SO_2N(CH_3)_2$, $R^{13}$, $CH_2R^{13}$, C(O)$NHR^{13}$, C(O)$NHCH_2R^{13}$, NHC(O)—($C_2$ alkylene)-$R^{13}$, C(O)NH-ethylene-$R^{13}$, OCH₂R¹³, OR¹³, C(O)R¹³, SO₂NH, and NHSO₂R¹³; wherein R¹³ is selected from phenyl, pyridinyl, piperazinyl and cyclopropyl.

7. The compound according to claim 1, wherein each occurrence of Q² is independently selected from a covalent bond, methyl, isopropyl, NHC(O)CH₃, CH₂, NH, or CH₂NR⁵C(O).

8. The compound according to claim 1, wherein D is selected from phenyl, isoquinolinyl and pyridinyl.

9. The compound according to claim 1, wherein R¹ᵃ, R¹ᵇ, R¹ᶜ and R¹ᵈ each represent hydrogen.

10. A compound selected from the group consisting of:
1-(4-methoxyphenyl)-4,6-dihydropyrrolo[3,4-c]pyrazole-5(1H)-carbonitrile;
1-phenyl-4,6-dihydropyrrolo[3,4-c]pyrazole-5(1H)-carbonitrile;
1-(4-fluorophenyl)-4,6-dihydropyrrolo[3,4-c]pyrazole-5 (1H)-carbonitrile;
1-(2-fluorophenyl)-4,6-dihydropyrrolo[3,4-c]pyrazole-5 (1H)-carbonitrile;
4-(5-cyano-5,6-dihydropyrrolo[3,4-c]pyrazol-1(4H)-yl)benzamide;
1-(quinolin-3-yl)-4,6-dihydropyrrolo[3,4-c]pyrazole-5 (1H)-carbonitrile;
1-(3-methoxyphenyl)-4,6-dihydropyrrolo[3,4-c]pyrazole-5(1H)-carbonitrile;
1-(1-phenyl-1H-pyrazol-4-yl)-4,6-dihydropyrrolo[3,4-c]pyrazole-5(1H)-carbonitrile;
1-(1-phenyl-1H-imidazol-4-yl)-4,6-dihydropyrrolo[3,4-c]pyrazole-5(1H)-carbonitrile;
3-methyl-1-phenyl-4,6-dihydropyrrolo[3,4-c]pyrazole-5 (1H)-carbonitrile;
N-benzyl-3-(5-cyano-5,6-dihydropyrrolo[3,4-c]pyrazol-1 (4H)-yl)benzamide;
3-(5-cyano-5,6-dihydropyrrolo[3,4-c]pyrazol-1 (4H)-yl)-N-(1-phenylethyl)benzamide;
3-(5-cyano-5,6-dihydropyrrolo[3,4-c]pyrazol-1 (4H)-yl)-N-(pyri din-2-ylmethyl)benzamide;
4-(5-cyano-5,6-dihydropyrrolo[3,4-c]pyrazol-1 (4H)-yl)-N-(pyridin-2-ylmethyl)benzamide;
4-(5-cyano-5,6-dihydropyrrolo[3,4-c]pyrazol-1 (4H)-yl)-N-methylbenzamide;
4-(5-cyano-3-methyl-5,6-dihydropyrrolo[3,4-c]pyrazol-1 (4H)-yl)benzamide;
1-(1-methyl-1H-indazol-5-yl)-4,6-dihydropyrrolo[3,4-c]pyrazole-5(1H)-carbonitrile;
5-(5-cyano-5,6-dihydropyrrolo[3,4-c]pyrazol-1 (4H)-yl)-2-methoxy-N-methylbenzamide;
1-(1H-indazol-3-yl)-4,6-dihydropyrrolo[3,4-c]pyrazole-5 (1H)-carbonitrile;
1-(3-phenyl-1H-pyrazol-5-yl)-4,6-dihydropyrrolo[3,4-c]pyrazole-5(1H)-carbonitrile;
1-methyl-3-phenyl-4,6-dihydropyrrolo[3,4-c]pyrazole-5 (1H)-carbonitrile;
2-methyl-3-phenyl-2,6-dihydropyrrolo[3,4-c]pyrazole-5 (4H)-carbonitrile;
1-isopropyl-3-phenyl-4,6-dihydropyrrolo[3,4-c]pyrazole-5(1H)-carbonitrile;
1-benzyl-3-phenyl-4,6-dihydropyrrolo[3,4-c]pyrazole-5 (1H)-carbonitrile;
1-benzyl-3-(5-isopropyl-2-methoxyphenyl)-4,6-dihydropyrrolo[3,4-c]pyrazole-5 (1H)-carbonitrile;
3-(5-isopropyl-2-methoxyphenyl)-4,6-dihydropyrrolo[3,4-c]pyrazole-5(1H)-carbonitrile;
3-(2-fluoro-5-methylphenyl)-4,6-dihydropyrrolo[3,4-c]pyrazole-5(1H)-carbonitrile;
5-(5-cyano-5,6-dihydropyrrolo[3,4-c]pyrazol-1 (4H)-yl)-1H-pyrazole-3-carboxamide;
3-phenyl-4,6-dihydropyrrolo[3,4-c]pyrazole-5(1H)-carbonitrile;
3-(isoquinolin-3-yl amino)-2-methyl-2,6-dihydropyrrolo[3,4-c]pyrazole-5(4H)-carbonitrile;
3-(isoquinolin-3-ylamino)-4,6-dihydropyrrolo[3,4-c]pyrazole-5(1H)-carbonitrile;
1-benzyl-3-(isoquinolin-3-ylamino)-4,6-dihydropyrrolo[3,4-c]pyrazole-5(1H)-carbonitrile;
4-(5-cyano-3-(pyridin-2-ylamino)-5,6-dihydropyrrolo[3,4-c]pyrazol-1 (4H)-yl)benzamide;
N-((5-cyano-1,4,5,6-tetrahydropyrrolo[3,4-c]pyrazol-3-yl)methyl)-3-phenyl-1H-pyrazole-5-carboxamide;
N-((5-cyano-1-phenyl-1,4,5,6-tetrahydropyrrolo[3,4-c]pyrazol-3-yl)methyl)-4-methylbenzamide;
N-((5-cyano-1-phenyl-1,4,5,6-tetrahydropyrrolo[3,4-c]pyrazol-3-yl)methyl)acetamide;
3-(4-(benzyloxy)phenyl)-4,6-dihydropyrrolo[3,4-c]pyrazole-5(1H)-carbonitrile;
3-(3-cyanophenyl)-4,6-dihydropyrrolo[3,4-c]pyrazole-5 (1H)-carbonitrile;
3-(1-methyl-1H-pyrazol-5-yl)-4,6-dihydropyrrolo[3,4-c]pyrazole-5(1H)-carbonitrile;
3-(3-(trifluoromethoxy)phenyl)-4,6-dihydropyrrolo[3,4-c]pyrazole-5 (1H)-carbonitrile;
3-(4-phenoxyphenyl)-4,6-dihydropyrrolo[3,4-c]pyrazole-5(1H)-carbonitrile;
3-(4-cyanophenyl)-4,6-dihydropyrrolo[3,4-c]pyrazole-5 (1H)-carbonitrile;
3-(2-fluoro-4-(trifluoromethyl)phenyl)-4,6-dihydropyrrolo[3,4-c]pyrazole-5(1H)-carbonitrile;
3-(2-chloro-5-(trifluoromethoxy)phenyl)-4,6-dihydropyrrolo[3,4-c]pyrazole-5(1H)-carbonitrile;
5-(5-cyano-1,4,5,6-tetrahydropyrrolo[3,4-c]pyrazol-3-yl)-N-methylpicolinamide;
3-(6-methoxypyridin-3-yl)-4,6-dihydropyrrolo[3,4-c]pyrazole-5(1H)-carbonitrile;
3-(5-cyano-1,4,5,6-tetrahydropyrrolo[3,4-c]pyrazol-3-yl)-N,N-dimethylbenzenesulfonamide;
3-(5-fluoro-2-isopropoxyphenyl)-4,6-dihydropyrrolo[3,4-c]pyrazole-5(1H)-carbonitrile;
N-benzyl-4-(5-cyano-1,4,5,6-tetrahydropyrrolo[3,4-c]pyrazol-3-yl)benzamide;
3-(6-isopropoxypyridin-3-yl)-4,6-dihydropyrrolo[3,4-c]pyrazole-5 (1H)-carbonitrile;
3-(4-(4-methylpiperazine-1-carbonyl)phenyl)-4,6-dihydropyrrolo[3,4-c]pyrazole-5 (1H)-carbonitrile;
3-(1-methyl-1H-indazol-5-yl)-4,6-dihydropyrrolo[3,4-c]pyrazole-5(1H)-carbonitrile;
3-(1-benzyl-1H-pyrazol-5-yl)-4,6-dihydropyrrolo[3,4-c]pyrazole-5(1H)-carbonitrile;
3-(5-methyl-1H-indazol-4-yl)-4,6-dihydropyrrolo[3,4-c]pyrazole-5(1H)-carbonitrile;
3-(5-cyano-1,4,5,6-tetrahydropyrrolo[3,4-c]pyrazol-3-yl)-N-cyclopropylbenzenesulfonamide;
N-(3-(5-cyano-1,4,5,6-tetrahydropyrrolo[3,4-c]pyrazol-3-yl)phenyl)cyclopropanesulfonamide;
3-(3-fluorophenyl)-4,6-dihydropyrrolo[3,4-c]pyrazole-5 (1H)-carbonitrile;
3-(2-fluorophenyl)-4,6-dihydropyrrolo[3,4-c]pyrazole-5 (1H)-carbonitrile;
3-(4-fluorophenyl)-4,6-dihydropyrrolo[3,4-c]pyrazole-5 (1H)-carbonitrile;
3-(2-fluoro-5-methylphenyl)-1-methyl-4,6-dihydropyrrolo[3,4-c]pyrazole-5 (1H)-carbonitrile;

3-(2-fluoro-5-methylphenyl)-2-methyl-2,6-dihydropyr- rolo[3,4-c]pyrazole-5 (4H)-carbonitrile;
3-(5-isopropyl-2-methoxyphenyl)-1-methyl-4,6-dihydro- pyrrolo[3,4-c]pyrazole-5 (1H)-carbonitrile;
3-(5-isopropyl-2-methoxyphenyl)-2-methyl-2,6-dihydro- pyrrolo[3,4-c]pyrazole-5 (4H)-carbonitrile;
3-(5-ethyl-2-methoxyphenyl)-4,6-dihydropyrrolo[3,4-c] pyrazole-5(1H)-carbonitrile;
6-chloro-N-((5-cyano-1,4,5,6-tetrahydropyrrolo[3,4-c] pyrazol-3-yl)methyl)imidazo[1,2-a]pyridine-2-carbox- amide;
3-(4-(4-methylpiperazin-1-yl)phenyl)-4,6-dihydropyrrolo [3,4-c]pyrazole-5 (1H)-carbonitrile;
3-(4-chloro-2-methoxyphenyl)-4,6-dihydropyrrolo[3,4-c] pyrazole-5(4H)-carbonitrile;
3-(1-(1-methylpiperidin-4-yl)-1H-pyrazol-4-yl)-4,6-di- hydropyrrolo[3,4-c]pyrazole-5 (1H)-carbonitrile;
3-(6-(4-methylpiperazin-1-yl)pyridin-3-yl)-4,6-dihydro- pyrrolo[3,4-c]pyrazole-5 (1H)-carbonitrile;
3-(2-methoxy-4-(1H-pyrazol-1-yl)phenyl)-4,6-dihydro- pyrrolo[3,4-c]pyrazole-5(4H)-carbonitrile;
3-(3-(4-methylpiperazin-1-yl)phenyl)-4,6-dihydropyrrolo [3,4-c]pyrazole-5 (1H)-carbonitrile;
3-(4-morpholinophenyl)-4,6-dihydropyrrolo[3,4-c]pyra- zole-5(1H)-carbonitrile;
3-(2-fluoro-4-(4-methylpiperazin-1-yl)phenyl)-4,6-dihy- dropyrrolo[3,4-c]pyrazole-5(1H)-carbonitrile;
3-(3-methyl-4-(4-methylpiperazin-1-yl)phenyl)-4,6-dihy- dropyrrolo[3,4-c]pyrazole-5(1H)-carbonitrile;
3-(3-(2-oxooxazolidin-3-yl)phenyl)-4,6-dihydropyrrolo [3,4-c]pyrazole-5(1H)-carbonitrile;
3-(3-(2-oxopyrrolidin-1-yl)phenyl)-4,6-dihydropyrrolo [3,4-c]pyrazole-5 (1H)-carbonitrile;
3-(5-chloro-2-methoxyphenyl)-4,6-dihydropyrrolo[3,4-c] pyrazole-5(4H)-carbonitrile;
N-(3-(5-cyano-5,6-dihydropyrrolo[3,4-c]pyrazol-1 (4H)- yl)phenyl)cyclopropanesulfonamide; and
N-benzyl-4-(5-cyano-1,4,5,6-tetrahydropyrrolo[3,4-c] pyrazol-3-yl)-3-fluorobenzamide;
a tautomer thereof, or a pharmaceutically acceptable salt of said compound or tautomer.

11. A pharmaceutical composition comprising a compound according to claim 1, a tautomer thereof, or a pharmaceutically acceptable salt of said compound or tautomer, together with one or more pharmaceutically acceptable excipients.

\* \* \* \* \*

UNITED STATES PATENT AND TRADEMARK OFFICE
CERTIFICATE OF CORRECTION

| | | |
|---|---|---|
| PATENT NO. | : 11,306,096 B2 | |
| APPLICATION NO. | : 16/080229 | |
| DATED | : April 19, 2022 | |
| INVENTOR(S) | : Alison Jones et al. | |

It is certified that error appears in the above-identified patent and that said Letters Patent is hereby corrected as shown below:

In the Claims

At Column 83, Line 48, "-NR2SO2-," should be removed.

At Column 83, Line 49, "-NR2C(O)-" should be printed as "-NR2C(O)O-.".

At Column 84, Line 4, "and" should be replaced with "," and before "-Q3a-" an --and-- should be inserted.

Signed and Sealed this
Fourth Day of July, 2023

Katherine Kelly Vidal
*Director of the United States Patent and Trademark Office*